US010363420B2

(12) United States Patent
Fried et al.

(10) Patent No.: US 10,363,420 B2
(45) Date of Patent: Jul. 30, 2019

(54) SYSTEMS AND METHODS FOR RESTORING COGNITIVE FUNCTION

(71) Applicant: THE REGENTS OF THE UNIVERSITY OF CALIFORNIA, Oakland, CA (US)

(72) Inventors: Itzhak Fried, Los Angeles, CA (US); Dejan Markovic, Los Angeles, CA (US); Nanthia Suthana, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/317,319

(22) PCT Filed: Jun. 9, 2015

(86) PCT No.: PCT/US2015/034962
§ 371 (c)(1),
(2) Date: Dec. 8, 2016

(87) PCT Pub. No.: WO2015/191628
PCT Pub. Date: Dec. 17, 2015

(65) Prior Publication Data
US 2017/0113046 A1 Apr. 27, 2017

Related U.S. Application Data

(60) Provisional application No. 62/009,884, filed on Jun. 9, 2014.

(51) Int. Cl.
*A61N 1/36* (2006.01)
*G16H 50/50* (2018.01)
(Continued)

(52) U.S. Cl.
CPC ........ *A61N 1/36082* (2013.01); *A61B 5/0476* (2013.01); *A61B 5/0478* (2013.01);
(Continued)

(58) Field of Classification Search
CPC ................ A61N 1/0534; A61N 1/0531; A61N 1/36082; A61B 5/055; A61B 5/0531
See application file for complete search history.

(56) References Cited

U.S. PATENT DOCUMENTS

2006/0173259 A1* 8/2006 Flaherty ............... A61B 5/0031
600/331
2008/0004660 A1 1/2008 Assaf et al.
(Continued)

FOREIGN PATENT DOCUMENTS

CN 203043423 U 7/2013

OTHER PUBLICATIONS

Nanthia, S. et al., "Memory Enhancement and Deep-Brain Stimulation of the Entorhinal Area," The New England Journal of Medicine, vol. 366, pp. 502-510, Feb. 9, 2012.
(Continued)

*Primary Examiner* — Alyssa M Alter
(74) *Attorney, Agent, or Firm* — Morgan, Lewis & Bockius LLP

(57) ABSTRACT

Systems and methods for restoring cognitive function are disclosed. In some implementations, a method includes, at a computing device, separately stimulating one or more of lateral and medial entorhinal afferents and other structures connecting to a hippocampus of an animal subject in accordance with a plurality of predefined stimulation patterns, thereby attempting to restore object-specific memories and location-specific memories; collecting a plurality of one or more of macro- and micro-recordings of the stimulation of hippocampalentorhinal cortical (HEC) system; and refining (Continued)

the computational model for restoring individual memories in accordance with a portion of the plurality of one or more of macro- and micro-recordings.

8 Claims, 16 Drawing Sheets

(51) Int. Cl.
| | |
|---|---|
| *A61B 5/0476* | (2006.01) |
| *A61B 5/00* | (2006.01) |
| *A61N 1/05* | (2006.01) |
| *A61B 5/0478* | (2006.01) |
| *A61B 5/055* | (2006.01) |
| *G06F 19/00* | (2018.01) |
| *A61N 1/372* | (2006.01) |
| *A61N 1/02* | (2006.01) |

(52) U.S. Cl.
CPC ............ *A61B 5/055* (2013.01); *A61B 5/4064* (2013.01); *A61B 5/4094* (2013.01); *A61B 5/4836* (2013.01); *A61B 5/6868* (2013.01); *A61N 1/025* (2013.01); *A61N 1/0531* (2013.01); *A61N 1/36139* (2013.01); *A61N 1/37229* (2013.01); *G06F 19/3481* (2013.01); *G16H 50/50* (2018.01); *A61N 1/0534* (2013.01); *A61N 1/36092* (2013.01); *A61N 1/36125* (2013.01)

(56) References Cited

U.S. PATENT DOCUMENTS

| | | |
|---|---|---|
| 2011/0106206 A1 | 5/2011 | Schiff |
| 2012/0016436 A1 | 1/2012 | Sarma et al. |
| 2012/0059438 A1 | 3/2012 | De Ridder |
| 2012/0289869 A1 | 11/2012 | Tyler |
| 2013/0184780 A1 | 7/2013 | Pless et al. |

OTHER PUBLICATIONS

The Regents of the University of California, International Search Report and Written Opinion, PCT/US2015/034962, dated Sep. 17, 2015, 9 Pgs.

The Regents of the University of California, International Preliminary Report on Patentability, PCT/US2015/034962, dated Dec. 15, 2016, 6 pgs.

The Regentes of the University of California, Communication Pursuant to Rules 161(2) and 162, EP15806123.4, dated Feb. 15, 2017, 2 pgs.

Berger et al., "Restoring lost cognitive function," IEEE Engineering in Medicine and Biology Magazine, IEEE Service Center, vol. 24, No. 6, Sep. 1, 2005, 15 pgs.

The Regentes of the University of California, Extended European Search Report, EP15806123.4, Mar. 9, 2018, 6 pgs.

The Regentes of the University of California, Communication Pursuant to Rules 70(2) and 70a(2), EP15806123.4, Mar. 27, 2018, 1 pg.

* cited by examiner

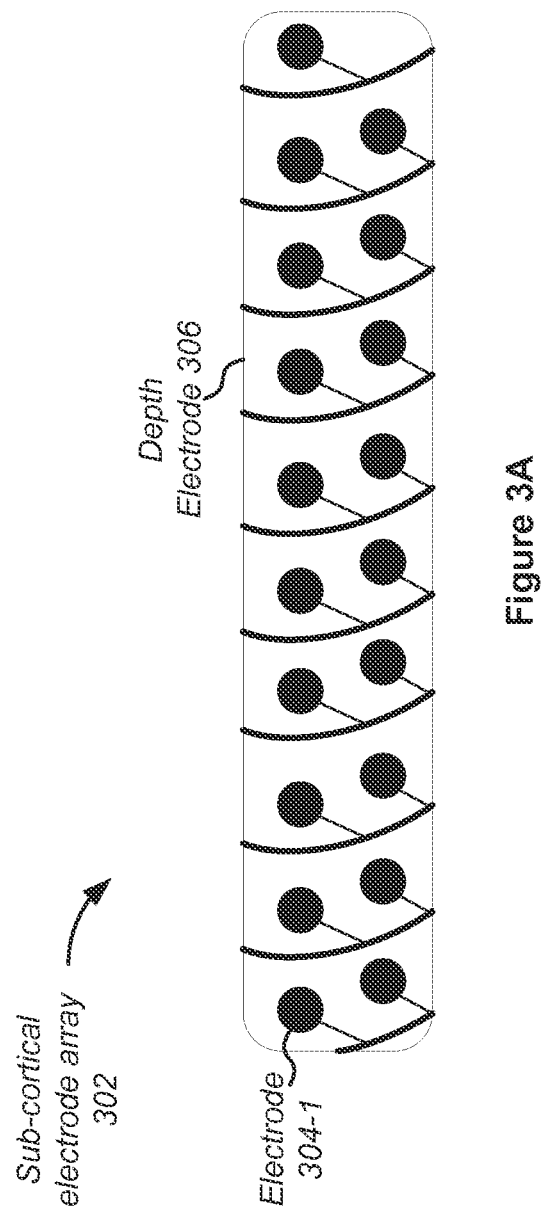

SYSTEMS AND METHODS FOR RESTORING COGNITIVE FUNCTION

TECHNICAL FIELD

The implementations disclosed herein relate generally cognitive restoration, including, but not limited to, wireless implants for use with memory restoration.

BACKGROUND

Loss of memory is one of the most dreaded afflictions of the human condition. Devastation hurled upon the human brain by trauma, stroke, epilepsy or processes of degenerations afflict a vast number of people in the US and worldwide. Traumatic brain injury ("TBI") is a leading cause of disability in young adults. Over 5.3 million people in the US live with long-term disability as a result of TBI and 70-80% of them are impaired by memory deficits. Memory impairment is strongly linked to the ability of TBI survivors to return to work and live independently. Moderate to severe memory impairment is also a feature of epilepsy, which affects over 2 million people in the US, many of them under 45 years of age. With progress in neuroscience and engineering, further discoveries in the neural substrates of human memory, and the emergence of novel neurotechnologies, the developments of therapies aimed at restoration of memory have become a major medical and social priority.

With advances in technologies to probe the human brain, electrical stimulation has emerged as a potential avenue for therapeutic intervention. However, the effects of brain stimulation on behavior are highly dependent on the precise location of delivery. For example, deep brain stimulation ("DBS") for treatment of Parkinson's disease is most effective when delivered to highly specific regions within the basal ganglia, such as the subthalamic nucleus and the globus pallidus, while DBS for depression is useful when delivered to the subcallosal cingulate gyrus.

Activation of previous experiences or memories has been shown to result from DBS of memory related brain circuits such as those within the temporal lobe. Electrical stimulation of areas in the temporal lobe can cause a small percentage of patients to report feelings of familiarity (also sometimes called "déjà vu") and the re-experiencing of old memories. Electrical stimulation of similar sites in the ventral temporal lobe has also resulted in the reporting of past experiences and sometimes the vague experiences of déjà vu. Extra-temporal stimulation of the hypothalamus has also been shown to create experiences of déjà vu and enhance verbal memory in a single patient. However, there is a lack of control over which memories are to be re-experienced or whether these are in fact specific memories from the past.

SUMMARY

The disclosed implementations include a safe state-of-the-art miniature, wireless, chronically implantable neuromodulation system that incorporates both single-neuron and local field potentials ("LFP") recordings into a closed-loop system that is chronically implanted in human patients with memory deficits, such as patients with traumatic brain injury. This system allows for stimulation and recording from multiple channels located on a pair of high-density sub-cortical electrode arrays. In some implementations, the multi-channel system includes: (1) two co-axial external primary RF-coils for transcutaneous power and data transfer between the external and implanted devices; (2) implanted electronics module with electronics for stimulation and recording; (3) secondary co-axial RF coils for secure power and data telemetry; (4) a sub-cortical neural probe for implantation in the entorhinal region (multi-channel); (5) a sub-cortical neural probe for implantation in the hippocampus (multi-channel); and (6) an external wearable earpiece with embedded memory model and secure wireless link to the implant as well as wireless link to a mobile device (e.g., a phone or tablet).

Unlike other cortical areas, the medial temporal lobe ("MTL") is a brain region that is clearly related to declarative memory function. Direct manipulation of this circuitry, in particular of the hippocampal-entorhinal cortex network offers a unique opportunity to influence learning and memory performance. Interestingly electrical stimulation of the hippocampus proper interferes with retrieval of information.

However DBS of the entorhinal area enhances spatial memory in humans when DBS is provided during the learning phase. Stimulation of the entorhinal area may enhance hippocampal dependent memory because of close proximity of electrodes to the perforant pathway. The proposed implementations utilize advanced technology such as high-resolution diffusion tensor imaging ("DTI"), which can elucidate the exact area of entorhinal DBS placement within humans to determine proximity to the perforant pathway. DBS of various other regions outside the MTL (e.g. anterior nucleus of the thalamus, hypothalamus, and septal nucleus, or even the vagus nerve) that have efferent and afferent connections to the hippocampus also enhance memory. However, the nature of this memory enhancement from DBS of these areas may be due to overall increases in attention, arousal, or perceptuomotor function. Although entorhinal DBS induced memory enhancement is not due to enhancement of perceptuomotor functions, other stimulated regions (e.g., vagus nerve) may affect memory through these or other alternative cognitive functions.

Direct macro-electrode DBS of the hippocampus generally shows disruptions in memory. The use of macroelectrodes and thus stimulation of a large population of hippocampal neurons especially when given above the threshold to elicit after-discharges may disrupt local neuronal circuitry necessary for successful learning. The disclosed implementations include determining how large the population of stimulated hippocampal neurons needs to be in order to reach a threshold for behavioral changes.

The nature of the stimulation also affects memory. In rodents, when hippocampal electrical stimulation matches hippocampal input activity with respect to both spatial and temporal firing patterns, memory enhancement may result. Furthermore, optogenetic reactivation of hippocampal neurons that are activated during learning leads to enhanced memory expression. Thus, stimulation of the hippocampus directly can lead to both disruption and enhancement of memory, depending on the precise effect stimulation has on underlying neuronal activity. The use of specific and physiologically meaningful hippocampal stimulation combined with entorhinal afferent stimulation thus enhances memory.

It is important to note that the tasks used to measure memory performance differ widely (e.g., across various DBS studies). For example, studies have used both verbal and spatial memory tasks, but not both within the same study. Neuroanatomical studies suggest that the posterior, rather than the anterior, portion of the hippocampus receives and sends more spatially relevant information. Thus, some implementations include characterization of the precise effects of stimulation at anterior versus posterior MTL structures during a variety of memory tasks. In some implementations, DBS application is be provided unilaterally while in others, DBS application is provided bilaterally. Bilateral stimulation can modulate memory, however, unilateral stimulation may be sufficient in some implementations. Thus, some implementations include comparing bilateral versus unilateral DBS results in memory enhancement.

Using algorithms based on recorded single neuron and LFP activity, the system delivers electrical stimulation patterns designed to restore and enhance memory in patients and is regulated by feedback in a closed loop.

The disclosed implementations have several advantages over current technologies. For example, the disclosed implementations include chronically implantable high-channel-count polymer-based arrays microfabricated for long-term stability. These polymers have much lower elastic modulus (e.g., ~3 GPa) compared to state-of-the-art silicon devices (e.g., ~200 GPa) or microwire devices (e.g., ~100 GPa) and much lower foreign body response. In addition, in some implementations, high-density miniaturized packages are provided for compact electronic systems that can be embedded using less invasive surgical techniques. Moreover, in disclosed implementations include use of a 200 mVpp artifact-free input range (a 20× better than existing technology) by employing signal processing in phase domain, without impact on power (e.g., less than 1 µW/ch for LFPs). Furthermore, the disclosed implementations include use of an adaptive filter to remove stimulation artifact from affected recording channels. Finally, the disclosed implementations include use of frequency-division multiplexing, combined with impedance-based filtering, which enables sharing of an input amplifier across several channels and effectively reducing power without compromising signal-to-noise ratio.

A combination of above techniques, together with secure wireless data and power transfer, allows for use of a small (e.g., less than 1 cm$^3$) multichannel (e.g., 64-channel) battery-free implantable neural recording and stimulation device. The disclosed implementations improve the current art, e.g., by ~10× in electrode array density and ~100× in device volume/channel.

BRIEF DESCRIPTION OF THE DRAWINGS

For a better understanding of the various described implementations, reference should be made to the Description of Implementations below, in conjunction with the following drawings in which like reference numerals refer to corresponding parts throughout the figures.

FIGS. 3A-3C illustrate exemplary sub-cortical electrode arrays, in accordance with some implementations.

Like reference numerals refer to corresponding parts throughout the several views of the drawings.

DESCRIPTION OF IMPLEMENTATIONS

Figure 1:
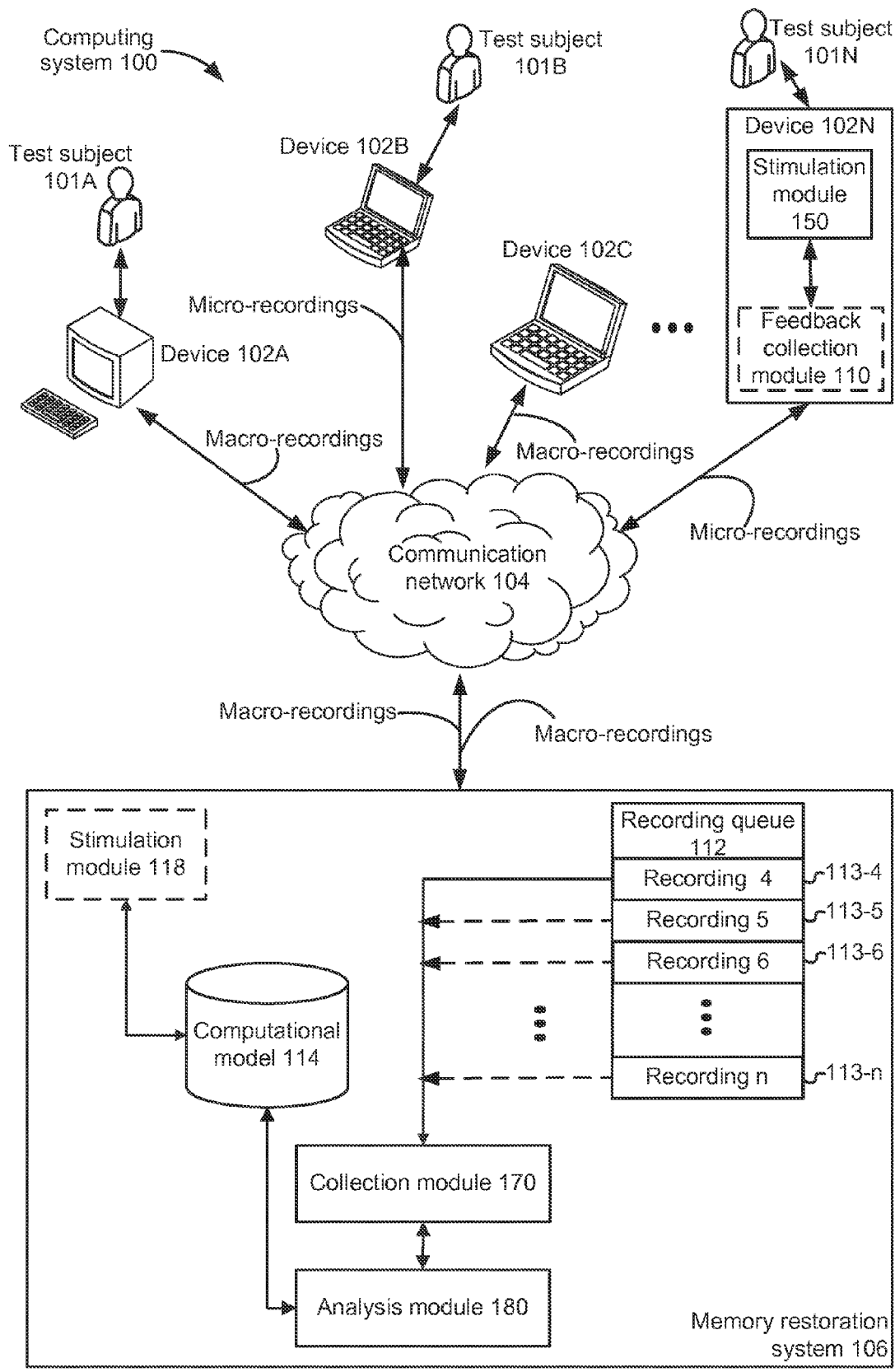
FIG. 1 is a block diagram illustrating a computing system 100 for restoring memories, in accordance with some implementations.

The present disclosure provides a unique and powerful modulation of the hippocampal-entorhinal system of the human brain, which is based, not only on hypothesis-based models but also on a progression of data largely accumulated at UCLA. The present disclosure describes systems and methods for stimulating neurons and thereby attempting to restore cognitive functions such as memories.

The present disclosure also describes combining models derived from rodents, non-human primates, and human patients, and in some implementations, focuses on (1) neurosurgical epilepsy patients with semi-chronic and chronic recording and stimulation of the hippocampal-entorhinal system; and (2) TBI patients with closed loop modulation of that system.

The present disclosure describes combining in humans four technology layers in stages. These stages include: (1) depth electrode recordings in monitored epilepsy patients with externalized leads; (2) internalized chronic FDA-approved Responsive Stimulator ("RNS") systems in epilepsy patients chronically implanted for epilepsy indications with opportunity for long-term testing of memory restoration; (3) Activa PC+S modulation of the hippocampal-entorhinal system for primary indication of memory restoration in TBI patients; and (4) implantation of a tailored neuromodulation system in TBI patients for primary indication of memory restoration based on fully developed computation models.

The present disclosure describes capitalizing on a rare collaborative opportunity in computational modeling, in-vivo electrophysiology of memory, deep brain stimulation related memory enhancement in humans, traumatic brain injury, and leading-edge engineering technology. For example, simultaneous stimulation and recording of single neurons and local field potentials in rodents, non-human primates, and humans.

The ability to stimulate and record from single cells in the human hippocampus and entorhinal area for combined electrophysiology and stimulation of specific memories is unique. As discussed below, the present disclosure describes simultaneous microstimulation and single-unit and LFP recordings within the human hippocampus and entorhinal area.

While much progress has been made in generating brain machine interface and restoring motor function of limbs, it is much more difficult to Restore Active Memories ("RAM"), especially declarative memories. The present disclosure describes an approach that is biophysically grounded and sound, physiologically implementable, and practical enough to be of use in humans using a lightweight wireless device.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

FIG. 1 is a block diagram illustrating a computing system 100 (also sometimes called a "neuromodulation system") for restoring memories, in accordance with some implementations. In some implementations, the computing system 100 includes one or more devices 102 (e.g., device 102A, 102B, 102C, 102D . . . , and 102N), a communication network 104, and a memory restoration system 106. In some implementations, a device 102 is a brain scanning device, an MRI device, a tablet, and/or a computer (mobile or otherwise). In some implementations, a device 102 obtains micro- or macro-recordings from a test subject (e.g., an animal or a human being) through electronic detectors and cords, and transmits the micro- or macro-recordings to the restoration system 106 for analysis. In some implementations, a device 102 includes a stimulation module 150 and optionally a feedback collection module 110. In some implementations, a device 102 comprises an implantable component (e.g., implantable electronics package 200, FIG. 2) and an external wearable component (e.g., external earpiece 204, FIG. 2). In some implementations, a device 102 includes an implantable component, and an external wearable component, and a computing device such as a computer or tablet.

In some implementations, the stimulation module 150 sends stimulation signals to the brain of a test subject (e.g., to the hippocampal entorhinal cortical area of a TBI patient) in accordance with one or more specified computational models. In some implementations, the stimulation module 150 resident on the device 102 balances processing load with the stimulation module 118 resident on the system 106.

In some implementations, the communication network 104 interconnects one or more devices 102 with one another, and with the memory restoration system 106. In some implementations, the communication network 104 optionally includes the Internet, one or more local area networks (LANs), one or more wide area networks (WANs), other types of networks, or a combination of such networks.

In some implementations, the restoration system 106 includes a stimulation module, a computational model, a collection module, an analysis module, and a recording queue. In some implementations, the restoration system 106 generates stimulation signals to be sent to a test subject (e.g., using the stimulation module 118) and gathers feedback from the test subject (e.g., using the collection module 170). In some implementations, the restoration system 106 also refines the computational model 114 in accordance with the feedback collected. In some implementations, the analysis module 180 analyzes micro- and macro-recordings collected from a test subject and, based on the test subject's reactions to stimulating signals, refines the computational model, thereby increasing the likelihood for restoring memories of the test subject.

In some implementations, the collection module and/or the stimulation model are software, hardware, or a combination thereof resident on the device 102, such as a software application or a hardware chipset. In some implementations, the stimulation module 150 is not present, and a stimulation module 118, which exists separately from, or independent of, the device 102 is provided instead (e.g., as component of the server 106 or as standalone stimulation system component). In some implementations, the stimulation module 150 is a software/hardware component residing in the device 102, such as a software package/application or a hardware chipset. In some implementations, the stimulation module 150 is for generating stimulation signals to stimulate a test subject. That is, in some implementations, both a stimulation module 150 on the device 102 and a stimulation module 118 on a server 106 are used to stimulate a test subject.

Figure 4:
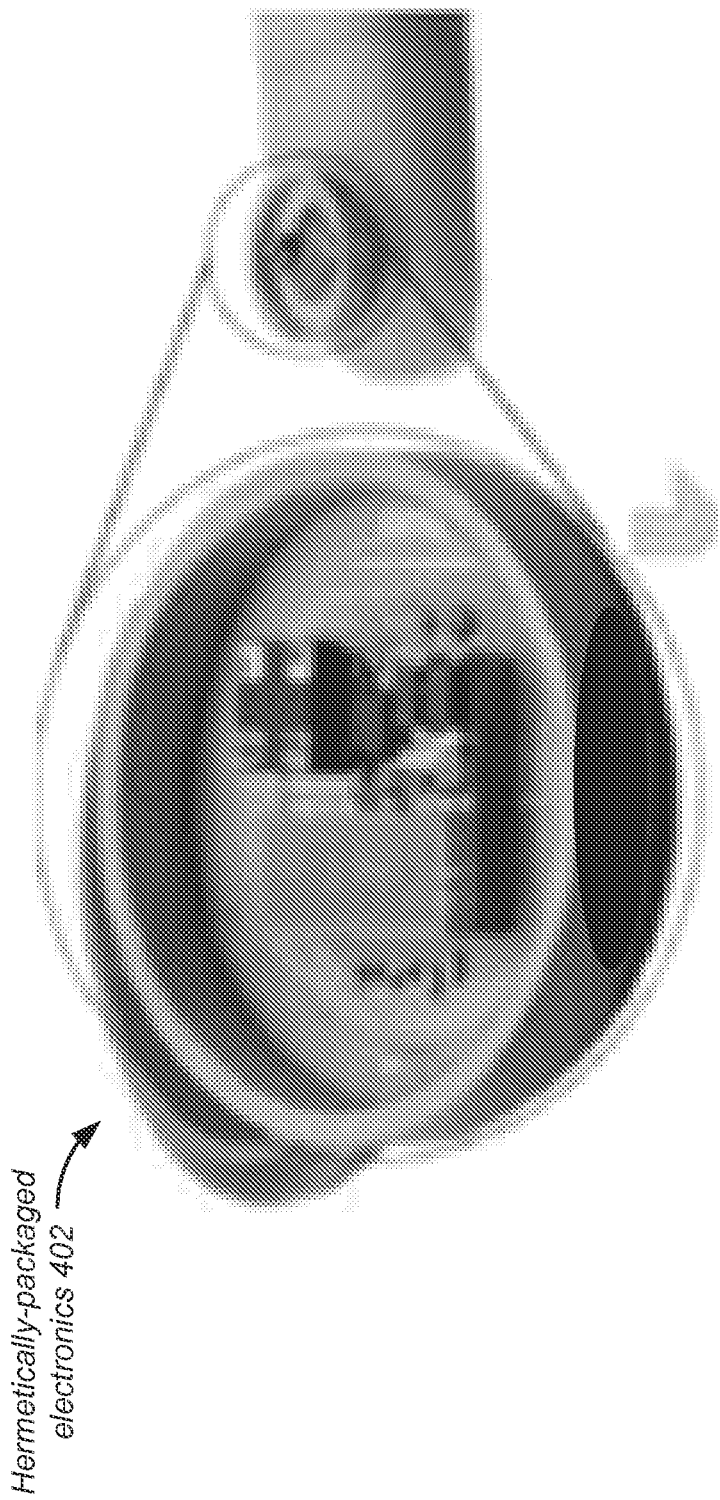
FIG. 4 illustrates exemplary hermetically-packaged battery-less electronics, in accordance with some implementations.

In some implementations, the recording queue 112 stores one or more recordings awaiting analysis (e.g., by the collection module 170 and/or analysis module 180), such as recording 4, recording 5, recording 6, . . . and recording n (FIG. 1, 113-4 . . . 113-$n$). In some implementations, the recording queue 112 includes different types of recordings, such as micro-recordings and macro-recordings.

In some implementations, the collection module 170 collects feedback to the stimulation signals from a test subject and refines the computational model 114 in accordance therewith. In some implementations, the computation model 114 is refined based on one or more recordings (e.g., one or more micro-recordings and/or one or more macro-recordings) as well as additional feedback received from the test subject, such as verbal feedback as to what the test subject experienced in response to the stimulation. In some implementations, the additional feedback includes feedback regarding the health of the test subject such as heart rate information, pain information, and the like. In some implementations, the additional feedback includes feedback received from other parts of the test subjects' brain such as the basal ganglia, the thalamus, and the like.

In some implementations, the memory stimulation techniques described herein are implemented via software stored in one or more computer memories and executed on one or more computer processors associated with a variety of computing resources, including local, network, or cloud computing resources. The software and computing resources are coupled with the stimulation electrodes and monitoring apparatus for, without limitation, stimulation, experiment control, and data collection purposes. The simulation and monitoring methods as well as electrode and equipment/experiment control methods are optionally implemented in respective software modules stored in memory of one or more of the computing resources. In different implementations, functions and data associated with these techniques are combined in varying ways in respective software modules. In some implementations, data generated and collected in the course of performing any of the techniques described herein, and data, experimental parameters and equipment settings employed in the course of performing any of the techniques described herein (e.g., stimulation sequences, computational models, etc.) are stored in various available computer and data storage resources (such as local, network or cloud storage).

Some implementations disclosed herein provide UCLA Medical Institutional Review Board ("IRB") approved protocols for macro- and micro-recording and stimulation of the hippocampal entorhinal cortical ("HEC") system in rodents, primates, and humans to refine a computational model. The computational model enhances specific declarative memories (and not others) as well as enhancing associations between specific items in memory and their associated spatial and temporal context.

In order to develop and refine a computational model able to restore individual memories in addition to supporting the formation of various types of hippocampal memories (e.g., spatial, item-specific, associative), the lateral and medial entorhinal afferents to the hippocampus are stimulated and the results are recorded and analyzed. While the lateral entorhinal cortex ("LEC") generally encodes information about physical stimuli such as objects, the medial entorhinal cortex ("MEC") generally encodes information about spatial location.

Some implementations employ specific stimulation patterns to both the LEC and MEC separately to restore both object-specific and location-specific memories. Some implementations record single neurons that support unique memory traces in human patients implanted with depth electrodes for clinical evaluation.

Some implementations employ a strongly established record of characterizing single neurons in the human HEC system that activate during recollection of previously viewed episodes in addition to particular cognitive categories and/or concepts. Some implementations involve using multi-electrode micro-stimulation to activate multiple neurons supporting a specific memory representation (e.g., for Jennifer Aniston) and consequent recollection of the memory and/or newly learned associations.

In some implementations, a computational model is based on signals obtained at the single neuron as well as LFP levels and thus reflects declarative memory codes at the levels of (1) firing rates of neurons; (2) timing of the firings; and (3) selective frequency characteristics of LFPs. Some implementations take advantage of the unique sparse code for "concepts", useful for memory encoding and retrieval. These concepts include general categories such as faces, objects, places, and animals, as well as attributes and associations for review. This code is readily related to place cells, grid cells, and directional cells in rodents and in humans. In some implementations, this code can be expanded to encode associations and episodes.

In some implementations, a large number of mixed selectivities are identified and these provide an additional and a more accessible level of decoding. Moreover, some implementations include analyzing simultaneous recordings of LFPs and single neuron activity and relying on LFPs to direct stimulation for restoration of specific memories. In response to consciously recognized images there is a theta peak which precedes the firing of the specific neurons, which appears to set the time window for conscious perception, but also a gamma response at the latency of neuronal firing which appears to be local and specific. Together with increased gamma-theta cross frequency coherence with entorhinal stimulation which enhances memory, manipulation of the frequency distribution of LFPs, in accordance with some implementations, enables restoration of specific memories.

While neurons that contribute to different memory representations (e.g., Jennifer Aniston and Eiffel tower) can be often found on the same electrode, the same pattern of memories is not found on all electrodes. For example, a separate electrode could have a neuron responsive to the same memory representation (e.g., Jennifer Aniston), but is unlikely to also have a neuron responsive to the other non-associated memory (e.g., Eiffel tower). Based on the consideration outlined above, some implementations include a Combinatorial-Fourier approach whereby various Fourier frequency patterns of activity are recorded and consequently leveraged for stimulating across different electrodes. For example, different electrodes that have neuronal representations for a particular memory (e.g., Jennifer Aniston), to selectively enhance specific complex declarative memories only (e.g., Jennifer Aniston) and not others (e.g., Eiffel tower). Using this approach, stimulation enhances connectivity among the neurons supporting a memory representation, thus enhancing the retrieveability of the memory. Neural activity in the HEC system, where declarative memories are formed, becomes strongly rhythmic during learning and memory tasks across a wide range of species. These rhythms: (1) span a broad range of oscillatory frequencies such as delta (0.5-2 Hz), theta (4-12 Hz), gamma (25-90 Hz), and ripples (100-250 Hz) each of which change according to behavioral state; (2) are tightly coupled to single neuron spiking activity; and (3) are used to predict successful memory. These rhythms can be modulated by stimulation and behavioral state in an intricate fashion such that low (e.g., 25-50 Hz) and high (e.g., 50-90 Hz) gamma rhythms appear at distinct phases of theta oscillations. This cross-frequency theta-gamma coupling is modulated by behaviors such as navigation, running, decision-making, learning, and memory. Moreover, this cross-frequency theta-gamma coupling is modulated by stimulation-induced specific memory enhancement.

Also, since LEC inputs are predominantly in one Fourier range (e.g., the 20-45 Hz Fourier range) and MEC inputs are predominately in a second Fourier range (e.g., in the 45-90 Hz Fourier range), ERC-CA1 connections can be selectively stimulated at alternating slow and fast gamma frequencies in proximal an distal parts of CA1 to enhance binding of separate items to LEC and MEC inputs. Spike-LFP activation patterns are optionally also incorporated into the computational model to determine the optimal closed-loop stimulation pattern for inducing synaptic plasticity for the formation of robust memory traces.

The final step of this Fourier-combinatorial approach is to fully implement the memory specific enhancement at the network level, thus facilitating RAM by increasing neural coupling in the HEC circuit. In some implementations, actual stimulation is optimized (e.g., by using theta-burst stimulation), in order to most effectively induce synaptic plasticity or long-term potentiation, which is necessary for successful memory formation. In some implementations, memory enhancement in humans includes using simple gamma 50 Hz stimulation. In some implementations, these memory improvements are strengthened through the use of an efficient multiscale computational model. In some implementations, the efficient multiscale computational model is created based on the development of specific optimal stimulation patterns related to theta-bursts triggered by subthreshold spike-LFP activity. In some instances, the use of the multiscale computation model in stimulation restores specific memories in normal rodents, TBI rodents, non-human primates, and human clinical patients with memory impairments.

Figure 9:
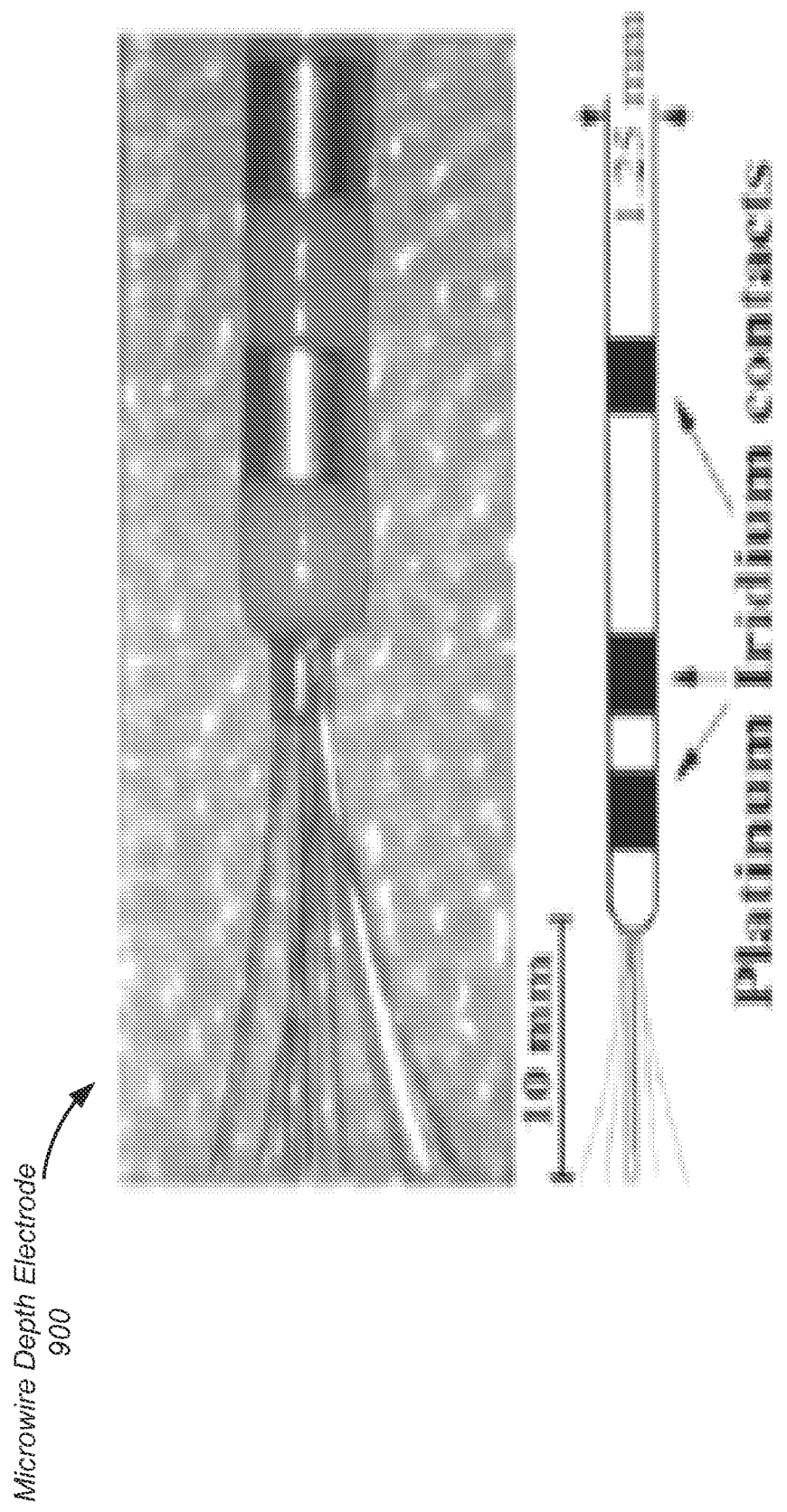
FIG. 9 illustrates an exemplary microwire depth electrode, in accordance with some implementations.

In some implementations, FDA-approved technology (e.g., Neuropace RNS®) is utilized to assist development of a computational model and/or application of the computational model to restore memory in human clinical patients. For example, in some implementations, the NeuroPace RNS® System Neurostimulator and Leads (the "RNS device") is implanted in epilepsy patients and monitored at least initially with depth electrodes fashioned with microwires (e.g., Behnke-Fried depth electrodes, microwire depth electrodes 900, FIG. 9). Consequently, in some implementations, the immediate analysis of single neuron and/or LFP recordings in conjunction with stimulation of memory is followed by long-term (e.g., 6 months, 1 year, 18 months, etc.) task-related episodic stimulation using the RNS device. This aids in characterization of complex neurophysiological signals within the HEC system in response to long-term stimulation for memory. In some implementations, the data gained through long-term stimulation is used to refine the computational model for precise enhancement of memory.

In some implementations, the computational model is incorporated into a device (e.g., the Medtronic Activa PC+S device) to restore memory in TBI patients with memory impairments. In some implementations, optimized model parameters (e.g., theta-bursting of high-frequency patterns) are utilized with on-demand synchronization of stimulation with external systems through wireless telemetry to allow for: (1) task-dependent stimulation; (2) integration of critical safety features; and (3) a flexible algorithm-programming structure to generate closed loop concepts. For example, by using underthreshold hippocampal theta-gamma coupling activity to trigger stimulation onset. Together, these features provide an unprecedented window into neural network responses of memory formation and recollection, leading to therapy optimization through algorithms.

Figure 2:
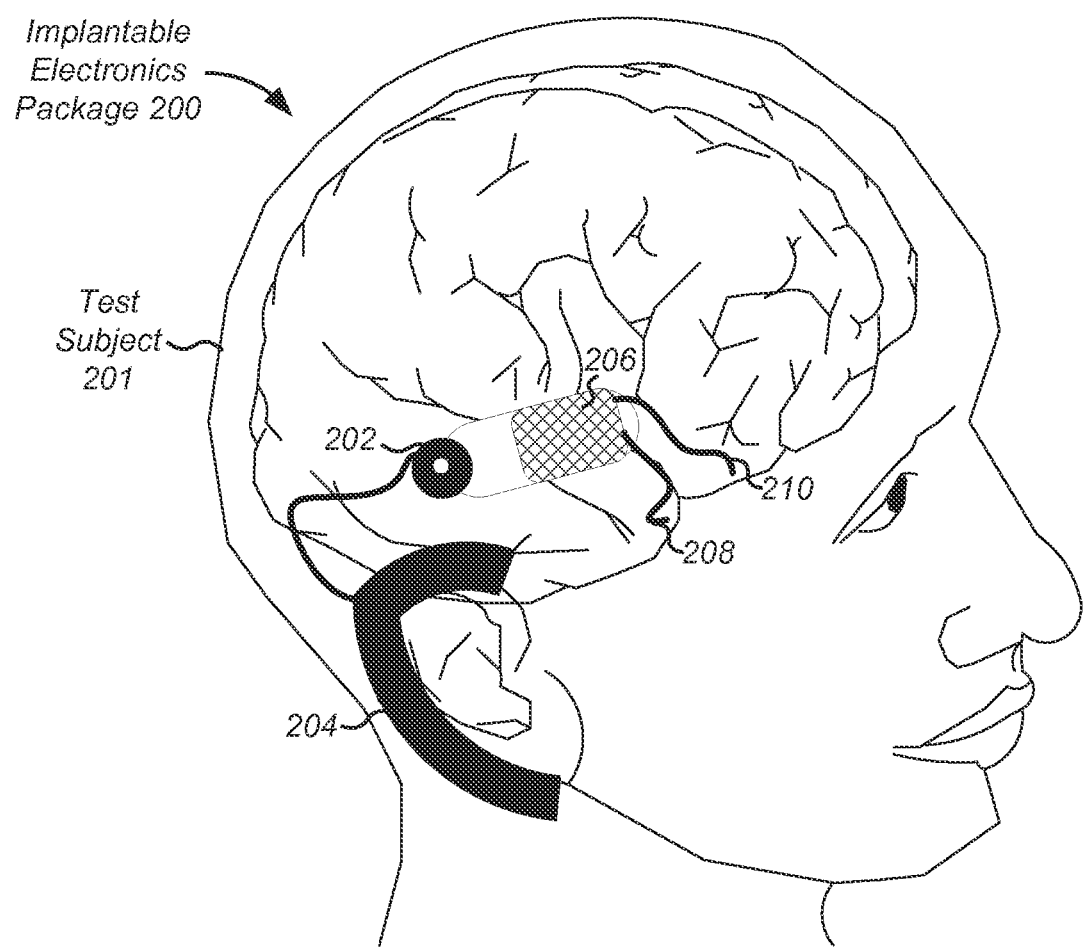
FIG. 2 illustrates an exemplary implantable electronics package, in accordance with some implementations.

FIG. 2 illustrates implantable electronics package 200 (also sometimes called a "wireless implant") implanted in a test subject 201, in accordance with some implementations. In accordance with some implementations, implantable electronics package 200 includes one or more coaxial external primary RF coils 202, an electronics module 206, a first sub-cortical probe 208, and a second sub-cortical probe 210.

The one or more coaxial external primary RF coils 202 couple the electronics package 200 to an external wearable electronic system 204 (also sometimes called an "earpiece module" or "external earpiece"). In some implementations, the electronics package 200 further includes one or more secondary coaxial RF coils (not shown) for power and data telemetry. In some implementations, the electronics module 206 is hermetically packaged and battery-less. In some implementations, the electronics module 206 provides stimulation to the test subject and records at least a subset of the results. In some implementations, the electronics module 206 includes the stimulation module 150 (FIG. 1) and/or the feedback collection module 110 (FIG. 1). In some implementations, the first sub-cortical probe 208 includes a plurality of electrodes (e.g., 32 electrodes). In some implementations, the first sub-cortical probe 208 is implanted in the entorhinal cortex of the test subject 201. In some implementations, the second sub-cortical probe 210 includes a number electrodes that is the same as the number of electrodes in the first sub-cortical probe, while in other implementations the second sub-cortical probe includes a distinct number of electrodes. In some implementations, the second sub-cortical probe 210 is implanted in the hippocampus of the test subject 201.

In some implementations, the implantable electronics package 200 and the external wearable electronics system 204 are components of a neuromodulation system such as computing system 100, FIG. 1.

Some implementations disclosed herein provide a safe and state-of-the-art miniature, wireless, chronically implantable neuromodulation system that incorporates both single-neuron and LFP recordings into a closed-loop system that is chronically implanted in human TBI patients. In some implementations, this system enables stimulation and recording from 64 channels located on a pair of high-density sub-cortical electrode arrays (e.g., probes 208 and 210, FIG. 2). The arrays connect to a skull-mounted implantable electronics package capable of wireless data and power telemetry. An external electronic system (e.g., worn around the ear), such as external wearable electronic system 204 in FIG. 2, embeds the memory model and provides power telemetry to the implantable package using an RF-coil system. The disclosed implantable wireless systems offer unmatched capabilities in spatiotemporal resolution, robustness, and size, as shown in Table 1 below.

TABLE 1 device features for various devices used in accordance with some implementations

| Device/ Features | Number of Channels | Electrode Spacing | Battery on the implant | Single-unit + LFP sensing | Location | Concurrent R + S | Volume |
|---|---|---|---|---|---|---|---|
| Device 1 | 2 × 4 | 3.5 mm | Yes (705 mAh) | No | Cranial | No | 13 cm$\hat{\,}$3 |
| Device 2 | 2 × 4 | 2.8 mm | Yes (6.3 Ah) | No | Chest | No | 39 cm$\hat{\,}$3 |
| Device 3 | 2 × 32 | 0.3 mm | No (wireless) | Yes | Cranial | Yes | <1 cm$\hat{\,}$3 |

Table 1, above, shows various devices used in accordance with some implementations. Device 1 corresponds to the RNS device described above. Device 2 corresponds to a Medtronic Activa PC+S device. Device 3 corresponds to an implantable neuromodulation system, such as the implantable electronics package 200 (FIG. 2), disclosed herein.

Chronic recording of neural activity can be a challenge, primarily due to delamination of polymer-polymer interfaces and subsequent corrosion and shorting of traces and electrodes. To enhance longevity of stimulating and electrophysiological devices, an interface-free microelectrode array is utilized in some implementations. In some implementations, the interface-free microelectrode array uses FDA-approved biocompatible materials. In some implementations, the interface-free microelectrode array includes encapsulated thin-film metal scaffold traces and electrodes to eliminate all seams and increase electrode lifetime. In some implementations, the probes are configured with high-density platinum electrodes that demonstrate long-lifetime due to minimal corrosion.

Figure 3B:
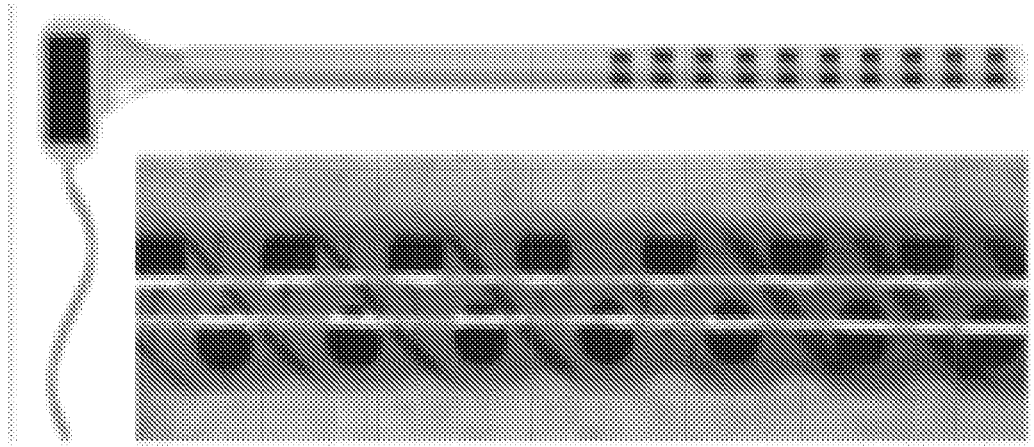

FIGS. 3A-3B illustrate exemplary sub-cortical electrode arrays (also sometimes called an "electrode array," a "neural probe," or a "sub-cortical neural probe"), in accordance with some implementations. FIG. 3A illustrates sub-cortical electrode array 302, in accordance with some implementations. The sub-cortical electrode array 302 includes a plurality of electrodes 304 wound around a depth electrode 306. In some implementations, the sub-cortical electrode array 302 is fabricated for human implantation. In some implementations, the electrodes 304 comprise a thin-film electrode array. In some implementations, electrode array includes 64 electrodes 304 coupled to 64 channels capable of stimulation and/or recording. In some implementations, the thin-film electrode array is designed to for long-term implanted in a test subject (e.g., greater than 5 years). In some implementations, a first portion of the electrodes 304 is used for LFPs and a second portion of the electrodes is used for single neurons. In some implementations, the first portion includes half of the channels and the second portion includes the other half of the channels.

Some implementations include a method for spiral winding of a polymer electrode array around a DBS-style lead stylet for surgical implantation, and in-vitro characterization of surgical implantation precision. In some implementations, the method further includes biocompatibility testing of the electrode arrays (e.g., ISO10993 biocompatibility testing).

FIG. 4 illustrates hermetically-packaged battery-less electronics 402, in accordance with some implementations. In some implementations, the hermetically-packaged battery-less electronics 402 include high-density interconnects and 3-D integration. In some implementations, the hermetically-packaged battery-less electronics 402 comprise an implantable electronics package such as implantable electronics package 200, FIG. 2. In some implementations, the hermetically-packaged battery-less electronics 402 include a chronically biocompatible electronics package. In some implementations, the chronically biocompatible electronics package is a skull-mounted electronics package (e.g., implantable electronics package 200, FIG. 2). In some implementations, the chronically biocompatible electronics package is an external electronics system (e.g., external wearable electronic system 204, FIG. 2). In some implementations, the electronics packages (e.g., implantable electronics package 200, FIG. 2) includes one or more of: (1) ultra-high density feedthroughs enabled by a pitch extruded via process; (2) 3-D integrated electronics for extreme miniaturization and integration with passive components; and (3) rivet-bonded flex-to-ceramic bonds to enable miniaturization of interconnects between electrode arrays and the electronics module (e.g., electronics module 206, FIG. 2). In some instances, the high-density packages are a key component for compact, biocompatible packages that can be mounted on the skull.

One of the major challenges in the development of closed-loop neuromodulation systems is the recording of tiny (e.g., ~100 μV) neural signal activity in the presence of the large (e.g., ~100 mV) stimulation artifact. The large stimulation artifact tends to saturate the analog front end in conventional implementations.

Instead of the conventional voltage/current-domain amplification, some implementations include front-end circuits that rely on voltage-to-phase amplification. A circuit that operates in the unbounded phase-domain is inherently robust to saturation. In accordance with some implementations, a multi-bit VCO-ADC (e.g., 16-bit) is utilized to handle large signals (e.g., 200 mV) and provide a small step-size (e.g., 1 μV) for the signals of interest. With an unsaturated output from the analog signal chain, in some implementations, sophisticated adaptive filters are used to remove the stimulation artifact.

To enable recording of single units from multiple channels (e.g., 64 channels), in an inductively-powered implant, the low-noise amplifiers must use reduced power. The disclosed implementations include an approach of using Frequency-Division-Multiplexing ("FDM") to share the most power-hungry blocks of the amplifier, while maintaining the same noise. Thus for a given noise specification, multiple (e.g., 3-5) channels are amplified with the same power consumption as a single-channel amplifier. Since this voltage amplifier is vulnerable to saturation in the presence of stimulation artifacts, in some implementations, an auxiliary path is enabled when a stimulation pulse is applied. The auxiliary path uses the VCO-ADC based front-end which has higher power consumption (e.g., ~15 μW/channel), but does not saturate. Such an implementation consumes very low power and at the same time be robust to stimulation artifacts. In order to support single-unit recordings without exceeding the available data rate (e.g., 1 Mbps), a hardware-efficient feature extraction algorithm is implemented to reduce the data rate (e.g., by a factor of 10).

Figure 5:
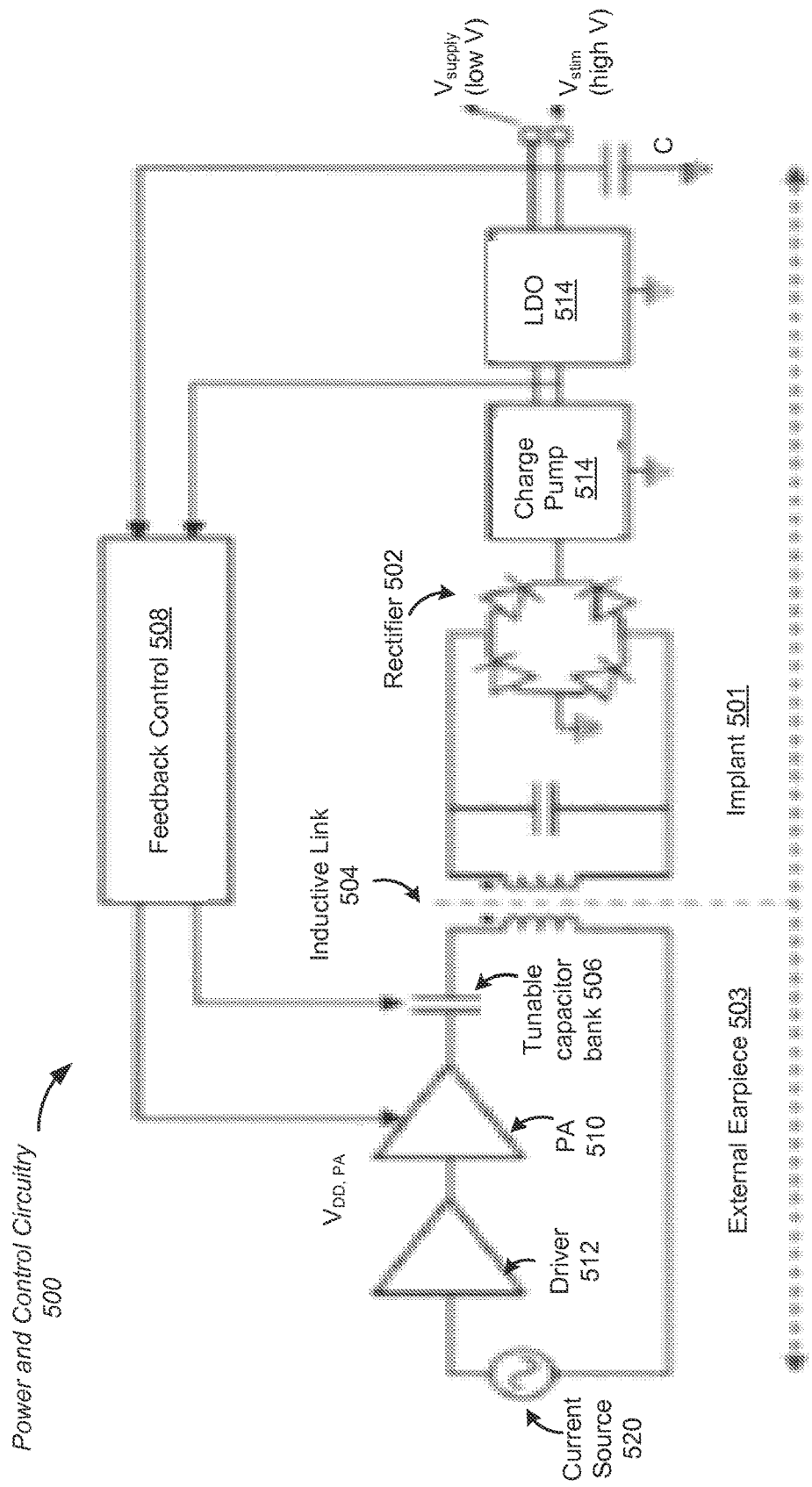
FIG. 5 illustrates exemplary power and control circuitry for use with a wireless implant, in accordance with some implementations.

FIG. 5 illustrates power and control circuitry 500 for use with wireless implant 501, in accordance with some implementations. In some implementations, wireless implant 501 is an implantable electronics package such as implantable electronics package 200, FIG. 2. Power and control circuitry 500 includes an inductive power supply system. In some implementations, the power and control circuitry 500 includes, at the wireless implant 501, a pair of near-field coils to create inductive link 504, an active rectifier 502, a plurality (e.g., 2-4) of local low drop-out regulators ("LDOs") 515, a high-voltage charge-pump circuit 514, and feedback control 508 (or a portion thereof). In some implementations, the power and control circuitry 500 includes, at the external earpiece 503, a driver 512, a power amplifier ("PA") 510, a tunable capacitor bank 506, and feedback control 508 (or a portion thereof).

In some implementations, the rectifier 502 includes a fully on-chip dynamic compensated topology to enhance the power efficiency. In some implementations, a multi-LDO topology is adopted to optimize the LDO performance and isolate analog/digital components. In some implementations, the stimulation circuitry is based on a digitally controlled current DAC that behaves like a current source. In some implementations, an additional circuit neutralizes any excess charge on the electrode after stimulation to prevent long-term damage due to electrode oxidation/reduction. In some instances, the worst-case peak required power at the implant during stimulation is around 10 mW, with a peak-to-average ratio of approximately 10. In some implementations, in order to reduce the peak power in the wireless link 501, a local bypass is added on the implant package to deliver the spike current. In some implementations, the implant 501 further includes several small capacitors (e.g., 1 μF capacitors). With this storage, the wireless link needs only to deliver 1 mW average power to the implant, translating to a compliant and more efficient overall design.

In some implementations, an embedded processor inside the earpiece module (e.g., external earpiece 503) hosts adaptive filters for artifact removal, programmable memory model and a system/interface controller.

In some implementations, the external earpiece 503 and implant 501 are components of a neuromodulation system such as computing system 100, FIG. 1. In some implementations, the neuromodulation system is tested in rodents, TBI rodents, and non-human primates, before being used to restore memory in TBI patients (e.g., in a clinical trial). In some implementations, the testing includes both in-vivo tetrode recording and whole cell recording in rodents. In some implementations, the testing includes the use of a multi-sensory and multi-modal virtual reality system for rodents that can be easily generalized to humans for cross-species model validation.

Figure 6:
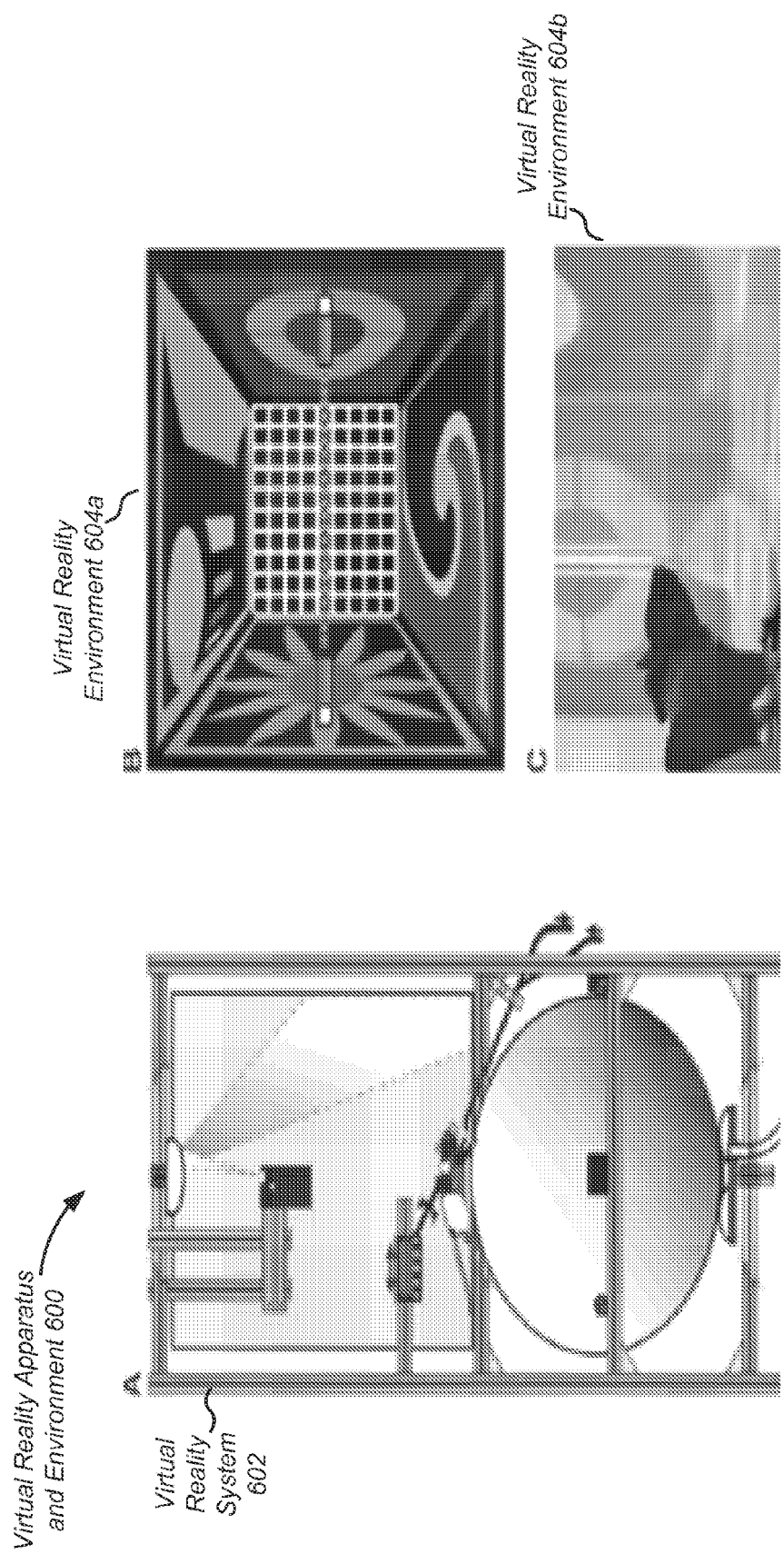
FIG. 6 illustrates an exemplary virtual reality apparatus and environment, in accordance with some implementations.

FIG. 6 illustrates virtual reality apparatus and environment 600, in accordance with some implementations. FIG. 6(a) shows a schematic of a virtual reality system 602 including a reward delivery tube, hinged and adjustable harness, spherical treadmill, micro-projector, distortion mirror, and cylindrical projection screen. FIG. 6(b) shows a top-down view of the virtual reality environment 604a. The virtual reality environment 604a includes a linear track (e.g., 2.2 meters) in the center of a room (e.g., a 3×3 meter room). The virtual reality environment 604a also includes a variety of distal visual cues on each wall and, in some implementations, active reward locations indicated by the pillars in FIG. 6(b). FIG. 6(c) shows a rat in a virtual reality environment 604b.

In some implementations, the virtual reality system is used to bridge the gap between two important forms of learning: declarative and associative, by simultaneously measuring navigation and associative learning. Thus this unique combination of multi-scale computational theory, neural ensemble recording from the HEC system in behaving rodents and novel hardware development of multisensory virtual reality is unparalleled and allows for rapid progress in testing and refinement. In some implementations, a GRIN lens is included for visualization of the activity of large populations of hippocampal neurons in-vivo. The use of the GRIN lens combined with stimulation and spike-LFP recordings in healthy rodents significantly enhances understanding of hippocampal-entorhinal function. In some implementations, the behavioral tasks used to measure a neuromodulation system's ability to restore memory are also tested with rodent TBI models.

In some implementations, data from three rodent models of TBI (fluid percussion, cortical impact, closed head injury) are utilized to train the neuromodulation system and/or adjust the virtual reality system.

In some implementations, the testing of the neuromodulation system includes testing in non-human primates. Non-human primate research sits at the interface of neuropsychology and primate neurophysiology. The neural recording performed is usually guided by concepts from human psychology with the aim of finding the neural mechanisms that explain established cognitive behaviors. In addition, research in non-human primates improves understanding as to how the brain supports learning and memory; guides eye movements and the allocation of visual attention with extensive expertise in the training of awake behaving primates to perform cognitive tasks; in eye movement tracking and in both electrophysiological recording and stimulation. In some implementations, the testing of the neuromodulation system includes clinical trials for restoration of memory in TBI patients.

In some implementations, the functionality of the neuromodulation system is based on the neural code transforming percepts into distinct memories, which are later available for conscious retrieval, and is thus the basis for declarative memory. This unique code is specific yet invariant, conscious, relatively late (e.g., ~400 msec), sparse, associative and abstract.

In some implementations, single-neuron and LFP recordings are continued with greater spatial and temporal resolution, and stimulation of the entorhinal-hippocampal axis in the same subjects. The ability to access single cells in the human MTL for combined electrophysiological and cognitive studies presents significant novelty because the primary focus in many other laboratories continues to be on functional neuro-imaging in humans and single-unit recording in animals; even the few studies of invasive human neurophysiology of the MTL are mostly based on intracranial EEG and none of micro-stimulation of the MTL. In some implementations, macro- and micro-stimulations are combined with simultaneous single unit and LFP neurophysiology all performed in the same subjects in a unique clinical setting enabling access to the MTL in awake conscious human subjects who are able to declare their thoughts, recollections and experiences. This is a rare situation with almost no parallel in modern day neuroscience. In addition, the neuro-computational discovery of sequence memory trace in the hippocampus is widely recognized as the best evidence for spike timing-dependent plasticity ("STDP") during behavior and is often called the "Mehta effect."

Memory, especially of facts and events, (e.g., declarative memory) arises in the Hippocampal-Entorhinal-Cortical system. However, the computational mechanisms by which this happens and the experimental tests of those models have been lacking, resulting in the absence of viable treatments for memory disorders. The primary reasons for this crucial gap in our knowledge are twofold. First, most theories of memory formation have focused either on the hippocampus alone, or on the cortico-hippocampal interaction, with little attention to the contribution of the entorhinal cortex. Second, experimental techniques to measure entorhinal contributions to HEC circuit dynamics and to memory performance in complex behavioral tasks has not been measured.

The computational models disclosed herein are biophysical yet span the entire range from molecules to synapses to cells to groups of networks and behavior, and more importantly, the models have been validated experimentally. For example, a simple hippocampal network of CA3-CA1 neurons can learn temporal sequences of events. In particular a key function of the hippocampal circuit is to anticipate or predict future events based on the statistical regularities of past events.

In some implementations, the computational model is tested using in-vivo single-unit electrophysiology from CA1. The precise spike-timing required for STDP induction does not occur naturally during behavior because neural responses are Poisson distributed (high coefficient of variability) but the problem can be solved by neural oscillations. In some implementations, a model of generating precise spike-timing for STDP via neural rhythms is used. In some implementations, a network model is used to show slow-wave sleep rhythm arises, when memory consolidation for long periods (several days) occurs.

The entorhinal neurons show strong spatial selectivity. In fact, entorhinal neurons, sometimes called grid cells, show spatially periodic firing. Further, the entorhinal inputs on the distal dendrites are more likely to generate a dendritic spike, which would be very effective in eliciting a somatic spike. This raises three important computational questions about memory formation: (1) What factors determine the activity patterns of entorhinal cortical neurons in vivo? (2) How is entorhinal and CA2 inputs combined in a precisely timed fashion to drive CA1 neurons' activity? (3) How do these processes contribute to HEC memory formation and how can that be improved or fixed if damaged? In an anesthetized or sleeping animal, the entorhinal neurons show spontaneously occurring, stochastic memory-like activity lasting anywhere from one second to two hundred seconds. Further, this memory-like activity occurs about 90% of the time during sleep and could be detected using only simultaneous measurement of all parts of the HEC circuit. This spontaneous entorhinal memory is able to robustly drive hippocampal neural activity, which directly negates previous belief that the entorhinal neurons would be incapable of driving hippocampus. In some implementations, multiscale computational models of the mechanisms that determine the generation of this spontaneous memory in the entorhinal cortex are used and refined. The electrophysiological measurements provide a sub-millisecond accurate resolution activity map of many neurons. However, this cannot provide information about the anatomical identity and localization of neurons.

In some implementations, a GRIN lens based imaging system is used to image the activities of large populations of anatomically identified neurons during the same tasks as electrophysiology measurement. The dual approach of using electrophysiology and imaging to obtain both anatomical specificity and precise timing of activity reveals the techniques by which a spontaneous memory can be enhanced using patterned electrical stimulation. In some implementations, a computational model of how activity is dynamically coordinated between entorhinal, CA3 and CA1 neurons, and this circuit facilitates the propagation of spontaneous memory. Due to the otherwise dissipative nature of dendritic potentials, it is necessary for the inputs from these different regions to arrive in a synchronous fashion such that this activity is dynamically coordinated to allow different parts of the circuit to selectively drive the other parts. In some implementations, the amplitude-phase cross-frequency coupling ("CFC") between theta and gamma oscillations is used to accomplish this task. In humans, DBS of the entorhinal area results in memory enhancement and phase resetting of the hippocampal theta oscillation. Entorhinal stimulation results in increased theta-gamma CFC. In rodents, CA1 network dynamics shows a strong speed-dependent modulation of the theta-gamma amplitude-phase CFC. In some implementations, a computational model of how theta-gamma CFC differentially helps drive hippocampal subfields CA1 versus CA3 is used.

There is also considerable interest in the relationship between the phase of theta oscillations and the timing of single neuronal spiking both in rodents and humans. Human intracranial studies have shown that the spiking rate of single hippocampal neurons predicts whether a recently learned item will be remembered. It has been hypothesized that the theta-spiking relationship may reflect the cued recall of an upcoming item stored in memory. A recent study in humans showed that the relationship between spiking and theta during encoding predicted memory success. These results implicate a direct role for theta-linked spiking activity in declarative memory. Simultaneous LFP and single neuron recordings link potential mechanisms by which the theta and gamma oscillations together with single neuron activity support successful declarative memory. In some implementations, external stimulation, single neurons, and oscillatory activity work together to support the successful encoding and recall of individual memories or long sequences of memories is determined. In some implementations, the computational model is simultaneously tested in rodents and human epilepsy patients implanted with depth electrodes for stimulation single neuron-LFP recordings.

In some implementations, the closed loop LFP-stimulation aspect of the model is tested for long-term efficacy in the same epilepsy patients using the FDA-approved NeuroPace RNS device and in TBI patients using an FDA-approved Medtronic Activa PC+S device. High-resolution CT imaging and high-resolution magnetic resonance imaging of human hippocampal subfields and diffusion tensor imaging of the human entorhinal perforant pathway aid in bridging the spatial resolution gap across rodents and humans.

In some implementations, several advanced behavioral paradigms are utilized to test the effects of the computational model on specific aspects of declarative memory restoration. For instance, in some implementations, to test spatial versus item-specific components of declarative memory the model is separately tested on the medial entorhinal versus the lateral entorhinal cortical inputs into the hippocampus. In some implementations, using virtual reality in rodents and humans, memory performance on object-object and object-location associations within a learned virtual environment are measured. This task tests complex declarative memories and memory sequence formation defined by auditory and visual stimuli, objects and places, and reward expectancy. In some implementations, recall of separate categories of learned information, including objects, faces, animals, and places is tested using randomized recognition tasks in humans and non-human primates ("NHP"). In some implementations, the learning and recall of associations between items is also tested, as well as between items (e.g., faces or objects) and spatial locations.

In some implementations, to test the commonality of the computational model across individuals, a developed model from one individual is used to restore memory in another individual during separate and multiple experimental settings. In some implementations, the developed model is tested in a closed-loop fashion for declarative memory enhancement in epilepsy patients implanted with hippocampal-entorhinal depth electrodes for stimulation and spike-LFP recordings.

In some implementations, existing commercially available DBS technology (e.g., NeuroPace RNS and Medtronic Activa PC+S) is used in order to test the computational model in human epilepsy and TBI patients. In some implementations, the computational model incorporates entorhinal stimulation triggered at the onsets of under-threshold hippocampal spike-theta-gamma cross frequency coupling to close the loop. In some implementations, the stimulation leverages previous findings that illustrated memory enhancement in humans.

In some implementations, the developed model is tested in a closed-loop fashion for declarative memory enhancement in human epilepsy patients already implanted with hippocampal-entorhinal depth electrodes for stimulation and spike-LFP recordings. In some implementations, existing commercially available DBS technology is used in order to test the model in human epilepsy and TBI patients. In some implementations, entorhinal stimulation is given at the onsets of under-threshold hippocampal spike-theta-gamma CFC to close the loop. In some implementations, stimulation leverages previous findings that illustrated memory enhancement in humans.

In some implementations, polymer-based probes are tested to determine their suitability for long-term chronically implantable neural interfaces. In some implementations, a chronic neural interface based on a flexible polymer substrate is used. These polymers have much lower elastic modulus (e.g., ~3 GPa) compared to state-of-the-art silicon (e.g., ~200 GPa) or microwire devices (e.g., ~100 GPa) and a much lower foreign-body response. The polymer-based neural probe has been successfully implanted in animals for 6 months without eliciting any adverse tissue response.

Some implementations include the development, regulatory approval, and use of an entorhinal-hippocampus cognitive prosthesis. Some implementations include the use of technologies for multi-channel probes, cables, and feedthroughs interfaced with an IPG suitable for clinical use. In some implementations, two ISO tests are performed: (1) ISO 10933 to validate the electrode array/cable biocompatibility at a certified facility and (2) ISO 14708 to validate the array/IPG assembly. The ISO tests provide a base for chronic implant certification.

Figure 7:
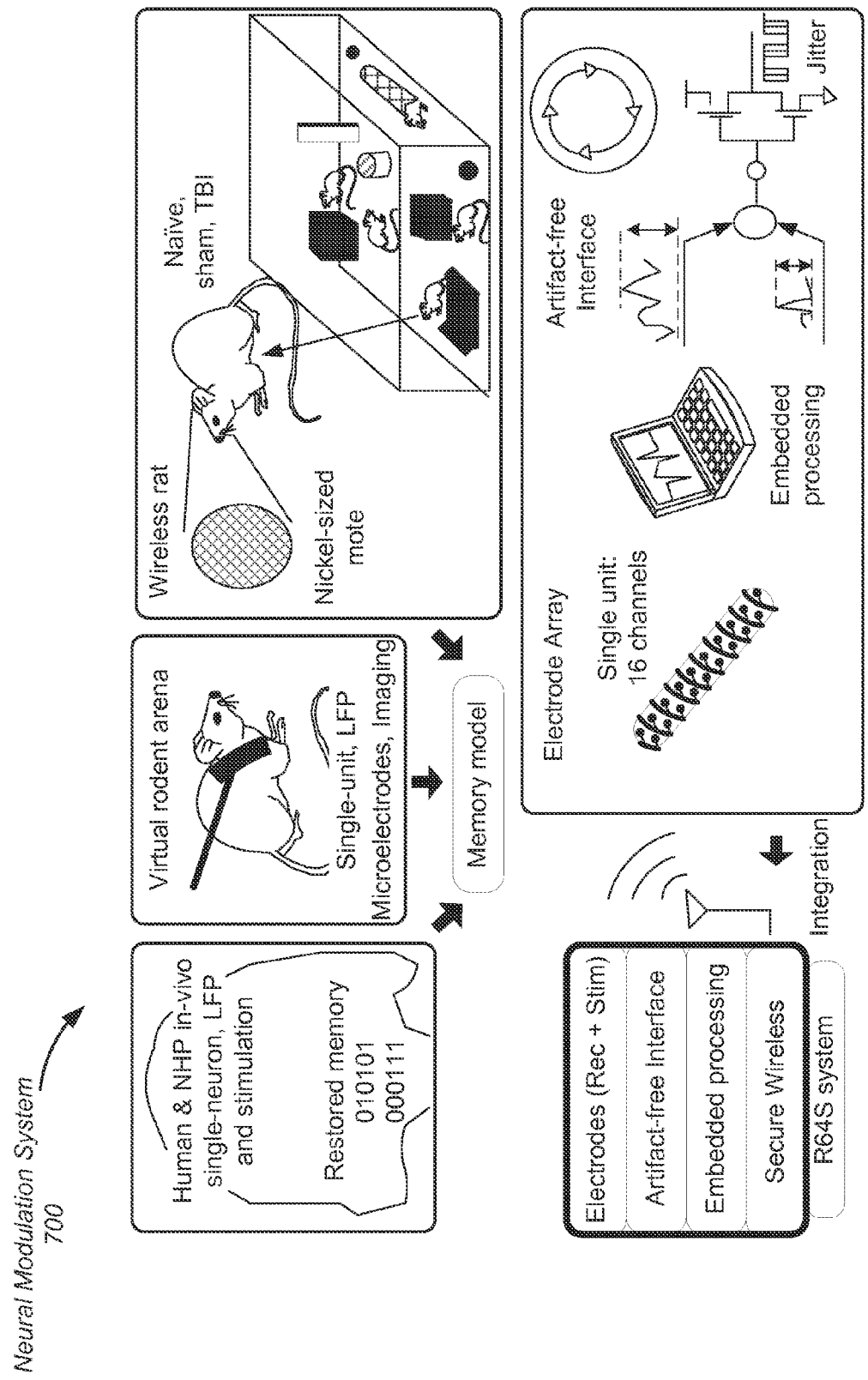
FIG. 7 illustrates a system for developing, fabricating, testing, and validating a device programmed to mitigate neural dysfunction in the injured brain, in accordance with some implementations.

FIG. 7 illustrates neural modulation system 700, in accordance with some implementations. Neural modulation system 700 is a system for developing, fabricating, testing, and validating a device programmed to mitigate neural dysfunction in the injured brain, in accordance with some implementations. In some implementations, a miniature wireless device (e.g., less than 5 g, including battery) is used to record hippocampal activity in freely moving rodents. In some implementations, a 4-channel device is used to simultaneously monitor up to 6 animals (sham, nave, TBI) and obtain indispensable quantitative data of memory encoding following brain injury. In some implementations, this device is further adapted to include stimulation capability that meets the criteria outlined above. In some implementations, additional features are embedded on the device, consistent with the needs dictated by the modeling discussed above. In some implementations, a combination of discrete and integrated components is used for animal tests.

An important feature that is unavailable in commercial devices is an artifact-rejection that allows simultaneous recording and stimulation. Artifacts could introduce interferers that are 100-1000× larger than desired signal. Unlike voltage or current the phase of an electrical signal is not bounded to finite values. In some implementations, saturation tolerance is provided by using phase-domain VCO-ADCs to directly digitize the input signal of interest with a 16-bit resolution, achieving a 200 mVpp saturation-free input range, with a uV-level resolution for the signal of interest. For example, see the discussion regarding FIG. 5 above. Having a non-saturated output even under the presence of large stimulation artifacts makes it possible to perform sophisticated post-processing to remove the stimulation artifacts. In some implementations, adaptive echo-cancellation techniques are used to cancel the effect of the stimulation on the recorded signal. Because the stimulation artifact affects multiple recording channels at the same time, in some implementations, the information contained in the cross-correlation between various channels is used to enhance the efficiency of artifact cancellation.

A closed-loop neural recording systems offers support for real-time spikes sorting. Some implementations include a methodology to evaluate the complexity-accuracy tradeoffs of various spike-sorting algorithms across a wide SNR range. Some implementations include energy-efficient choices for implementing the complexity accuracy optimal algorithms and the use of a 64-channel spike-sorting chip with a low power consumption (e.g., ~130 µW). In some implementations, a flexible spike-sorting processor is used to efficiently support a variety of spike detection and feature-extraction algorithms.

For action potential recording, the front-end low-noise-amplifier consumes a significant fraction of the system power. In some implementations, to reduce the amplifier power, a multi-channel front-end amplifier that shares the most power-hungry blocks between channels is used (e.g., FDM Amplifier, FIG. 8). The bias current used to achieve the input-referred noise requirement (e.g., 4 µVrms) for action potential recording results in the amplifier having an intrinsic bandwidth much greater than the signal bandwidth. In some implementations, Frequency-Division-Multiplex-ing is used to accommodate multiple signals, thus sharing the amplifier across multiple channels.

In some implementations, the stimulation circuitry includes a current-steering DAC with programmable driving/sink currents up to 2 mA (e.g., current source 520, FIG. 5). To support the large output swings (e.g., greater than 5V), in some implementations charge-pumps are used to generate the large supply and bias voltages that are used in the DAC. In some implementations, a charge-balancing circuit is used to neutralize any excess charge on the electrode after a stimulation event, which could otherwise lead to tissue damage.

Power delivery is important design consideration for an implantable system. In some implementations, for system integration, a high-voltage-generator (part of a stimulator block) with adaptive loading in a standard process is used in order to avoid the use of high-voltage transistors. To adapt to a wide range of loading impedances between the electrode and the brain tissue, the high-voltage generator is designed in some implementations to supply a variable voltage (e.g., −10V, up to 10V) for the output drivers. In some implementations, a novel, bidirectional, switched capacitor output stage that combines both voltage conversion and pulse drive is used. In some implementations, in the active rectifier (e.g., rectifier 502, FIG. 5), a fully on-chip dynamic compensated topology is employed to enhance the power efficiency.

In order to close the loop between recording and stimulation, a portable processor that turns recorded neural data into an effective stimulation pattern is used in some implementations. The processing, as guided by the memory model, is integrated in a low-power embedded device.

In some implementations, the processor is specific to the domain on neural computations, however it has adequate flexibility to vary model parameters as required. Thus, close interaction with modeling yields a successful integration of the embedded low-power processor.

Some implementations include a fully unsupervised neural spike sorting processor, which consumes low power (e.g., less than 5 µW/channel). In some implementations, methods for algorithm analysis, complexity-accuracy tradeoffs in particular, are used to develop hardware-aware algorithms and their chip implementation, optimized for low power.

Some implementations include the use of a high-density microelectronics package with interconnect system for a fully-integrated neural interface. In some implementations, the package consists of three major components: (1) a high-density ceramic feedthrough array to connect the wireless recording electronics to the microelectrode array, (2) a bio-compatible metal shell, and (3) electronic components (e.g., stimulating and recording chips, wireless telemetry, and passive components). To achieve extreme miniaturization, some implementations utilize advanced 3-D packaging technologies (such as flip-chip bonding, wire-bonding, stencil printing, and brazing) to directly assemble ICs and passive components in a small form-factor. In some implementations, the flexible microelectrode array with stimulating and recording sites is attached to the package using high-density interconnects of conductive polymers.

A classic test of complex declarative memory is the Morris Water maze task. However, it is rather difficult to do electrophysiology during this swim task. Besides, this task is aversive, involving escape to a platform, whereas a majority of memory tasks we undertake are appetitive, carried out to obtain food, water or other rewards. In some implementations, a non-invasive virtual reality system that is also multisensory and multimodal is used for testing rodents (e.g., the virtual reality apparatus and environment 600, FIG.

6). In this multisensory virtual reality system rats have to remember to go to an unmarked spatial location, defined by distal audio-visual cues, to obtain sugar reward. While most research has focused on uni-modal behavioral measures, such as navigational accuracy, to understand complex behavior it is necessary to have multimodal behavioral assay and relate it to neural activity pattern. Hence, some implementations include simultaneously measuring navigational memory, defined by multisensory stimuli, along with associative memory in this multimodal virtual reality in both rodents and human epilepsy patients.

Reliable electrophysiology is performed using this virtual maze. In the virtual maze, place cells behave like distance cells, which is a much more complex pattern of activity than seen in the real world. In the virtual world the frequency of neural rhythms can be dissociated from their temporal coding properties. In some implementations, the contribution of these distance coding neurons to multisensory and multimodal memory formation is measured. In some implementations, the neural dynamics are simultaneously measured from the entorhinal cortex, CA3 and CA1. In some implementations, the precise coordination between these regions within single cycles of gamma oscillation is used to determine how these interact to generate a robust memory trace in this circuit.

As discussed above, there are a few FDA-approved, commercially-available, human implantable systems for neural stimulation and recording, including systems from Medtronic and Neuropace. Both are Deep Brain Stimulation systems, capable of stimulating and recording from multiple contacts to treat motor disorders and epilepsy.

Despite the decades-long use of DBS therapy and the increasing list of disorders to which it can be applied, the mechanism by which DBS effectively works is still largely unknown. To improve understanding and treatment, new technologies with the ability to record and stimulate simultaneously from a greater number of channels from multiple regions of the brain are required. The current disclosure includes the use of several new technologies, such as: (1) implantable arrays with a high-channel count, suitable for both stimulation and recording; (2) stimulating and recording electronics capable of interfacing with the high-channel arrays; (3) wireless data processing unit capable of programmable neuromodulation on large numbers of channels; and (4) a power source for the high-channel data processing and stimulating/recording electronics.

For sub-cortical stimulation and recording, silicon-based neural interfaces are often employed. Several notable silicon-based neural interfaces (e.g., Blackrock Microsystems, Neuronexus) have been used over the last two decades. Despite some medium-term success of various types of penetrating arrays, no method has been successful at demonstrating a long-term functional neural interface from these silicon neural interfaces.

The electrode failure is often attributed to mechanical mismatch between the rigid device material and cortical tissue as well as the persistence of a foreign body in the neural tissue. Most of the conventional analog front-ends saturate in presence of a few mV of artifacts and prohibit simultaneous recording and stimulation. Previous efforts to enable simultaneous recording and stimulation attempted to prevent the saturation of the signal chain by introducing a parallel shunt impedance to discharge the electrode after the stimulation. This method reduces the dead-time following stimulation, but a dead time of around 10 ms still exists. The problem of saturation by interferes is a generic problem for biosignal recording. Some attempts to reduce the dead time following a large motion artifact have been made by resetting the analog front-end. Some attempts have been made to remove motion artifact by an ICA-based feedback loop. However, most of these techniques still suffer from either a recording dead time or a very limited input range.

State-of-the-art action potential recording amplifiers have the same fundamental architecture of a differential amplifier used with feedback. The input-referred noise is limited to the noise of the input devices of the differential pair. The minimum bias current in the amplifier, which is set according to the required noise performance, results in the amplifier bandwidth being much larger than the signal bandwidth. These conventional designs have a theoretical minimum Noise-Efficiency-Factor ("NEF") of 2, which corresponds to the NEF of a differential pair. This architecture has reached its limit in terms of reducing power, and new approaches need to be adopted for the power to be reduced further.

Previous designs of high voltage generators required for stimulation drivers are usually based on efficient but bulky DC-DC converters. Despite high efficiency, a DC-DC converter is not suitable for applications with very limited space, because it requires several off-chip components. Also, generating high voltages by using high-voltage transistors can decrease power efficiency. Instead of active adaptive rectifier, some of previous solutions replace off-chip diodes with an on-chip active transistor.

The current disclosure has several advantages over current technologies. In some implementations, for chronically implantable neural probes, high channel count polymer-based arrays are employed for longterm stability. These polymers have lower foreign body response compared to silicon or microwire devices. In addition, in some implementations, high-density miniaturized packages are used, which provide for compact electronic systems that can be embedded using less invasive surgical techniques. Moreover, the disclosed implantable device (e.g., implantable electronics package 200, FIG. 2) does not require battery. Furthermore, in some implementations, artifacts are removed by moving to phase domain processing, where the signal does not experience physical bounds like in the conventional voltage- or current-based systems. Thus, in some implementations, up to 200 mV stimulation artifacts can be removed, representing a 20× improvement over current technologies. Also, some implementations include use of a frequency-division multiplexing ("FDM") amplifier architecture, which, together with impedance-based filtering, allows several channels to share an amplifier current without increasing input noise. This approach leads to greater than 3× lower amplifier power usage than existing approaches.

Attention is now directed to rodent models of traumatic brain injury.

Fluid percussion injury ("FPI") is a TBI model wherein a fluid pulse is imparted to the intact dura via a craniectomy, creating a general brain movement injury that models elements of single concussion and diffuse axonal injury. The histopathology of this model is well characterized across multiple stages of brain maturation, ranging from small cortical contusions and regional hippocampal neuron loss (CA3 and hilar cells) in adults to no apparent neuronal loss in developing rats. Importantly, even in the absence of histological lesions, in young animals FPI induces a state of impaired excitatory neurotransmission in the hippocampus that is associated with a loss of experience dependent neuroplasticity. This state of impaired hippocampal activation appears to hinge upon alterations in glutamatergic Data shows that impaired NMDAR-mediated EPSCs in hippocampal slices, deficits in working memory using the novel object recognition ("NOR") test and reduced pharmacological activation of rCBF using phMRI.

Controlled cortical impact ("CCI") is an injury model that reproduces pathobiology seen after human TBI including focal hemorrhagic contusions, as well as diffuse axonal injury. In this model, the underlying hippocampus also sustains injury, which includes some cell death. There is also typically a full-thickness cortical contusion that develops an ischemic core and eventually results in focal cortical cavitation, with varying degrees of hippocampal pathology.

Closed head impact ("CHI") or mild TBI ("mTBI") is a newer injury model that mimics mild human TBI (e.g., due to a concussion or blast). Importantly, this model does not require craniectomy and has successfully been used to model repeat mild TBI ("rmTBI") as occurs clinically in sports and military settings. In particular, this model has been studied in adolescent and young adult rats, and results in graded hippocampal memory impairments (novel object recognition) and increasing axonal injury based upon the number and frequency of repeated hits. Little if any hippocampal neuronal death is seen after one or more CHI injuries in young rats. Both developing and mature animals demonstrate deficits in hippocampal function after lateral FPI in the absence of histological lesions or cell death. Hippocampal behavioral dysfunction after FPI or CHI includes non-rule based measures of working memory such as the novel object recognition task. Also, some implementations use impairments in hippocampal-based spatial learning and memory using the Morris Water Maze ("MWM") for both acquisition and probe trials.

The prospect that functionally stimulating the projections to the injured hippocampus to promote plasticity and memory function is supported by intervention studies in young rats after lateral FPI. In this model, as mentioned above, down regulation of hippocampal glutamatergic systems, diminished electrophysiological activation of CA1, impaired working memory, decreased hippocampal activation on phMRI and reduced responsiveness to experience-dependent plasticity in the enriched environment is observed.

In some instances, by using a glutamatergic co-agonist at the NMDAR and combining this with housing in an enriched environment, hippocampal activation and experience-dependent plasticity is restored, manifest as improved MWM performance. Also, using lateral FPI, theta stimulation of medial septal nuclei projections to hippocampus results in improved memory function in the Barnes Maze. In some implementations, memory in TBI rodents is restored and the molecular and neurophysiological changes that occur during this process is characterized.

It is important to ensure that ethical, legal and societal implications are considered in a deep and professional manner. Review of human research implementations including ELSI (ethical legal and societal implications) elements is important. Thus, some implementations include a data and safety monitoring board for objective continuing oversight and participation in the national discussion of brain stimulation and recording.

As discussed above, in some implementations, a computational model of the HEC system that can restore declarative memory in human clinical patients is developed and refined. In some implementations, this involves simulating hippocampal-entorhinal synapses responding to pre- and post-synaptic stimuli of various Fourier patterns. In some implementations, these stimulation patterns are tested in human epilepsy and TBI patients to restore memory. Some implementations include stimulating and recording single unit activity in epilepsy patients implanted with Behnke-Fried microwire depth electrodes (e.g., microwire depth electrode 900, FIG. 9) to develop the computational model and test it, limited by the time-duration of electrode placement in epilepsy patients (e.g., up to 14 days). In some implementations, in patients who meet the indications for placement of RNS system for seizure control, existing FDA approved technology (e.g., the RNS device) is utilized not only to control seizures but also in conjunction with memory tasks to test the long-term effects of stimulation on memory. In these patients, the RNS device determines the human LFP signatures underlying stimulation-induced memory enhancement, thereby providing long-term data necessary for refinement of a computational model. In some implementations, the determined LFP-stimulation component of the model is implemented into existing FDA-approved technology (e.g., Activa PC+S) in order to restore memory in patients with TBI, using the sensing and closed-loop capabilities of the Activa PC+S as well as its power capacity. In some implementations, the additional spike-LFP component of the model derived from simulation and human depth electrode single-unit data as well as the data obtained from use of the RNS and Activa devices is incorporated into a new wireless closed-loop implantable microelectrode device (e.g., implantable electronics package 200, FIG. 2) that is implanted into TBI patients with memory impairments. In some implementations, the ability for this newly developed device to restore specific memories and associations between memories is demonstrated (e.g., for at least 14 days).

As discussed above, some implementations include development a computational model of the HEC complex, declarative, long-term memory system in human clinical patients. In some implementations, a testable computational model of the HEC system that underlies long-term declarative memory in humans is developed. In some implementations, simulation studies of entorhinal-hippocampal synaptic activity concomitant with single neuron and LFP recordings in the HEC system determine precise Fourier and spike-timing stimulation patterns necessary for maximal synaptic potentiation. In some implementations, a testable spike-LFP-stimulation integrated computational model of the hippocampal-entorhinal system is developed that can be used to test long-term memory restoration in humans. In some implementations, a testable computational model of the HEC system underlying long-term memory formation in human clinical patients is developed.

Some implementations include a developed computational model of how spontaneous memory arises in the entorhinal cortex, how it influences HEC interaction, along with testable predictions. Some implementations include a model of how entorhinal spontaneous memory influences learning via spike timing dependent plasticity (STDP) in a network of neurons that is testable using neural stimulation. Some implementations include a testable computational model of how temporal code appropriate for rapid memory formation is generated in a biophysical network of neurons.

In some implementations, the computational model is capable of differentiating between memories that are consequently remembered from those that are forgotten. (2) In some implementations, the computational model is capable of restoring face, place, animal, and object categories, and associations of faces and places in a virtual navigation context. In some implementations, the computational model is capable of explicit recall episodic memory of meeting a person in a place at least two hours after stimulation.

In some implementations, the developed computational model is used to differentiate successful versus unsuccessful memory formation in human epilepsy patients. In some implementations, the developed computational model is used to restore five memory components including face, place, animal, object and faceplace association. In some implementations, the developed computational model is used in recall of episodic person-place association 2 hours following stimulation.

In some implementations, the spike-LFP-stimulation components of the model are tested in epilepsy patients implanted with depth electrode recordings for up to 2 weeks. In some implementations, four memory tasks are used to measure the formation and retrieval of the components mentioned above.

In some implementations, the developed computational model of HEC system can differentiate from specific remembered versus forgotten memories of different types in human clinical patients and restore the five memory components as well as explicit recall two hours after stimulation.

Some implementations include demonstration of the HEC model to distinguish remembered from forgotten items, retrieval of the memory components and explicit recall using recorded neurophysiological signatures including spike frequency and timing and local field potential activity (e.g., theta gamma cross frequency coupling) subacutely in human epilepsy patients.

In some implementations, the LFP-stimulation component of the model is tested to predict successfully formed memories in at least a subset of the same patients and the efficacy of the model is tracked to continuously predict successful memory in the long-term (e.g., 1-2 years) using an FDA-approved device.

In some implementations, LFP signatures (e.g., theta-gamma and cross frequency coupling) during off/on stimulation are correlated with behavioral memory performance intermittently throughout 1-2 years after implant to inform and optimize developing computational model and to characterize stimulation-LFP relationship to memory in the long-term.

Some implementations include measurement of neurophysiological signals (e.g., LFP activity) during long-term (e.g., greater than 1 year) chronic stimulation of the HEC system in two human epilepsy patients. Some implementations include an optimized computational model incorporating recorded long-term LFP signatures (e.g., theta-gamma coupling, theta phase and power) that is used to trigger stimulation of HEC system in TBI patients.

Some implementations include an investigational toolkit for chronic, active probing of networks of neural circuits in humans relevant to memory restoration. In some implementations, the disclosed neurotechnology builds on an investigational human-use device, such as the Medtronic Activa PC+S DBS system. In some implementations, the core system(s) are deployed for a human patient population (e.g., 10 units).

Some implementations include the use of multiple (e.g., 10) systems of Medtronic's Activa PC+S device for implantation, chronic stimulation and data gathering.

To support clinician-initiated research protocols, in some implementations, a computer-in-the-loop system for flexible stimulation pattern testing is deployed, including synchronization with externally derived tasks and algorithm development capability for preliminary closed-loop research.

In some implementations, the distributed (computer-in-the loop) architecture provides a flexible platform for multi-scalar feedback loops to be implemented using multiple sensors, classifiers and models, and control policies.

To support the clinician-initiated research protocols and model generation, in some implementations, the capability of delivering unique stimulation patterns informed by modeling is provided.

Complex stimulation patterns provide another degree of freedom for network probing, model development, and potentially improving stimulation response outcomes. In some implementations, additional firmware-unlocked investigational patterns are warranted.

In some implementations, firmware support is used to enable novel stimulation parameters for a neuromodulation device. In some implementations, the neurmodulation device incorporates novel stimulation patterns to support modeling the effects of stimulation on brain activity and disease state. Some implementations include transfer of optimal stimulation patterns for final stimulation IC and algorithm design for a neuromodulation device.

Some implementations include mitigating telemetry restrictions to the computer-in-loop system by adding ability to update algorithm firmware.

For sub-acute validation of algorithms (e.g., days to a week in controlled environment) and to mitigate the telemetry restrictions, some implementations include the transfer the most promising algorithms to embedded firmware for exploration in a more natural environment. In some implementations, the updated algorithm firmware is downloaded through wireless telemetry without an invasive procedure.

Some implementations include the ability to download scalable algorithms onto an embedded system (e.g., an embedded Activa PC+S system) and transfer of algorithms to an embedded controller.

Some implementations include refinement of the computational model and demonstration of its ability to restore hippocampal dependent long-term memory in humans with memory impairments. In some implementations, the data acquired above is used to refine the computational model for optimal memory restoration. In some implementations, it is then used in the new computational model to restore memory in epilepsy and/or TBI patients with memory impairments.

In some implementations, the computational model is tested in epilepsy patients with microwire depth electrodes (e.g., microwire depth electrode 900, FIG. 9) for simultaneous closed-loop recording and stimulation of the HEC system. In some implementations, the model uses optimized stimulation (e.g., theta-burst) triggered by under-threshold LFP signatures (e.g., theta-gamma coupling) reflective of successful memory to restore memory in epilepsy patients (e.g., using Behnke-Fried electrodes) and TBI patients (e.g., using a Medtronic Activa PC+S device). In some implementations, memory restoration is tested using complete neuropsychological evaluation in addition to the four memory tasks discussed above.

In some instances, developed spike-LFP-stimulation model of HEC activity restores memory in epilepsy and TBI patients for retrieve events of face-name-place associations (i.e., encountering a new person in a store) in three different virtual cities for several days (e.g., up to 14 days). In some instances, the developed spike-LFP-stimulation model of HEC activity restores memory in epilepsy and TBI patients for explicit recall encounters several days (e.g., 14 days) following stimulation. In some instances, the developed spike-LFP-stimulation model of HEC activity restores memory in epilepsy and TBI patients for retrieval of temporal order of several (e.g., 3) encounters (place-person associations). Some implementations include the use of LFPs alone with Fourier combinatorial approach to achieve the retrievals in the TBI patients.

In some implementations, memory in TBI patients is restored using a spike-LFP closed loop wireless stimulation device.

Some implementations include human patients with TBI being implanted with a newly developed closed loop wireless device for simultaneous stimulation and recording of spike-LFP activity within the HEC system. Some implementations include full neuropsychological evaluation for memory in addition to the memory tasks completed longitudinally.

Some implementations include showing memory enhancement for at least several days (e.g., 14 days) for specific learned single items and associations (e.g., item-item associations, item-place associations, and temporal order). Some implementations include a wireless probe for closed-loop recording (spike-LFP) and optimized stimulation of the HEC system to restore specific long-term declarative memories of sequential encounters of specific persons in specific places in TBI patients for several days (e.g., at least 14 days) later. Some implementations include using a model derived from the first TBI patients to restore memory for the persons, places, and associations of these as well as temporal sequence of encounters in a second patient.

Some implementations include the development of a high-density (e.g., 300 µm contact pitch) electrode array (e.g., 32-ch/probe) for recording/stimulation of medial temporal lobe, associated electronic system components that include battery-less implant and battery-powered external wearable device, low-power secure wireless data and power links, and specification for the computational device that will be embedded in the system.

Some implementations include a set of specifications which defines the functional, operational and performance requirements of the overall system. Some implementations include using this system specification to refine the component-level specifications for the neural interface, electronics, and external packaging.

Some implementations include a document of specifications for the overall system and its components. In some implementations, this document is updated as the system is developed and modified.

In some implementations, chronically implantable, subcortical electrode arrays capable of multi-channel electrical recording and stimulation within the hippocampus and entorhinal cortex are developed.

Some implementations include fabrication of electrode arrays on a bio-compatible, thin-film polyimide. Some implementations include accelerated soak testing performed to characterize device and electrode lifetime in-vitro. In some implementations, the arrays are designed to comply with the requirements of ANSI/AAMI/ISO 10993-3:2008.

Some implementations include development of sub-cortical neural interfaces with multiple (e.g., 32) electrodes for electrical recording and stimulation in the hippocampal and entorhinal cortex.

Some implementations include design, fabrication, and testing of low-power modules for use in a multichannel (e.g., 64-ch) battery-less implantable device. In some implementations, the device consists of an artifact-tolerant analog front-end, flexible real-time online data processing, voltage rectifier and regulator, and flexible current-steering stimulator.

Some implementations include, in accordance with the system specification, optimization of various electronic components for minimum power. In some implementations, signal processing techniques are used to enhance circuit design and set new boundaries for electronic implants. In some implementations, the stimulation module uses 0.35 µm technology or 40 nm CMOS.

Some implementations include performing hardware lab/animal tests to demonstrate battery-less multi-channel recording and stimulation capabilities with inductive power.

Some implementations include design and fabrication of: (1) a revolutionary multi-channel amplifier (e.g., less than 1 µA/ch), 4-ch module for single-unit recording; (2) a robust VCO-based artifact-tolerant front-end for LFPs (e.g., less than 1 µA/ch); (3) a real-time flexible DSP (e.g., ~1 µW/ch) to extract single-unit features in order to reduce Tx data rate and minimize sensing power; (4) a flexible stimulation driver, 1-ch module, and associated multiplexer for use in stimulation; (5) a voltage rectifier and regulation module to power the implant based on inductively-transferred power. In some implementations, off-chip storage is used to mitigate peak-average ratio. Some implementations include integration of the modules in functional subsystems with increased channel count (e.g., 16 single-unit+16 LFP) and verification of the performance in lab-bench and animal in-vivo experiments. Some implementations include: (1) a 16-ch recording front-end and online DSP sub-system with voltage rectifier and regulator; and (2) a programmable current-steering stimulator to provide bi-phasic currents as high as 2 mA, 10 Hz-1 kHz for a maximum electrode impedance of 10 kO at 1 kHz, up to 4 channels (configurable: 1, 2, 4) supported for increased stimulation area. Some implementations include a modified neuromodulation device developed for testing in rodents with TBI and non-human primates.

Some implementations include design and fabrication of modules of a secure wireless transceiver for use in the implantable device. Some implementations include, in accordance with the system requirements, design of low-power radio blocks that are compliant with FCC bands for near-field communication in medical implants. Some implementations include use of low-power encryption and RF techniques to fulfill security requirements. Some implementations include scale up of channel count (e.g., 16-ch) and integration of Tx/Rx modules. Some implementations include demonstration of secure wireless Tx/Rx functionality in lab-bench and animal in-vivo tests.

Some implementations include providing circuit and architecture diagrams of the secure wireless transceiver and demonstration its over-the-air performance.

Some implementations include finalizing specifications for the portable computational device including power, size, and programming model. In some implementations, the device includes embedded innovative algorithms for artifact removal and embedded nonlinearity correction of the implantable front-end circuits, and use of the secure wireless telemetry unit discussed above.

Guided by the required hardware resources to support the model, some implementations include determining a best architecture for the embedded computational processor. Some implementations include performing accuracy-complexity analysis of innovative adaptive filter designs for artifact rejection to decide the approach best suited for practical realization and testing on an FPGA. Some implementations include a system demonstration of the AFE and adaptive filter to show that it can reject artifacts up to 200 mV.

Some implementations include analysis of complexity-accuracy tradeoff and simulated filter performance, convergence, and latency requirements. Some implementations include a report of hardware complexity (real-time computations, memory size) for the embedded memory model, required flexibility, choice of hardware architecture, FPGA prototype of hardware-friendly adaptive filter tested with the recording and stimulation modules discussed above.

Some implementations include development of a hermetic package and interconnect for implant device. In some implementations, miniaturized implantable packages are developed with high-density feedthroughs, interconnects, and RF coil-pairs for power and data transfer. In some implementations, these technologies are used to integrate a fully-implantable system consisting of RF power and data telemetry, recording and stimulation electronics, and neural interfaces.

In some implementations, the fully implantable system consists of 3 main parts: (a) skull-mounted module containing the implantable electronics for stimulation and recording; (b) sub-cortical arrays; and (c) RF coils. In some implementations, the electronics packages comply with the requirements of ANSI/AAMI/ISO 10993-3:2008. In some implementations, the data and power coils are fabricated in a co-axial geometry.

Some implementations include fabrication of miniaturized packages, interconnect technologies, RF coils, and package integration with neural interfaces and RF coils. In some implementations, the implantable system's functionality is verified in-vitro, and hermeticity testing of the package is performed to meet MIL STD 883.

Some implementations include neural interface verification and validation testing. Some implementations include evaluating and verifying a neural interface lifetime, sterility and biocompatibility. In some implementations, established methods of testing device lifetime and biocompatibility are used to evaluate the safety of the neural interfaces in-vitro as outlined by ANSI/AAMI/ISO 10993-3:2008 and ANSI/AAMI/ISO 11135-1:2007.

Some implementations include assembly of a portable multichannel (e.g., 64-ch) device with embedded memory model. In some implementations, an external package similar to the external cochlear implant is developed. In some implementations, the package houses portable electronics with near-field secure wireless link to the implant, rechargeable battery, primary coils, and a secure wireless Bluetooth low-energy ("BLE") link to mobile devices. In some implementations, established medical device packaging technologies are used to develop an external electronics package with an interface to the primary coils.

Some implementations include presenting the design history file, fabrication data, and ANSI/AAMI/ISO data for a sub-chronic (e.g., less than 29 days) FDA IDE application for electrode arrays. Some implementations include a full system specification for the neuromodulation system consisting of an implantable device and external portable earpiece device.

Some implementations include compiling the safety and performance data required for an IDE application as well as developing the IDE application for submission to the FDA.

Some implementations include creation of an IDE submission document for the fabricated electrode arrays as well as detailed specification for the neuromodulation system (e.g., including an implantable 32-channel device and an external portable earpiece device) with secure wireless telemetry and embedded memory mode.

Some implementations include development of a 64-ch (two probes, each probe: 16 AP, 16 LFP) closed-loop neuromodulation system consisting of implantable device and an external portable device with embedded memory model. In some implementations, the high-level system design requirements for a fully implantable system are refined based on results obtained above. Some implementations include generation of a document for a fully implantable system including the specification of all the components within the system.

Some implementations include design and fabrication of a final design based on any modification due to the results obtained above. In some implementations, sub-cortical neural interfaces with 64 electrodes for electrical stimulation and recording in the hippocampal and entorhinal cortex are developed. In some implementations, the neural interfaces meet the specifications for human studies.

Some implementations include integration of constituent components (AFE, DSP, Tx/Rx, stimulator, VRM) in a 2-chip (e.g., recording and stimulation) solution for use in animal and human experiments. In some implementations, individual components are assembled in a 2-chip system (e.g., recording: AFE, DSP, Tx-Rx, VRM; stimulation) that can support 64 recording and up to 4 stimulation channels. In some implementations, the modules are used in both the implantable and external/portable devices. Some implementations include fabrication and testing of the two-chip stimulation/recording system and a report of measured performance. In some implementations, a modified TA2 device is developed for testing in rodents with TBI and non-human primates.

Some implementations include development of a secure wireless telemetry module. In some implementations, modules of a secure wireless transceiver are designed and fabricated for use in animal and human subjects. Consistent with final system requirements, some implementations include design of a low-power Rx/Tx that is compliant with FCC bands for near-field communication in medical implants. Some implementations include the use of low-power encryption and RF techniques to fulfill security requirements. Some implementations include scaling up to 64 channels and integrating the Tx/Rx modules. Some implementations include demonstration of secure wireless Tx/Rx functionality in lab-bench, animal, and human tests.

Some implementations include development of a robust portable device with embedded memory model. In some implementations, a flexible portable device is developed that meets the specs, including artifact rejection capability. Some implementations include developing software to program the memory model. In some implementations, the device is customized as needed to provide flexibility required by the models and to embed the robust artifact-rejection algorithm and secure wireless telemetry. Some implementations include demonstration of models running on the device, with up to 200 mV artifact rejection. Some implementations include providing a user guide and programming model for the device, embedded artifact rejection algorithm, and real-time performance report. Some implementations include updating and verifying the memory model based on input.

Some implementations include developing a hermetic package and interconnect for implant device. Some implementations include developing miniaturized implantable packages with high-density feedthroughs, interconnects, and RF coil. In some implementations, these technologies are used to integrate a fully-implantable system consisting of RF power and data telemetry, recording and stimulation electronics, and neural interfaces. In some implementations, the fully implantable system consists of 2 main parts: skull-mounted controller module containing the implantable electronics for stimulation and recording; and sub-cortical arrays. In some implementations, the electronics packages comply with the requirements of ANSI/AAMI/ISO 10993-3:2008.

Some implementations include fabrication of miniaturized packages, interconnect technologies, integration with neural interfaces and RF-coil. In some implementations, the implantable system's functionality is verified in-vitro, and hermeticity testing of the package is performed to meet MIL STD 883.

Some implementations include system verification and validation testing. Some implementations include evaluating and verifying the complete implantable system's lifetime, sterility and biocompatibility. Some implementations include using established methods of testing device lifetime and biocompatibility to evaluate the safety of the neural interfaces in-vitro as outlined by ANSI/AAMI/ISO 10993-3:2008, ANSI/AAMI/ISO 14971:2007/(R)2010, and ANSI/AAMI/ISO 11135-1:2007.

Some implementations include all the components having passed the appropriate ANSI/AAMI/ISO characterization and testing for sub-chronic implantation. In some implementations, the devices are ready for IDE application upon successful sterility and biocompatibility testing.

Some implementations include assembly of a portable 64-ch device with embedded memory model. Some implementations include development of an external package similar to the external cochlear implant which contains the external electronics, battery, and primary coil. Some implementations include integration of constituent components of an external earpiece device. In some implementations, an external electronics package is developed using established medical device packaging technologies. Some implementations include assembly of: (1) secure wireless telemetry with RF coils for data and power; (2) an embedded processor with memory model, artifact rejection algorithm, and system controller; (3) a secure BLE link to mobile devices; and (4) a rechargeable battery. Some implementations include fabrication of external packages, interconnect and assembly technologies, and integration with battery system and electronics. Some implementations include development of external earpiece devices for use in human trials.

Some implementations include assembly of the implantable 64-ch device with secure wireless telemetry. Some implementations include assembly and verification of human-quality systems for implantation in human patients for short-term use (e.g., less than 29 days) in an epilepsy monitoring unit. Some implementations include assembly of human quality systems using the components developed above and performance of system level validation and verification testing. Some implementations include fabrication of external packages, interconnect and assembly technologies, and integration with battery system and electronics. In some implementations, the external system's functionality is verified. Some implementations include sterilization of the human-quality systems.

Some implementations include submitting a complete IDE application for the complete implantable system including the design history file, fabrication data, and ANSI/AAMI/ISO data for sub-chronic (less than 29 days) FDA IDE application for electrode arrays, full system specification for the neuromodulation system consisting of the implantable and external device. Some implementations include compiling the safety and performance data required for the IDE application as well as developing the IDE application for submission to the FDA.

Some implementations include measuring the dynamics of large neural ensembles from HEC system during complex memory formation task in rodents and non-human primates. The primary goal of these tasks is to understand how a declarative memory trace is formed in the HEC circuit and test whether the memory trace can be restored by the developed computational model. In some implementations, this is done by testing the predictions of the computational model by determining the dynamics of large neural ensembles in the HEC circuit during complex memory tasks in rodents and nonhuman primates and deciphering the sensory and neuronal network mechanisms underlying this learning.

Some implementations include developing optimal stimulation protocol to enhance memories and to test the wireless device in behaving rodents. In some implementations, these three parts are conducted in a progressively complex and deterministic fashion to obtain robust understanding.

Some implementations include measuring the dynamics of hippocampal CA1 neurons activity during a simple two-dimensional virtual visual exploration task. This reveals how a single sensory modality without any memory load is represented by neural ensembles and learned. In some implementations, this forms a baseline on which all subsequent and complex results are built. While virtual reality is an emerging tool, no study so far has measured hippocampal CA1 neurons' dynamics in a two-dimensional maze, with all previous studies restricted to one-dimensional mazes.

In some implementations, distal visual cues are used initially since cognitive maps are formed based on distal visual cues. Some implementations include implanting up to 25 tetrodes bilaterally in the dorsal CA1. In some implementations, rats are trained to forage for food rewards on an open platform in the real world or on a similar open platform in the virtual world. Data is measured to ensure even coverage of the platform and similar behaviors in the two environments. Some implementations include measurement of the activities of at least three hundred well isolated neurons from rats in both real and virtual words, along with the local field potentials from at least a dozen electrodes. Some implementations include comparison of these results to data from the real world, where uncontrolled multisensory cues are present, to provide data regarding the contribution of the visual modality alone in generating a declarative representation of space.

Some implementations include measuring the dynamics of the entorhinal grid-cells, border cells, and head direction cells in a two-dimensional visual virtual reality. Some implementations include implanting at least 20 tetrodes in the dorsal medial entorhinal cortex along with at least one tetrode in the dorsal hippocampus in rats and measuring the neural activity during random foraging tasks in real and virtual worlds. Some implementations include measurement of at least 100 grid cells, 100 head direction cells and 50 border cells from the rats. This provides the first direct measurement of the contribution of only the distal visual cues to the formation of head direction, grid and border cells in the virtual world. Importantly, the environment borders in the real world are defined by multisensory cues (e.g., visual and tactile) but there are no tactile cues in the virtual world. Some implementations include determining if rats can form complex concept of world boundary using only visual cues and if neurons can form this representation too. In some implementations, these experiments provide the baseline results for single sensory modality's influence on place cells, grid cells, head direction cells and border cells with minimal cognitive load.

Some implementations include measuring the dynamics of hippocampal CA1 neurons during learning a complex memory task with only distal visual cues. Some implementations include training rats to do a complex declarative memory task with only distal visual cues. In some implementations, the task is fashioned after the classic Morris water maze task, commonly used in the real world to test declarative memory. In some implementations, the water maze task is adapted to the virtual world where non-visual sensory modalities do not contribute, which is not possible to do in the real world. In some implementations, analysis techniques determine the change in spatio-temporal selectivity pattern of place cells with learning the complex declarative memory task. In some implementations, activity of at least three hundred well-isolated place cells is measured during this task along with dozens of field potentials. In some implementations, the results provide the first direct measurement of place cells' contribution to complex declarative memory task. The timing of spikes with respect to the field potential and its evolution with experience provides the contribution of neural rhythms to memory formation.

Some implementations include measuring the dynamics of entorhinal-hippocampal interaction during complex memory task with only visual cues. Some implementations include a combination of the cellular physiology approach and the behavioral approach. Some implementations include measurement of at least 100 grid cells and border cells and at least fifty head direction cells from rats. In some implementations, the results provide the first direct measurement of how oscillatory coupling between the entorhinal cortex and hippocampus evolves with learning. In some implementations, these results are then used for patterned electrical stimulation experiments.

validated models of experimental TBI (i.e., fluid percussion-FPI, controlled cortical impact-CCI, and closed head injury-CHI) and 2 ages of development (e.g., late adolescent postnatal day-PND 35-45, adult PND90) are utilized. For behavioral correlates of TBI-induced memory impairment, some implementations include novel object recognition memory and spatial memory. To conserve animals, in some implementations, subjects are outfitted with the wireless telemetry system to capture electrophysiological ("EP") data at the time of behavioral testing. In some implementations, the EP data is subsequently analyzed and incorporated into a model.

Some implementations include establishing behavioral correlates of human TBI-related memory impairment with relevant experimental single TBI models. Some implementations include a longitudinal within-subject study of single TBI models using memory behavior (NOR, spatial or associative learning) as primary outcomes (e.g., see the third, fourth, and fifth rows of Table 2 below). In some implementations, animals are run in squads (e.g., 4-8 animals per squad) divided evenly over the time course. Some implementations include surgery, behavioral testing, and terminal tissue collection at conclusion of the timeline for each squad of animals.

Some implementations include a determination of best single TBI model for studying translational mechanisms of TBI-induced impairment. Some implementations include behavioral results showing conditions of maximal TBI-induced impairment. In conjunction, some implementations include molecular and histological correlates of TBI-induced memory impairments as secondary outcomes.

Some implementations include a longitudinal within-subject of multiple TBI models using both memory behavior (NOR, spatial, associative learning) as primary outcomes (e.g., see the sixth, seventh, and eighth rows of Table 2 below).

TABLE 2

| | PND 35-45 Adolescent | | | | PND 90 Adult | | | |
|---|---|---|---|---|---|---|---|---|
| | EP-NOR PID 4, 14, 30 | EP-Spatial PID4 | EP-Spatial PID14 | EP-Spatial PID40 | EP-NOR PID 4, 14, 30 | EP-Spatial PID4 | EP-Spatial PID14 | EP-Spatial PID40 |
| Sham-crani | 10 | 8 | 8 | 8 | 10 | 8 | 8 | 8 |
| FPI | 10 | 8 | 8 | 8 | 10 | 8 | 8 | 8 |
| CCI | 10 | 8 | 8 | 8 | 10 | 8 | 8 | 8 |
| Sham-Intact | 10 | 8 | 8 | 8 | 10 | 8 | 8 | 8 |
| CHI ×1 | 10 | 8 | 8 | 8 | 10 | 8 | 8 | 8 |
| CHI ×4 | 10 | 8 | 8 | 8 | 10 | 8 | 8 | 8 |

Some implementations include: (1) establishing behavioral correlates of human TBI-related memory impairment with relevant experimental TBI models; (2) recording and analyzing the linkages between behavior-electrophysiology; and (3) rescuing of memory impairments induced after experimental TBI. In some implementations, recording and analyzing the linkages between behavior-electrophysiology utilizes an updated version of the wireless recording mote already developed. In some implementations, rescuing of memory impairments induced after experimental TBI requires the addition of stimulation capabilities to the hardware package.

Some implementations include establishing behavioral correlates of human TBI-related memory impairment with relevant experimental TBI models. In some implementations involving rodent TBI studies, 3 well characterized and In Table 2, FPI=fluid percussion injury; CCI=controlled cortical impact; CHI=closed head injury x number of repeated injuries. PID=post-injury day; PND=post-natal day; EP=wireless electrophysiology recording; NOR=novel object recognition. Total adolescent rats=168; Total adult rats=168.

In some implementations, secondary outcomes include molecular and histological analyses after the final time point for each group (e.g., half of each group going to molecular and half for histology). In some implementations, secondary outcomes include imaging a subset of rats (half of the NOR rats) once (at PID4) or twice (at PID4 and PID30) using structural MRI, DTI, phMRI.

Some implementations include recording and analyzing the linkages between behavior and electrophysiology. Some implementations include use of the wireless recording hardware system. In some implementations, recording and analyzing the linkages between behavior and electrophysiology involves the same animals as indicated in Table 3 above and the same criteria but with 6-9 month additional time to allow for electrophysiological analyses.

Some implementations include generating electrophysiological results showing conditions of maximal TBI-induced impairment. In conjunction, some implementations include generating behavioral, molecular and histological correlates of TBI-induced memory impairments as secondary outcomes.

Some implementations include obtaining and analyzing multimodal imaging data. In some implementations, imaging, behavior and histological data is correlated. Some implementations include generating imaging results showing conditions of maximal TBI-induced impairment. In conjunction, some implementations include generating behavioral, electrophysiological, molecular and histological correlates of TBI-induced memory impairments as secondary outcomes.

Some implementations include recording and analyzing linkages between behavior and electrophysiology after TBI. Some implementations include establishing and/or providing a setup for a Neurotrauma lab implantation and tethered recordings. Some implementations include analysis of the electrophysiology & behavior data. Some implementations include, at the conclusion of the EP+NR behavior, collection of tissue for molecular and histological data.

Some implementations include analysis of electrophysiological recordings in conjunction with within-subject behavioral, imaging, histological and molecular results. In some implementations, the EP data is generated as discussed above. Of the multiple age groups (adolescent, adult), time points (PID4, 14, 30) and injury models (FPI, CCI, CHIx1, CHIx4), the 2 most promising experimental groups are selected for more detailed electrophysiological recording and subsequent use in stimulation and/or treatment. In some implementations, the relationships between electrophysiological recordings and memory behavior that are dysfunctional after TBI are determined. These impairments will then become the targets for intervention.

Some implementations include delineating more comprehensive electrophysiological (EP+) recordings and their behavioral correlate with experience-dependent plasticity in the virtual reality (VR) environment. Some implementations include the use of the tethered recording system in the VR environment. In some implementations, this data is then used to generate algorithms to model EP correlates of declarative memory for stimulation as well as for comparison and translation to primate and human technical aims.

In some implementations, these rats are heavily instrumented and so they are not be subject to imaging or 'regular' behavior (NOR, spatial). In some implementations, they are, however, subject to histological and/or molecular analysis at the end of the recording period.

Some implementations include surgery, EP+ recording, behavior in VR, and tissue collection at conclusion of monitoring. Some implementations include generating data relating EP+ recording, behavior, and markers of neuroplasticity in this model. In some implementations, this data is used in determining potential targets (electrophysiological, behavior or molecular biomarkers) for stimulation.

Some implementations include delineating wireless EP recording and their behavioral correlate with experience-dependent plasticity in the enriched environment. Some implementations include using the wireless recording system. In some implementations, delineating wireless EP recording and their behavioral correlate with experience-dependent plasticity in the enriched environment is used as demonstration of electrophysiological correlate for impaired neuroplasticity after TBI. In some implementations, this data is used to generate algorithms to model EP correlates of declarative memory for stimulation as well as for comparison and translation to primate and human technical aims. Some implementations include using rats instrumented with the wireless device so they may undergo behavior (NOR, spatial), as well as histological and/or molecular analysis at the end of the recording period.

Some implementations include non-human primate testing of computational model and the wireless implantable device. In some implementations, an animal model is generated for testing the electrode/recording system before its use in humans and to test the efficacy of the triggered stimulation in tasks similar to those used in the patient studies. The advantage of using non-human primates is the ability to train them on a variety of behavioral tasks similar to those used by the patients, but they can do far more trials and sessions over many months or years to reliably quantify the effects of stimulation. In addition, in accordance with some implementations, the use of different tasks and, within the tasks, different distracters, allows for testing of whether stimulation affects specific aspects of memory.

Some implementations include preparing the animals for behavioral and equipment testing, by training them on behavioral tasks. In some implementations, training is performed daily for each animal. For example, training the animals on fixation tasks and introducing the animals to each of the tasks, starting with the easiest. (e.g., the visual preferential looking task). In some implementations, the next three tasks will test memory for single items (e.g., faces, objects, and scenes) in addition to spatial and non-spatial associative memories (e.g., object-object and object-place). In some instances, training on the fixation task and the visual preferential looking task takes approximately 2 months. In some instances, training on the remaining three tasks takes about three months each. In some implementations, once the animals can perform a task 75% correct, the training moves to the next task.

A key criterion in assessing the efficacy of stimulation is understanding how it benefits different aspects of memory. Thus, some implementations include collecting baseline behavioral and neural data from behaviorally trained non-human primates. In some implementations, the trained animals' performance is measured under all behavior conditions and the activity of single-units, multi-units and LFPs in the HEC system are recorded while the animals perform the task. In some implementations, each of the behavioral tasks is designed to assess a difference aspect of memory within each task. Specifically, in some implementations, memory for single items (e.g., objects and scenes) in addition to spatial and non-spatial associative memories (e.g., object-object and object-place) are probed. In some implementations, the task designs are flexible such that the stimuli can be varied to test interference over short and long-term memory performance. In some implementations, each animal is tested on each of the tasks over many thousands of trials.

In some implementations, baseline values of performance are generated as well as an indication of how the animals handle interference in the different tasks. Some implementations include generating data sets illustrating the normal performance of the animals, to which the data collected during stimulation is compared.

Some implementations include functionally mapping the entorhinal cortex and the hippocampus to guide placement of stimulation electrodes and to record unit and local field potential data in the behavioral tasks. Some implementations include recording neural data from the entorhinal cortex and the hippocampus from animals during all memory tasks. In some implementations, this recording is done using a standard tethered recording system. Some implementations include generating a mapping data set in each animal and a neural data set for each behavioral task in at least one animal. In some implementations, the data set enables identification of the best implantation location in the non-human primate HEC system for each task. By comparing it to the data that have been recorded previously in epilepsy patients, a cross-species compatible computational model for memory restoration is developed and refined. In some implementations, the data is used to interpret how the entorhinal cortex interacts with the hippocampus in the non-human primate.

Some implementations include multisensory memory trace formation in HEC system. Some implementations include measuring entorhinal-hippocampal dynamics in a multisensory-multimodal memory task. Some implementations include developing a multi-sensory and multi-modal virtual reality system. Some implementations include training at least three rats to form the memory in this space using single or multisensory cues. Some implementations include implanting electrodes in the entorhinal-hippocampal areas using procedures described above. Some implementations include measuring multimodal behavioral memory in this multisensory task. Some implementations include measurement of at least 300 neurons from HEC circuit during multisensory declarative memory formation. Some implementations include deciphering the neural ensemble population vector activity pattern evolution. Some implementations include generating a direct estimate of influence of multisensory stimuli on multimodal memory formation in HEC circuit. Some implementations include generating a direct estimate of the contribution of differential coupling between the lateral entorhinal and CA1 for objects versus medial entorhinal and CA1 for places.

Some implementations include long-term stabilization of multisensory declarative memory trace in HEC system. Some implementations include determining the influence of sleep in the long-term formation of complex memory trace. In some implementations, rats are trained to learn a complex declarative memory task that requires several days of learning. Some implementations include developing electrodes and implants that can measure the activity of the same neurons over many days. Some implementations include measuring the activity of neurons from HEC circuit during task learning and during sleep following learning. Some implementations include developing analysis techniques to decipher the change in neural memory trace after a period of sleep. Some implementations include detection of significant change in the spatio-temporal dynamics of more than 300 neurons from HEC circuit following sleep and its relation to behavioral learning. Some implementations include generating data regarding the contribution of sleep to long term memory trace of a complex declarative task.

Some implementations include determining the contribution of spontaneous entorhinal memory to HEC dynamics and memory. Some implementations include measuring the field potential simultaneously from the neocrotex and the entorhinal cortex during sleep in rats that have learned a complex declarative memory task. Some implementations include simultaneously measuring multiunit and single unit activities from these structures. Some implementations include developing analysis techniques to detect spontaneous persistent activity in MEC during slow wave sleep. Some implementations include determining the dynamics of neural ensembles in MEC during the spontaneous memory. Some implementations include measurement of at least 300 neurons and more than two dozen field potentials in these tasks. Some implementations include detection of spontaneous memory in the entorhinal ensemble and the evolution of memory with learning in the long-term. Some implementations include a direct determination of the role of entorhinal spontaneous memory to formation of a complex memory trace.

Some implementations include determining the influence of Fourier-combinatorial stimulation on HEC memory trace. Some implementations include implanting at least a dozen tetrodes in the lateral and medial entorhinal cortex and another dozen tetrodes in CA1. Some implementations include using the region specific cross-frequency coupling to selectively stimulate LEC or MEC along with CA1 in a patterned fashion. Some implementations include successful completion of stimulation studies in at least three rats to determine long-term safety and efficacy. Some implementations include detection of an enhancement of region specific oscillatory coupling between object versus space areas of entorhinal cortex and hippocampus following the patterned stimulation. Some implementations include a direct demonstration of selective enhancement of complex memory trace following combinatorial-Fourier stimulation.

Some implementations include rescuing memory impairments induced after experimental TBI. Some implementations include examining the two highest-yield groups as determined above, and use stimulation in an attempt to enhance recovery of memory functions after TBI. Some implementations include refinement and construction of a modified rodent wireless recording/stimulation hardware system. Some implementations include analysis of the electrophysiology and behavior data. At the conclusion of the recordings/stimulation and behavior, some implementations include collection of tissue for molecular and histological data.

Some implementations include refinement and construction of the wireless recording and stimulation hardware system. Some implementations include an analysis of the electrophysiology & behavior data. In some implementations, the wireless device, recording and stimulation protocols are determined for testing. Some implementations include developing a wireless implantable neuromodulation device for closed-loop stimulation and recording suitable for testing modulation of memory function in freely behaving rodents.

Some implementations include rescue of experimental TBI-induced memory impairments using wireless recording-stimulation device. Some implementations include inducing a behavioral-memory deficit with an electrophysiological correlate, then using selected stimulation to alleviate these impairments. Some implementations include the wireless implant hardware with the addition of any stimulus capability. In some implementations, the results are used to determine what behavioral testing paradigm are most robust, and the behavioral memory outcome designated for rescue. Some implementations include the computational model successfully integrated into the TA2 device and implanted into rodents with TBI. Some implementations include the device successfully restoring memory in TBI rodents with previous memory impairments. Some implementations include generating an incorporated computational model into rodent wireless implantable neuromodulation device for memory. Some implementations include successful implantation of device in freely moving TBI rodents and consequent memory restoration.

Some implementations include testing prototypes of the electrode/recording system. Some implementations include basic efficacy testing. Some implementations include before the new wireless implantable neuromodulation device is tested in human patients, testing the safety and efficacy of the device in vivo in non-human primates.

Some implementations include utilizing acute recording sessions, in which the electrode is not chronically implanted and is placed in unrelated cortical areas (so that entorhinal cortex and the hippocampus are not damaged during testing). This allows for testing for basic efficacy and to test for noise/grounding problems. Once these issues are solved, the electrode is placed in the areas of interest within the HEC system and testing is performed to determine whether units-LFP activity is recorded and whether the microstimulation system is functioning correctly.

Some implementations include generating a functioning and robust system ready for permanent implantation. Some implementations include testing whether the recording system is robust over time, by implanting electrodes in the areas of interest in animals. In some implementations, tests start with a single implant, to elucidate whether the system works when chronically implanted and how long it remains viable. If necessary, modified versions are implanted in different locations in the same animal and in similar locations in the second animal. Some implementations include generating a functioning and robust chronic implantation system that can record electrophysiological signals and stimulate over the long-term (greater than 6 months).

Some implementations include testing the effects of stimulation on memory performance. Some implementations include identifying the efficacy of stimulation on memory performance in the non-human primate. The benefit of doing this in the animal model is that the entorhinal cortex and the hippocampus in the animals is already mapped and recorded and thus a determination can be made as to whether electrode placement based on that data is an appropriate approach for implantation in patients. In addition, the animal model allows for gathering a substantially larger data set that allows for teasing apart the benefits of stimulation in different locations for different forms of memory.

Some implementations include the recording being done in animals that are not used to test the equipment. Some implementations include generating full significant data sets from nonhuman primates in each task. Some implementations include significant enhancement of memory using new implantable wireless neuromodulation device. Some implementations include generating long-term (e.g., greater than 1 year) safety and efficacy data of the device on non-human primates. Some implementations include generating strong statistical evidence of the efficacy of stimulation across each of the four tasks.

Some implementations include multiple stages and, during each stage, several results and products are generated. For example, during stage 1, a computational model of long-term declarative memory formation in human epilepsy patients implanted with depth electrodes (e.g., Behnke-Fried electrodes) is developed for up to two weeks for clinical evaluation. Single-unit and LFP activity is recording with the capability of simultaneous closed loop stimulation of the HEC system. This stage combines computational modeling simulations of the HEC declarative memory system and single-unit and LFP recordings to determine successful memory related neurophysiological signatures and optimal stimulation parameters for memory restoration. During stage 2, the same two epilepsy patients whom have chronic implanted electrodes (e.g., NeuroPace RNS) for closed-loop LFP recording and stimulation are monitored for long-term characterization (e.g., greater than 1 year). This stage is crucial for refining the computational model and testing it in for restoration of memory. Stage 3 utilizes the finalized LFP-stimulation components of the model to restore memory in patients with TBI using chronic electrodes (such as Medtronic DBS electrodes) for simultaneous recording and stimulation. Stage 4 incorporates the spike-LFP components of the computational model into a new developed wireless closed-loop neuromodulation device for restoration of long-term declarative memory in TBI patients. For an exemplary summary of stages see Table 3 below showing the type of patients involved, the neurophysiological signals recorded, timeline of stimulation, electrodes and electronics used, and the primary indication for implantation.

TABLE 2

Exemplary Stages of Development and Testing

|  | Stage | Patients | Signals | Stimulation | Electrodes | Electronics | Primary Indication |
|---|---|---|---|---|---|---|---|
| Phase I | 1 | Epilepsy | Single neurons, LFPs | semi-chronic | Depth Behnke-Fried with microwires | Externalized (Neuralynx) | Epilepsy |
|  | 2 | Epilepsy | LFPs | chronic, intermittent, task-related | FDA approved NeuroPace RNS | FDA approved NeuroPace RNS | Epilepsy |
| Phase II | 3 | TBI | LFPs | chronic, intermittent, task-related | Medtronic 3389 DBS electrode | Activa PC + S (requiring IDE) | Memory Investigational |
|  | 4 | TBI | Single neurons, LFPs | chronic, intermittent, task-related | Developed by TA2 RAM team | Developed by TA2 RAM team | Memory Investigational |

Some implementations include development of a 64-channel Neuromodulation System (e.g., computing system 100, FIG. 1). In some implementations, the resulting technology of this work is a complete implantable, chronic recording and stimulating array with a programmable computational device for memory restoration, as shown in FIG. 2. In some implementations, the complete 64-channel wireless system includes: (1) co-axial external primary RF-coils for transcutaneous power and data transfer between the external and implanted devices; (2) implanted electronics module with electronics for stimulation and recording; (3) secondary co-axial RF coils for secure power and data telemetry; (4) a sub-cortical neural probe for implantation in the entorhinal cortex (e.g., with 32 channels); (5) a sub-cortical neural probe for implantation in the hippocampus (e.g., with 32 channels); and (6) an external wearable earpiece with embedded memory model and secure wireless link to the implant as well as wireless link to a mobile device (e.g., a phone or tablet). In some implementations, various components of the final device are tested in animal models, to inform the model for human trials, and to test in-vivo functionality and performance. In some implementations, the wireless mote undergoes three-stage development (v2, v3, v4) to incorporate the newly developed probes, associated electronic, and package components.

In some implementations, the following are components are developed: (1) a high-density 32-channel electrode array with associated system components including battery-less implant and battery-powered external device; (2) a document detailing specifications of all system components; and (3) novel 32-channel sub-cortical neural probes (FIG. 3A-3C) characterized and tested for stimulation and recording. In some implementations, the probes meet the standards of GLP, GMP, and GCP.

In some implementations, the following are components are developed: (1) battery-less multi-channel recording and stimulation modules; (2) specifications of portable device with embedded memory module; (3) preliminary design of miniaturized packages, interconnect, RF coils; (4) ISO 10933 biocompatibility at a certified facility for IDE submission; (5) report on testing of neural interface lifetime, sterility, and ISO-10993 biocompatibility; (6) submission of IDE application for fabricated electrode arrays; and (7) submission of FDA IDE application for the electrode device (bilateral entorhinal and hippocampal stimulation and recording) that is to be used in clinical trial for memory restoration for traumatic brain injury (TBI), and specifications for the Phase II system.

In some implementations, the following are components are developed: (1) record of hippocampal spike-LFP activity from rodents (sham, naïve, TBI) housed in an enriched environment, using an in-house wireless device (v1, FIG. 5), up to 6 animals concurrently; (2) hardware architecture for the computational module; (3) components of the closed-loop DBS device; and (4) a wireless mote with stimulation capability, tested in rodents and non-human primates.

In some implementations, the following are components are developed: (1) a 64-channel closed-loop neuromodulation system (also sometimes called "UCLA 64RS") consisting of a 64-channel battery-less implantable device (also sometimes called "iR64S") and an external portable device (also sometimes called "eR64S") with embedded memory model. Functional components of the exemplary system are shown in FIG. 7.

In some implementations, the following are components are developed: (1) a document detailing specifications of overall system: (a) electrode technology for clinical DBS in human patients, and (b) derived specifications for the final DBS device (electronics, processor, wireless link, package); (2) second-generation of novel sub-cortical neural interfaces; (3) a 64-channel wireless recording and stimulation integrated circuit; (4) a secure wireless telemetry module; and (4) a DBS device that meets the criteria set above.

In some implementations, the following are components are developed: (1) assembled devices required for testing for IDE documentation and devices for human implantation, with hermetically packaged (as shown in FIG. 4) battery-less electronics; (2) wirelessly transferred hippocampal electrophysiological data from the implanted IPG device to an external computational device; and (3) results of characterization and testing for IDE submission.

In some implementations, the following are components are developed: (1) a prototype 64-ch device with embedded memory model for IRB approval testing and for human trials; (2) a 64-channel device with secure wireless telemetry assembled for verification and validation testing and for human implantation; and (3) an IDE submission for the full implantable system.

In some implementations, data from a clinical trial for memory restoration in patients with TBI is generated. In some implementations, for each subject, raw data and metadata are collected (with time-stamped behavioral and validated severity of brain injury) from recordings performed both at rest, sleep, and during task-dependent behavior both without and with stimulation. In some implementations, this information is used to test and refine previously generated models of network pathology. In some implementations, the effects of stimulation based on biosignals is also recorded and delivered. In some implementations, acute outcomes of stimulation, including 4 h, 24 h, 48 h, and 14 days is evaluated and reported, both with respect to improved mnemonic behavior as well as non-mnemonic behavior to ensure specificity of therapy. The resultant improved models (with details of resultant changes and the value of these invasive studies in defining the refined model) are then developed. In some implementations, using a sensing generator, long-term data (1-2 years) is generated from recordings and stimulation of hippocampus and entorhinal area for evaluating further control programs and the stability of and effects of chronic closed-loop stimulation on neural signatures and behavior. In some implementations, the benefits of stimulation with control parameters based on the models are tested and verified for at least 14 days in a natural free living environment. In some implementations, the benefits of stimulation with control parameters based on the models are tested and verified for over a period of at least 1 year. In some implementations, the developed LFP-stimulation computational model is implemented using the Medtronic Activa PC+S system in memory-impaired TBI patients for restoration of memory. In some implementations, the new spike-LFP computational model is tested in non-human primates and eventually in TBI patients with memory impairments. In some implementations, all recordings, behavioral and outcome data is collected and analyzed.

Some implementations include combining computational modeling, single neuron and LFP recordings with greater spatial and temporal resolution, and adding long-term chronic stimulation of the entorhinal-hippocampal axis in same subjects. Some implementations include leveraging already existing FDA approved technology to refine the computational model that is then incorporated into the developed neuromodulation device (e.g., implantable electronics package 200, FIG. 2).

Some implementations include the use of cross-frequency amplitude-phase coupling. In some implementations, LFP is filtered in appropriate bands using a two-way least squares FIR filter. In some implementations, the LFP spectrum is computed using the multi-taper method from the Chronux open source MATLAB toolbox. In some implementations, confidence intervals are estimated using the jackknife method. In some implementations, for theta analysis, a (6-12 Hz) band is used and then Hilbert transformed to locate the peak for each individual theta cycle. In some implementations, theta peaks are assigned a phase of 180 degrees and the relative phase of theta is computed within each theta cycle. In some implementations, the entire data set is then be labeled with a series of theta events centered on theta peaks with a 250 ms window length (e.g., ~50% overlap with both adjacent theta events). In some implementations, slow (and/or fast) gamma amplitudes are obtained by filtering the LFP in 20-45 Hz (or 45-120 Hz) bands and computed from the absolute value of the analytic signal.

In some implementations, for each amplitude and phase frequency pair in a given stimulus bin, the data are grouped into 60 equally spaced phase bins spanning 0-360° based on their phase value; and the mean amplitude of the high frequency signal $f_{amp}$ is calculated for each low frequency phase bin $f_{phase}$ for a given stimulus bin S.

Using these, the Shannon entropy (H) of cross-frequency coupling and its modulation index (MI) is calculated as shown in Equation 1.

Shannon entropy and modulation index $$H(f_{amp}, f_{phase}, S) = -\sum_{j=1}^{N} P_j(f_{amp}, f_{phase}, S)\log[P_j(f_{amp}, f_{phase}, S)],$$

$$MI(f_{amp}, f_{phase}, S) = \frac{\log(N) - H}{\log(N)},$$

Equation 1 where P(j) is the normalized amplitude of the high frequency signal in each low frequency phase bin j, and N is the number of phase bins (e.g., 60). Modulation Index ("MI") is normalized using log(N) and defined this way because the highest value of H is log(N), occurring for a uniform distribution of phases, indicative of minimal modulation.

In some implementations, a computational model of neural activity and synaptic plasticity induced by different stimulation patterns is developed. In some implementations, a synapse is stimulated responding to pre- and postsynaptic stimuli of various Fourier patterns. A presynaptic spike generates an excitatory postsynaptic potential (EPSP(t)). A postsynaptic spike produces a back-propagating action potential (BPAP(t)). The membrane potential V(t) at the synapse is given by the linear sum of these two sources of depolarization. In some implementations, simulations are performed in MATLAB. In some implementations, short term synaptic facilitation and depression are included based on neuron type ion channels. In some implementations, in addition to this reduced model that allows analytic estimates, a multi-compartment model is used to capture the full complexity of dendrites.

Details of the depth electrodes, their implantation, and single unit recording procedures have been described. For example, in some implementations, the MRI-compatible, flexible polyurethane probes (e.g., microwire depth electrode 900, FIG. 9) allow for insertion of 9-17 microwires for single unit recording 5 mm beyond the tip of the probe. For example, in some implementations, the depth electrodes include MRI-compatible, flexible, polyurethane probes with seven 1.5 mm wide platinum contacts, each separated by 5.0 mm on center, with the exception of the two contacts nearest the tip, which are separated by 2.5 mm on center. In some implementations, each electrode has a rigid stainless steel stylet that during introduction allows accurate placement in the brain. In some implementations, after surgical placement in the target structure, the stylet is removed, thus providing the path of entry for a bundle of microwires (e.g., a bundle of 9) with tips spaced at intervals in a vertical array (e.g., 500-μm intervals) which allow recording of a voltage depth profile of placements (e.g., 8 placements) referred to the distal reference microelectrode. In some implementations, the wires are insulated except where cut off at the tip, and the impedances of the wires range from 200 to 800 Kohms, and are capable of resolving multiple- and/or single-unit activity. In some implementations a second microelectrode configuration employs tetrodes adapted to human use for single unit and LFP recording. For example, the tetrodes consist of four 25-μm-diameter platinum wires twisted together. Four of these tetrodes are placed in the lumen of a clinical electrode so that the longest extends out 4.0 mm, the next 3.0 mm and so on, allowing voltage depth profile information to be acquired at the same time as several single neurons are isolated by the tetrodes. In some implementations, electrodes are introduced by an orthogonal temporal approach; that is, through the temporal bone, passing through the middle temporal gyrus to the amygdala, anterior and/or middle hippocampus, entorhinal cortex, and posterior parahippocampal gyrus. In some implementations, electrodes are placed bilaterally in orbitofrontal cortex, a region heavily connected to the temporal lobe. In some implementations, the electrodes are targeted stereotactically using a modified MRI-compatible Leksell frame that is affixed to the outer table of the skull under local anesthesia. In some implementations, MRI and Digital Subtraction Angiography ("DSA") are performed with the stereotactic frame in place, and the data is transferred on the radiology network to the operating room where preoperative planning is carried out using a computerized multimodality stereotactic planning system. In this fashion accurate targeting of mesial temporal sites is accomplished with an error margin of only 1-2 mm. In some implementations, the patient is then brought to the operating room, and the depth electrodes are placed under general anesthesia. In some implementations, each electrode is secured within a screw guide with an o-ring compression cap to prevent CSF leakage. In some implementations, the patient is observed postoperatively for 48 hours in the neurosurgery intensive care unit and then transferred to the telemetry unit for long-term monitoring, which typically takes 10-14 days.

In some implementations, both macro- and micro-stimulation studies are performed under IRB protocols for epilepsy patients implanted with depth electrodes for seizure monitoring and potential curative resection. In some implementations, the macro-stimulation is similar to prior studies where it has been given at the onsets of half of the trials and is current regulated, charge-balanced, with biphasic rectangular pulses set below the after-discharge ("ADG") threshold (based on pretesting). In some implementations, the frequency, shape, and pulse width are verified using an oscilloscope. In some implementations, Behnke-Fried electrode contacts are stimulated through an interface with a Grass C-12 stimulator, Telefactor relay box, and Stellate recording system. In some implementations, stimulation in these studies is bipolar (0.059 $cm^2$ surface area, 1.5 mm apart).

In some implementations, train length varies on the stimulus length presentation for each. Some implementations include testing theta burst stimulation (e.g., 3-5 pulses at 100 Hz repeated at a 5 Hz frequency), which has been shown to induce maximal long-term potentiation supportive of memory. Some implementations include testing behavioral paradigms with three varying increasing amounts of stimulation magnitudes (e.g., 1, 1.5, and 2 mA) and frequency (e.g., 1, 10, and 50 Hz and theta burst) to optimize the parameters necessary for memory enhancement. In some implementations, total stimulation thus ranges between 2.5-10.1 μC/$cm^2$ per phase, which is well below the safe maximum used for chronic (30 μC/$cm^2$ per ph) and acute (57 μC/$cm^2$ per ph) stimulation. In some implementations, a neurologist is present during all sessions to monitor the subject at bedside and view real-time EEG for seizures. In some implementations, no tests are administered less than 2 hours post-seizure. In some implementations, the absence of any after-discharge (ADG threshold) at a particular site is carefully established prior to every session. In some implementations, stimulation is always set below the ADG threshold. Stimulation parameters of up to 3.0V, 450 μs pulse width and 130 Hz, have shown to be safe and well tolerated in patients with epilepsy with depth electrodes in the temporal lobe. Similar stimulation levels are used in clinical studies for seizure control in epilepsy. Some implementations include testing effects of stimulation during learning, recall, and with varying types of material to be learned. Some implementations include quantifying behavioral memory 24 hrs, 48 hrs and 14 days for all behavioral tasks after learning to look at the duration of the effects of stimulation.

In addition to the macro-stimulation studies in human epilepsy patients, a safe IRB approved method of microstimulation is employed. In humans, intracranial microstimulation has so far primarily been a clinical assessment and diagnostics tool with a focus on sub-cortical areas; and research with this method is usually limited to intra-operative. In some implementations, a train of pulses are delivered during parts of a cognitive task in an attempt to influence the subject's memory during this task. In some implementations, the stimulation pulse waveform is designed with two phases (charge balanced), a cathodal phase first followed by an anodal phase. This sequence activates larger sets of neurons than pulses starting with an anodal phase. Some implementations include the use of Pt/Ir microelectrodes with a tip diameter of 100 μm bundled with 9 microwires dedicated to recording single and multiunit activity in the target area. For example, an electrode with a radius of 100 μm, cut at an angle of 45° will have a surface area of 11107 μm². Stimulated with 50 μA with a pulse width of 200 μs, this electrode delivers 10 nC of charge per phase resulting in a charge density of 90 μC cm². These values are both high enough to potentially elicit behavioral reposes and low enough to be considered without risk to the patient.

For example, during a first session in the morning a large set of images are presented to the patients as to find single cell correlates of their conscious perception of a specific image. The thus discriminated images are then used in a follow up session later in the day. During this second part of the experiment the subjects view the specific images as they are faded in from pure noise in a random sequence with repetition. The patients are asked each time to indicate by button push when they see the image. The stimulation of the relevant neural location discriminated during the morning session biases the subjects' memory threshold. Therefore, this procedure helps determine the efficacy of microstimulation as well as generating data regarding the causal role these correlates of memory play within the human medial temporal lobe.

In some implementations, for microstimulation, electrode switching control (e.g., a CereStim Switch) is used, which provides electrode switching control for neural stimulation applications by enabling high-quality neural recordings (spikes and LFPs) immediately after (e.g., milliseconds after) stimulation. For example, the CereStim Switch provides electrode switching control for neural stimulation applications by enabling high-quality neural recordings (spikes and field potentials) immediately after stimulation. The switch is as an add-on module for the Cerebus data acquisition system. It allows for programmatical switching of individual electrodes between a stimulation source and the recording electronics. In some implementations, switch control is accomplished using the CereStim software package or by external gating (TTL) with a 3rd-party control system.

In some implementations, a headstage module capable of switching up to 32 electrodes is used. In some implementations, the stimulation pulse as well as the stimulation protocol (e.g., pulse trains) are generated and controlled within a stimulator unit. In some implementations, immediately after each stimulus, the CereStim Switch switches back into recording mode. At the same time all TTLs that are sent to this setup for stimulation are also recorded alongside the neurological data for post-hoc analysis.

In some implementations, the primary site for stimulation is the ERC perforant pathway. In some implementations, the effects of stimulation on the hippocampus and ERC and parahippocampal gray matter are recorded and analyzed. In some implementations, each side is stimulated separately. In some implementations, when there is bilateral implantation, both sides are stimulated simultaneously. In some implementations, each hippocampus is stimulated separately. In some implementations, at least one of the contacts is in CA1, but the exact subfield of stimulation (CA1, CA3/DG or both) is determined by postoperative electrode localization. In some implementations, in interpreting of the data, the location of the epileptogenic focus is assessed along with whether it included the stimulation site. In some instances, at low level stimulation, there are no after discharges in any of the sites and memory enhancement is achieved even when the stimulation is at a side involved with seizures. In some instances, behavioral enhancement results are unchanged when excluding data from sites that are determined as the epileptogenic focus. Interestingly, low-level stimulation of the MTL is sometimes used to control seizures.

In some implementations, subjects are neurosurgical patients with pharmacoresistant epilepsy who are implanted with intracranial depth electrodes for 7-10 days to determine the seizure-onset zone for possible surgical resection. In some implementations, electrode placements are determined solely based on clinical criteria. All subjects volunteer for by providing informed consent according to a protocol approved by a Medical Institutional Review Board ("IRB"). In some implementations, several (e.g., 8-12) intracranial electrodes are implanted stereotactically using magnetic resonance imaging ("MRI") and digital subtraction angiography ("DSA") guidance.

In some implementations, the electrodes include platinum contacts for EEG recording and stimulation. For example, each electrode contains eight 1.5-mm-wide platinum macro-contacts for clinical use; in addition, eight 40 μm platinumiridium micro-wires situated at the tip of each electrode are used to record extracellular EEG and single-unit activity. In some implementations, special electrodes are used for ERC, with a different prescribed length of each microwire, enabling differential sampling of the various layers of ERC. In some implementations, neural activity from the micro-wires is acquired at a sampling rate of 28 kHz using a 96-channel Neuralynx system or the like. In some implementations, after isolation of single neurons using methods discussed previously, unit activity is categorized as multi- or single-units and pyramidal cells or interneurons on the basis of several parameters to identify putative cell types: (i) waveform duration, (ii) firing rate, and (iii) burst firing propensity. In some implementations, depth EEG data is recorded continuously from each of the 8 macro-wires contacts along the shaft of the electrode.

The FDA approved RNS® System is an implantable therapeutic device that delivers responsive stimulation, an advanced technology designed to detect abnormal electrical activity in the brain and respond by delivering imperceptible levels of electrical stimulation to normalize brain activity before an individual experiences seizures. In some implementations, the RNS® Neurostimulator is 27 mm×60 mm×6 mm and is fully implanted in a surgical defect created in the skull. In some implementations, two leads are connected to the neurostimulator. Leads may be any combination of depth or subdural strip, depending on the anatomical target. For example, depth leads are 1.27 mm in diameter and the cortical electrode strips are 7.5 mm×40 mm. In some implementations, each lead has four platinum-iridium electrodes, either ring (depth lead) or disc (strip lead) electrodes, each with a surface area of 7.9 $mm^2$. In some implementations, the ring electrodes are 1.5 mm long with an electrode spacing of either 3.5 or 10 mm. In some implementations, disc electrodes are 5 mm diameter with a spacing of 10 mm. In some implementations, the RNS® Neurostimulator continuously monitors electrographic activity on four bipolar intracranial EEG (ECoG) channels at 250 samples/sec. In some implementations, the RNS® Neurostimulator is configured by the physician to deliver electrical neurostimulation in response to detected electrographic patterns. In some implementations, electrical stimulation consists of short bursts of symmetrical biphasic current-controlled pulses delivered to electrodes selected by the physician, and can be delivered to different targets depending on which detection algorithm was triggered. For example, amplitude (0-12 mA), pulse width (40-1000 ms), frequency (1-333 Hz), and burst duration (10-5000 ms) are configurable. Typically, epilepsy patients receive 600-1500 responsive therapies per day, amounting to 2-5 minutes per day of stimulation. In some implementations, the RNS® Neurostimulator is powered by a primary cell battery. Battery life is approximately 2-5 years (median time to replacement is 3.7 years), depending on the amount of stimulation delivered. The RNS® Neurostimulator contains a microprocessor that runs software that is optionally transmitted wirelessly to the device. Detection algorithms are implemented in a combination of analog and digital ASIC hardware and software. In some implementations, two kinds of data are stored in the RNS® Neurostimulator, ECoG data and diagnostic event information. In some implementations, up to 30 channel-minutes of ECoG data is optionally stored, triggered by user-configurable events. The event diagnostics describe detections and stimulations delivered by the device.

In some implementations, commercially available RNS® System Neurostimulator and Leads are implanted in a subset of the same depth electrode epilepsy patients that are clinically qualified. In some implementations, where surgical resection of the seizure-onset zone is not feasible even after depth electrode recordings, patients are implanted with the RNS neurostimulator for seizure control. In some implementations, patients implanted with an RNS device within the entorhinal area are consented for entry into the clinical IRB study. In some implementations, the subjects undergo repeated memory testing sessions. During these sessions the existing RNS® System is configured to record ongoing neural activity and to deliver stimulation either on command or in response to the detection of pre-specified signals (e.g., theta or gamma LFP activity).

Some implementations include use of a Medtronic scientific investigational toolkit suitable for chronic human implantation. The toolkit is based on the Activa PC+S ambulatory therapeutic system, which is capable of providing DBS patterns consistent with commercial systems and also recording the local field potentials adjacent to any or all of the 8 electrodes in the system (4 electrodes/lead, 2 leads/unit). In addition to the base capability of the PC+S system, in some implementations, several (e.g., 4) "scientific payloads" are applied. In some implementations, a distributed instrumentation system to supplement the Activa PC+S investigational tool and therapy-delivering platform is included. The distributed instrumentation system addition leverages a custom API that enables data to be both streamed out (e.g., LFP recordings) and streamed in (e.g., operational commands and stimulation waveforms for each channel) in real-time. This bi-directional link, which requires a telemetry receiver externally attached to the patient, allows for the computer-in-the-loop to provide direct neuromodulation control. The advantage of this scheme is that, in accordance with some implementations, stimulation patterns are synchronized wirelessly to memory tasks, and closed-loop algorithms can be prototyped rapidly. Some implementations include the ability to generate novel stimulation patterns such as novel bursts like high-frequency stimulation with a theta-envelope (theta burst stimulation), bounded stochastic signals, and randomized pulse trains. This added functionality opens up new methods of modulating multi-scale networks beyond the classical fixed-pattern approaches of today's devices, and expanding the degrees of freedom for model generation.

In some implementations, subjects complete a spatial learning task using virtual reality. Similar versions of this spatial navigation task are used to successfully recruit MTL activity using fMRI. In some implementations, each test of each separate region (ERC, hippocampus, and parahippocampal cortex) consists of four blocks of navigation trials. For example, in each testing session, subjects learn to navigate to stores in a virtual environment to drop off passengers; each store is repeated in each of the four blocks. To test stimulation's effects during learning, in some implementations, stimulation is applied during the first 3 blocks of navigation to half of the store trials. In some implementations, for each subject, stimulation is applied consistently for learning the location of a given store. In some implementations, navigation under stimulation and no stimulation alternates across trials, and whether learning the first location occurs under stimulation or not is counterbalanced across subjects. In some implementations, to determine effects of stimulation during learning, stimulation is given during block 1-3 of trials; memory performance is then assessed during block 4 and compared between locations where stimulation had been previously applied, and where no stimulation had been applied. To determine the effects of stimulation on recall, stimulation is only given during recall block 4. In some implementations, alternate versions of the spatial task are used for DBS during learning vs. DBS during recall sessions.

In some implementations, navigation blocks are interleaved with control distracter tasks to prevent rehearsal and thus further recruit the hippocampus. In some implementations, control tasks are given to measure whether any effect of stimulation on spatial learning is due to improved motor or perceptual abilities. In some implementations, spatial learning is quantified by first calculating the shortest path length (ideal path) from a passenger to the target store destination. In some implementations, the primary dependent variable in the study is the excess path length determined by subtracting the ideal path from their actual path to the store for each given trial. Shorter excess path length indicates better subject performance. In some implementations, latency to reach the target destination is quantified as an additional measure of navigation efficiency, which is determined by subtracting the time (sec) of passenger pickup from the time of passenger delivery to the store.

In some implementations, all stimuli are presented using a laptop computer. In some implementations, a programming language such as PyEPL is used to present virtual reality stimuli and to record navigational routes and key press reaction times. In some implementations, excess path length, latency, and reaction time performance on the control tasks is calculated using MATLAB.

In some implementations, subjects are instructed to learn a set of novel items (e.g., objects, faces, animals, and places) pairs during an encoding phase. For example, during the encoding block, subjects are shown random images each presented for 3 seconds. They are then presented with a control distracter task in which they are asked to identify a given number as odd or even using the left (odd) or right (even) arrow keys.

In some implementations, for this task, random numbers between 1 and 9 are presented on average every 600 milliseconds. In some implementations, the subsequent recognition block consists of previously learned photographs of the same items or novel unseen items. During this block, subjects respond as to whether they had seen the item before using assigned buttons on the laptop computer. In some implementations, subjects repeat this task across six blocks of alternating learning and recognition (interleaved with control) conditions. In some implementations, to determine the effects of stimulation during learning, stimulation is given during encoding blocks only. In some implementations, a separate session tests the effects of stimulation during recognition blocks. In some implementations, new photographs are used for each set and each new brain region tested. In some implementations, the behavioral performance is analyzed by looking at both accuracy and reaction time using MATLAB.

In some implementations, a paradigm is used in which subjects learn person-location associations closely mimicking tasks used by the nonhuman primate studies. Hippocampal neurons are significantly responsive during the successful learning of novel word paired associations. Primate neurophysiological studies have found stimulus-specific hippocampal responses during the learning of location-scene and object-place associations. In some implementations, a novel paradigm is used in which subjects perform a people-landmark association memory task where two unrelated pictures (e.g., Jennifer Aniston and the Eiffel tower) are used to form a composite learned association (e.g., meeting Jennifer Aniston at Eiffel tower). In some implementations, stimulation's effects on spiking rate and selective responses is monitored and analyzed. In some implementations, for each pair, composite images are created in which each individual is digitally extracted from the original picture and placed in front of the landmark, mimicking a real photo.

In some implementations, subjects are later asked to choose which of 10 landmarks corresponded to each individual. In some implementations, the learning curves for each individual subject are recorded an analyzed. In some implementations, for all three tasks, behavioral memory is quantified on the same day and days following stimulation (e.g., 24 hrs, 48 hrs and 14 days after learning).

Some implementations include a clinical trial to determine stimulation's ability to restore declarative memory in patients with TBI and memory impairments. In some implementations, an FDA IDE approved device (e.g., Medtronic Activa PC+S) is used followed by use of the newly developed wireless implantable device (e.g., implantable electronics package 200). In some implementations, raw and metadata is collected with time-stamped behavioral and validated severity of disease scales from chronic recordings performed both at rest and during task-dependent behavior both without and with stimulation. In some implementations, the effects of stimulation based on biosignals are recorded and delivered. In some implementations, acute outcomes of stimulation, such as 4 h, 24 h, and 72 h and 14 days and up to 2 years post-implant, are evaluated and reported to ensure specificity of therapy.

In some implementations, participants (also sometimes called "patients" or "test subjects") meet at least a subset of the inclusion and exclusion criteria detailed below:

Inclusion Criteria: (1) non-penetrating msTBI (intake or post-resuscitation GCS score between 3 and 12); (2) 18-50 years of age during study entry; and (3) english skills sufficient to understand instructions and be familiar with common words (in some implementations, the neuropsychological tests used presume competence in English).

Exclusion Criteria: (1) history of neurological illness, such as prior msTBI, brain tumor or severe seizures; (2) MRI structural abnormality present, (3) history of psychosis, ADHD, Tourette's Disorder, learning disability, mental retardation, autism or substance abuse; and (4) severe multi-domain cognitive impairment. The latter conditions are associated with cognitive impairments that might overlap with those caused by TBI.

In some implementations, participants with any metal implants preventing them from safely undergoing an MRI scan are also excluded.

In some implementations, all subjects undergo a comprehensive neuropsychological assessment using a standardized battery. In some implementations, measures of interest include (1) literacy and pre-morbid IQ estimate; (2) verbal memory measures such as CVLT, WMS-IV Logical Memory and Verbal Pairs, immediate and delayed; and (3) visual memory measures such as Rey-Osterrieth Complex Figure (e.g., 3 and 30 minute delay), Brief Visual Memory Test (BVMT), and WMS-IV Visual Reproduction immediate and delayed. In some implementations, all participants also undergo behavioral memory tasks as described above to determine the stimulation's more specific effects on the restoration of hippocampal dependent spatial, non-spatial, associative and specific memory traces. Impairment in memory is operationally defined as a score 1.5 SD below the age appropriate population mean on the WMS-IV Index. In some implementations, participants are not entered into the program if they do not have impairments in declarative memory.

During the first year post-TBI there is a robust, but unfortunately incomplete, improvement in neurocognitive functioning. There is enormous variability between subjects in the pace of recovery at different time points during the first year post-TBI. By 13 months post-injury spontaneous recovery is waning and therefore the effects of treatment are less likely to be obscured by background variations in rates of spontaneous recovery.

In some implementations, all patients receive implantation with either the Activa PC+S or the implantable electronics package 200 (FIG. 2). In some implementations, a within subject design is used to test whether stimulation enhances declarative learning and memory. In some implementations, during test, neither participant nor experimenter knows during which trials stimulation is on. In some implementations, stimulated trials are randomized throughout each experiment such that overall half of trials are stimulated and half are not stimulated to directly test the effects of stimulation on memory.

In some implementations, a 64-channel closed-loop neuromodulation system is developed (e.g., R64S system, FIG. 7). In some implementations, the system consists of a 64-channel battery-less implantable device (e.g., implantable electronics package 200, FIG. 2) and an external portable device (e.g., external device 204, FIG. 2) with embedded memory model. In some implementations, the implantable device contains 2 sub-cortical leads with 32 electrodes per lead and wirelessly communicates with an external device. In some implementations, the external device contains programmable electronics for artifact rejection allowing simultaneous R+S, embedded memory model, and a system controller. In some implementations, the system is programmed/updated via a portable device (e.g., phone/tablet or the like).

Figure 3C:
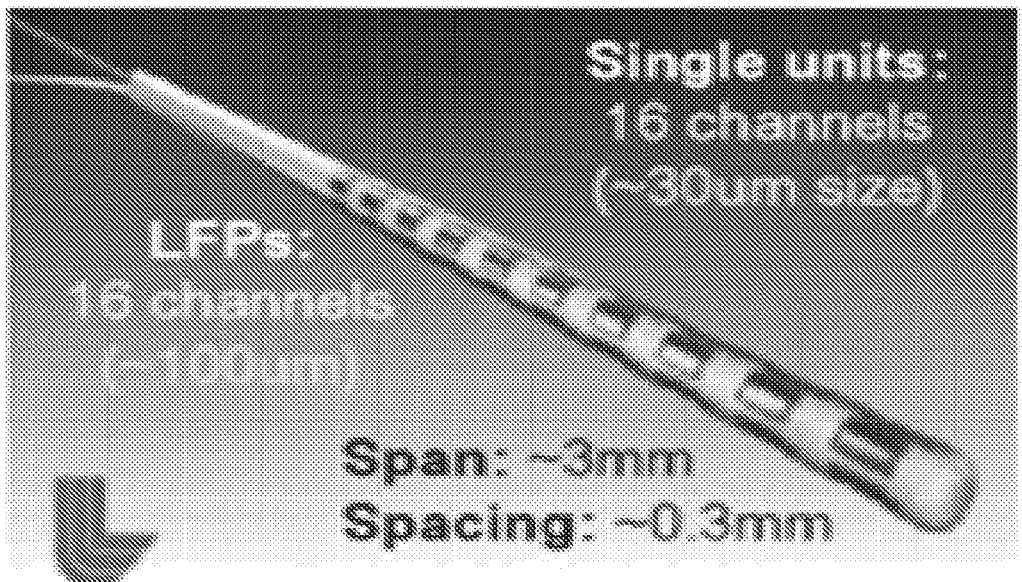

Some implementations include fabricating the stimulating and recording electrode arrays. Some implementations include a method for spiral winding of polymer electrode array around a DBS-style lead (FIG. 3C). In some implementations, the stylet is designed for ease of surgical implantation and to take advantage of surgeons' familiarity with DBS-like leads. In some implementations, the polyimide thin-film electrode array is encapsulated in silicone to reduce the immune response and improve long-term biocompatibility. In some implementations, the thin-film neural probe is fabricated in a polyimide substrate with sputtered platinum as the electrode material. Even though the density and Young's Modulus of polyimide is larger than brain tissue (~5 MPa), it has been shown to be extremely biocompatible when implanted at the cortical surface.

Some implementations include the use of state-of-the-art fabrication and electrochemical equipment dedicated to the processing and characterization of implantable devices.

In some implementations, stimulating and sensing ICs are integrated into miniaturized, hermetically-sealed packages that are permanently bonded to the sub-cortical array using rivet bonds. In some implementations, the size of these packages is on the order of 10×10×5 mm$^3$, allowing the ability to mount the package onto the skull. To achieve extreme miniaturization, in some implementations, advanced 3-D packaging technologies are used, borrowed from military-standard semiconductor processes to assemble active and passive IC components in a small form-factor. In some implementations, a combination of flip-chip bonding, wire bonding, stencil printing, and brazing is performed to integrate electronic components inside the package (FIG. 4). In some implementations, the complete system is used in an IDE submission to the FDA for a chronic neural interface for humans.

In some implementations, the implantable device is powered using wireless telemetry. In some implementations, an implantable coil is designed and fabricated using biocompatible materials and encapsulated in silicone. Delivering power to the implant without overheating the tissue while keeping the implant size small a challenge. In accordance with some implementations, the 64-channel implant requires ~2 mW of power. In order to meet all the constraints (distance between coils, coil size, required output power), the architecture is optimized to maximize power efficiency (e.g., power and control circuitry 500, FIG. 5). In some implementations, an active rectifier is used to compensate gate turn-on/off delay times of the power MOS devices and achieve a high conversion efficiency (e.g., greater than 80%). In some implementations, a multi-LDO V-regulator topology is adopted to mitigate interference across power domains. In some implementations, flipped-voltage-follower circuits are used as the regulator output stage. In some implementations, the high-voltage driver, needed for stimulation, achieves output voltages beyond the limits in standard technology nodes. In some implementations, a bidirectional, cascaded charge pump is used and also serves as negative-voltage generator for stimulation. For example, the circuit can be fully integrated in a 1V 40 nm technology and still offer voltages beyond 10V.

In some implementations, the power module requires an off-chip capacitor (~2 μF), allowing peak-to-average ratio of ~10. In some implementations, two tiny capacitors (e.g., 0201 capacitors) are used to deliver peak power during stimulation (e.g., ~10 mW). In some implementations, additional storage and bypass capacitors are used for the data path and the power recovery circuits. In some implementations, the feedback control mechanism ensures thermal control of the tissue and adjusts link parameters to maximize efficiency. The efficiency, speed and flexibility of the circuit is superior to all other proposed architectures.

Figure 10:
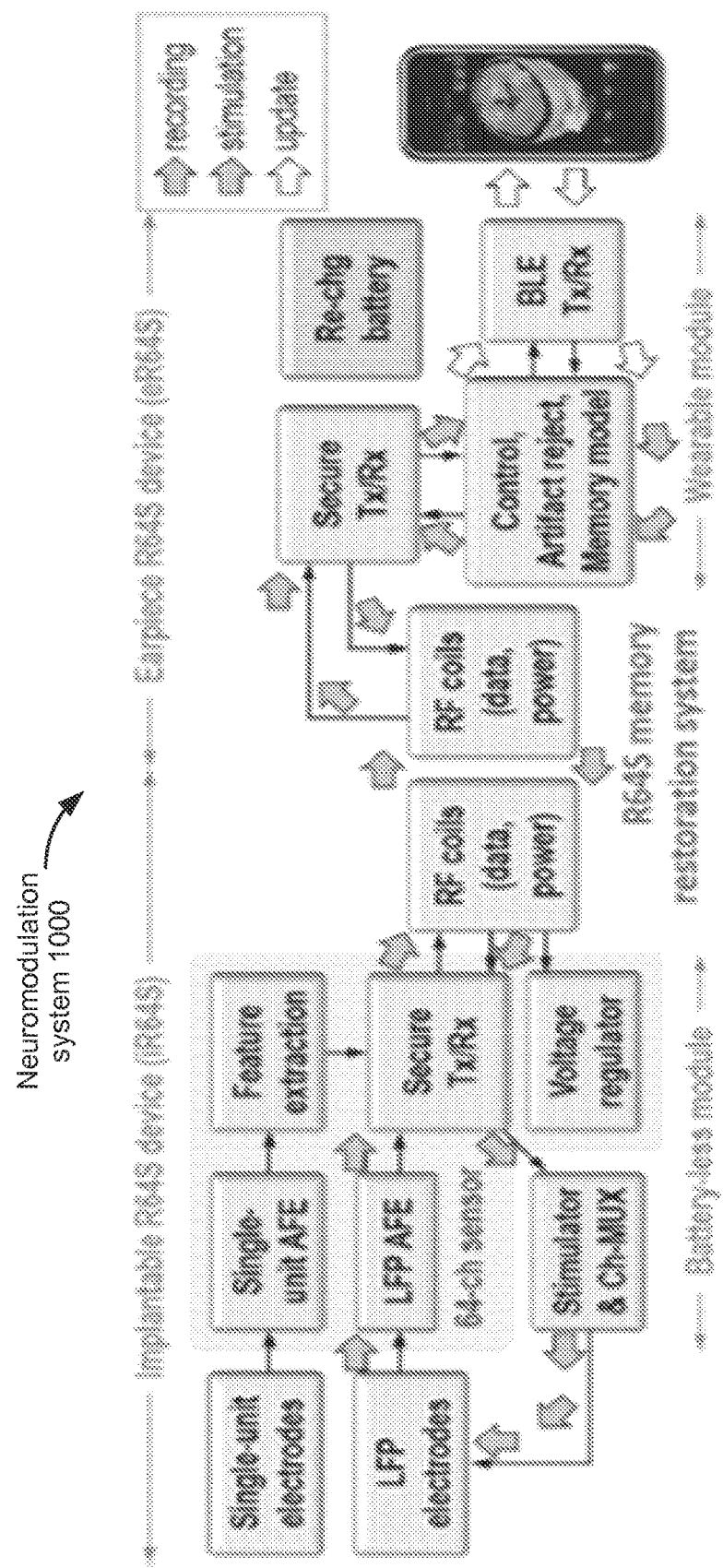
FIG. 10 illustrates an exemplary neuromodulation system, in accordance with some implementations.
Figure 11:
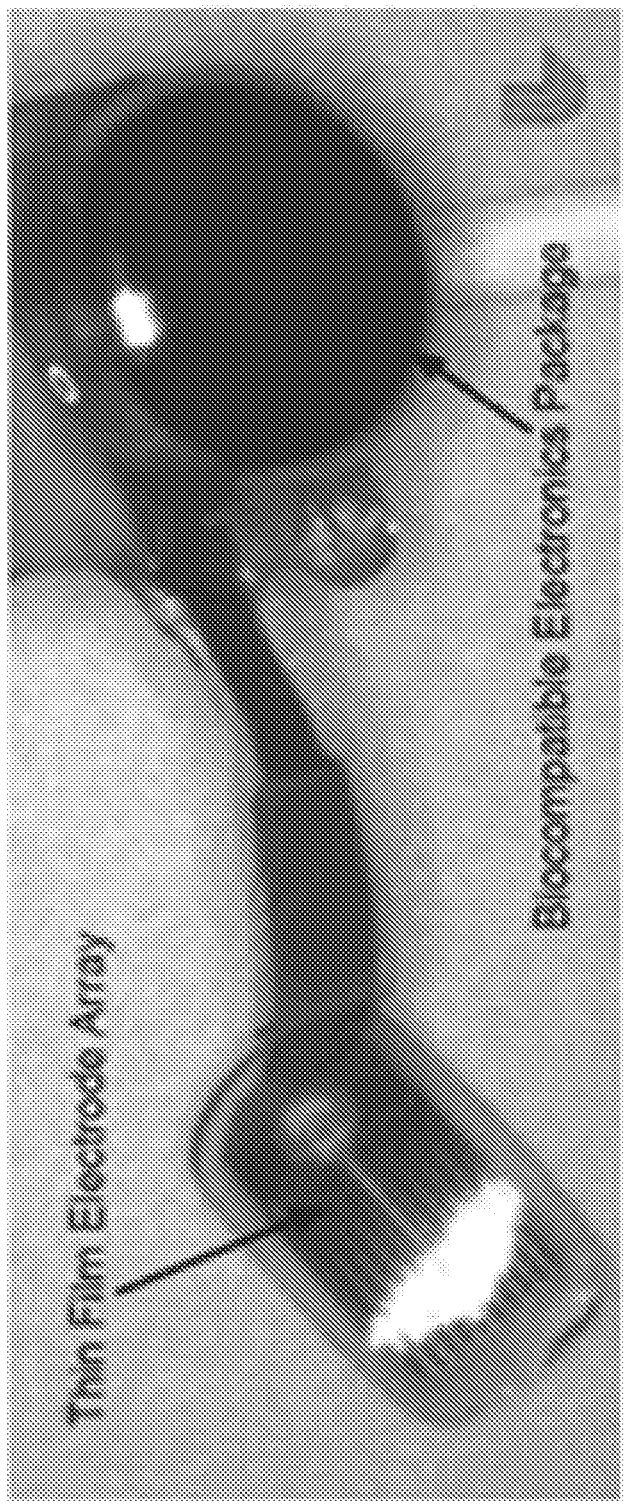
FIG. 11 illustrates an exemplary retinal prosthesis with hermetically-sealed electronics, in accordance with some implementations.

FIG. 10 illustrates a neuromodulation system 1000, in accordance with some implementations. In some implementations, neuromodulation system 1000 includes two secure wireless links: (1) the nearfield link between the implant and the earpiece; and (2) the wireless link between the earpiece and the external monitoring "hub" (e.g., cell phone or other wireless module). In some implementations, for the earpiece, available COTS products (e.g., BLE) are used to achieve a low-power encrypted 1 Mbps system. In some implementations, an energy efficiency of approximately 1 nJ/bit is realized for this wireless link. The near-field data link between the implant and the earpiece is a critical component in the neuromodulation system 1000.

In some implementations, the architecture for the near-field data link includes a narrow-band FSK system in one of the available FCC bands around 400 MHz (433 MHz ISM or the 402 MHz MICS). In some implementations, the power and data links include two co-centric loops on a single flexible substrate. The large loop serves as the power path and operates on the 13.56 MHz band. The smaller loop provides a quasi near-field channel between the implant and the external ear piece. For example, given the uplink (UL) data rate of ~1 Mbps and assuming a noise-limited channel, the link can operate with a Tx average power in the range of −25 dBm (assuming 4 MHz BW, 55 dB link loss, and 20 dB SNR) on an FSK-modulated channel. This means the Tx power in the implant is not be dictated by the power amplifier ("PA") and more so with overhead bias, the modulator, and processing in the Tx path. The FSK system also reduces peak-to-average requirements rendering the system more stable and reliable.

In some implementations, the architecture for the near-field data link includes a UWB system. For example, a UWB system with an uplink data rate of 30 Mbps and a target energy consumption of 40 pJ/bit, thus, requiring a TX power of 1.2 mW. The data rate and energy efficiency in this allows for significantly improved flexibility in extending the number of channels and/or to record at higher rates.

Figure 8:
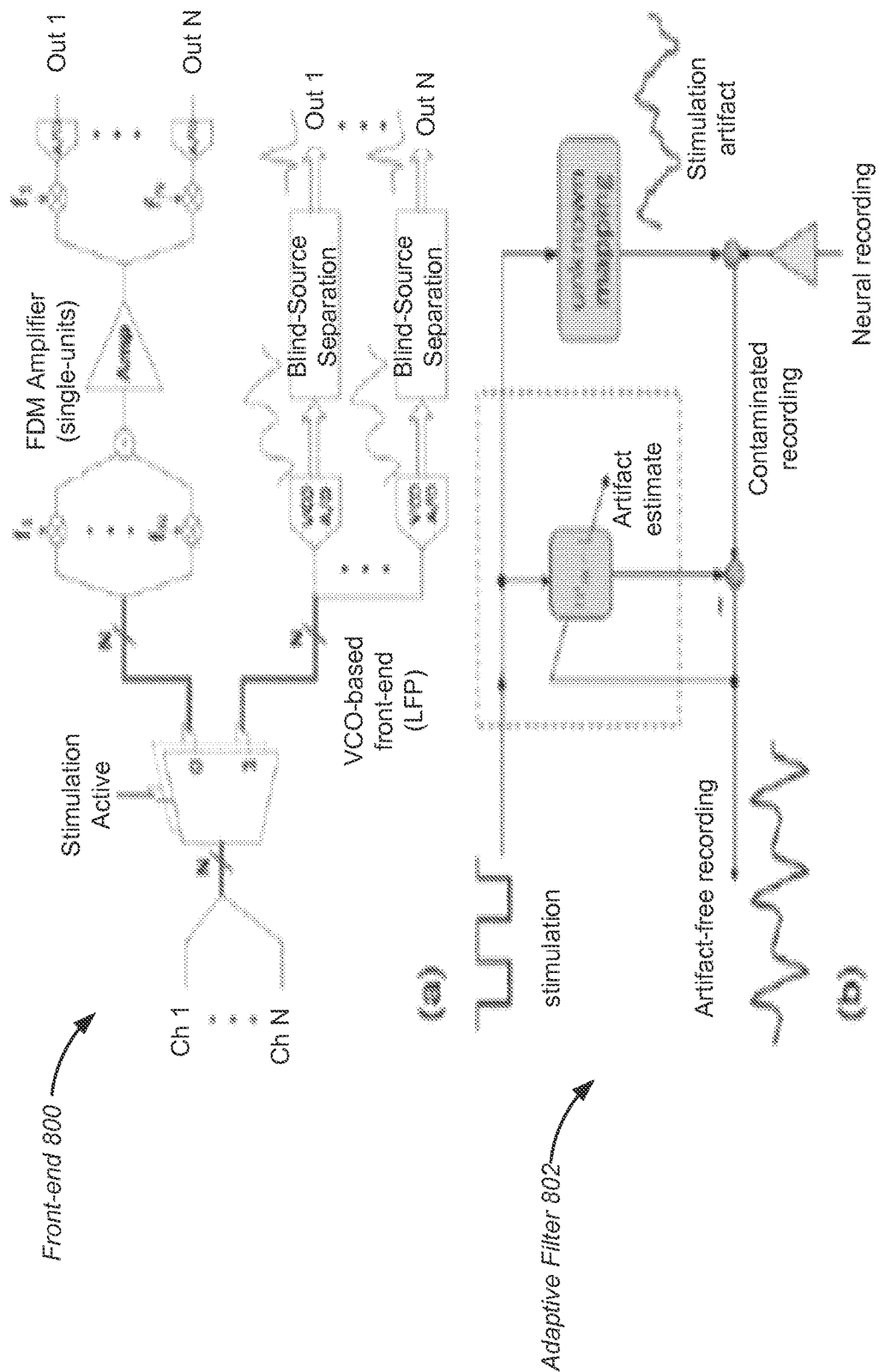
FIG. 8 illustrates an exemplary front end and adaptive filter for use with a wireless implant, in accordance with some implementations.

FIG. 8 illustrates front end 800 and adaptive filter 802 for use with a wireless implant, in accordance with some implementations. Recording low-amplitude (100 μV) signals in a closed-loop recording and stimulation system requires the signal chain to be robust to saturation by large stimulation artifacts. Conventional recording front-ends incorporate a high voltage-to-voltage gain and saturate for 5 mVp-p signals, leaving no hope for signal recovery under the presence of large (200 mVpp) stimulation artifacts. Realizing that the saturation of the signal chain happens due to the finite physical bounds on electrical voltage and current in an electrical circuit, the present disclosure includes design circuits that rely on voltage-to-phase conversion for amplifying and quantizing the signal, as shown in FIG. 8(a). In some implementations, the voltage-to-phase conversion inherent to the operation of VCO-based ADCs is leveraged to directly digitize the input, providing saturation tolerance for 200 mVp-p interferes, while providing a 1 µV quantization step size for the desired signal of interest. In some implementations, a low voltage current-starved VCO, discrete-time chopping, a duty-cycled design, and adaptive foreground non-linearity correction are used to implement the 16-bit ADC in less than 1 µW/ch for digitizing LFP signals. Due to the non-saturating nature of the ADC, some implementations include employing adaptive filters to eliminate stimulation artifacts from neural recordings, as shown in FIG. 8(a). An adaptive filter has the capability to effectively remove the stimulation artifact without prior knowledge of the precise mapping between the stimulation pulse and the recorded artifact. For example, if, on a first pass, one views the neural signals as noise, then adaptive techniques are used to estimate the unknown mappings, which in turn are used to clean the data, and so on. Moreover, it is also capable of tracking any variations that this mapping may have, thus canceling the artifact even as the shape and amplitude of the artifact changes with time. In some implementations, the VCO-ADC based front-end is used to record single units, but the power consumption of the ADC increases significantly due to the large bandwidth of the single-unit signals.

Some implementations include a revolutionary multi-channel amplifier that uses frequency-division multiplexing to share the frontend amplifier, thus saving power. For example, the multi-channel front-end consumes 0.8 µW/channel for both single-unit and LFP recordings. In some implementations, the two solutions are combined to operate in the power-optimized mode under normal conditions and a dynamic-range optimized mode under the influence of stimulation artifacts as shown in FIG. 8(b). In some implementations, the signal is recovered under artifacts up to 200 mV, representing a greater than 20× improvement compared to existing schemes.

In some implementations, the embedded processor inside the earpiece module hosts the adaptive filter for artifact removal, a programmable memory model, and a system/interface controller.

In some implementations, the stimulation circuitry includes a current-steering DAC that is digitally controlled and can provide bi-phasic currents up to 2 mA. In some implementations, a charge-balancing circuit neutralizes any excess charge on the electrode after stimulation. This ensures that there are no unwanted long-term effects like electrode oxidation. Tissue impedance of 10 kO at 1 kHz corresponds to an equivalent capacitance of 16 nF. For example, for a stimulation current of 2 mA applied for 50 µs, the peak swing at the electrode-tissue interface is 6.25V. In some implementations, for the DAC to operate as a current source with such large swings, charge pumps are used to generate appropriate supply and bias voltages. Since the stimulation power is a significant fraction of the total power, the efficiency of the charge pump needs to be as high as possible.

In some implementations, the verification activities described throughout this disclosure can proceed throughout the development process, even prior to integration of the custom neural recording and stimulation ICs. For example, electrode lead wire assembly undergoes a variety of in-vitro and in-vivo testing to establish efficacy and reliability. In some implementations, these tests include one or more of: (i) accelerated in-vitro flex testing demonstrating the lead wire is resistant to mechanical fatigue (100% lead wire survival following more than 20 million flexing cycles); (ii) FDA mandated ISO 10993 biocompatibility testing for fully implanted devices; (iii) chronic recording using animal models; (iv) accelerated in-vitro lifetime soak testing under constant electrode stimulation. In some implementations, the lifetime to a failure at 37° C. (body temperature) is extrapolated from the tests done at 87° C. using the Arrhenius relationship to validate five years of lifetime.

Some implementations include sterilizing the implantable components of the system using both Ethylene Oxide (EO) and high-pressure steam sterilization.

In some implementations, a 32-channel electrode array is fabricated, assembled, characterized, and tested for stimulation and recording. In some implementations, an IDE application is submitted for the fabricated electrode arrays. In some implementations, complete devices are assembled for testing and characterization. In some implementations, testing results of the complete system are submitted with the IDE application. In some implementations, complete devices are also assembled for human implantation following IRB and IDE approval.

Some implementations include the use of adult male Long-Evans rats (approximately 3.5 months old at the start of training) individually housed on a 12-hour light/dark cycle. In some implementations, animals are food restricted (e.g., 15-20 g of food per day) to maintain body weight. In some implementations, animals are allowed to access a restricted amount of water (e.g., 25-35 ml of water per day) after the behavioral session to maintain motivation. In some implementations, all experimental procedures are conducted in accordance with USA federal guidelines.

In some implementations, the VR system (e.g., virtual reality system 602, FIG. 6) includes a 61 cm diameter Styrofoam sphere that floats freely on an acoustically quiet air cushion. In some implementations, the ball rotation is measured by two orthogonally placed laser sensors, merged by a microcontroller, and used by custom software to change the surrounding visual scene. In some implementations, a one-to-one mapping between the rat's movements and the corresponding changes in the virtual environment is established. In some implementations, a micro projector projects visual stimuli on a convex mirror, which reflects the stimuli onto a cylindrical screen (e.g., a 300°, 68 cm diameter, 75 cm tall cylindrical screen made of white fabric). The VR system thus allows presentation of an undistorted visual scene in all directions including within 1 cm of the rat. In some implementations, a hinged harness holds the rat on the sphere. In some implementations, a stainless steel tube mounted in front of the rat dispenses liquid rewards (e.g., 10% sucrose water, 150 µl per reward) controlled by a software driven solenoid valve. In some implementations, the VR software is built in C++ using the Ogre 3D graphics engine and OpenAL. In some implementations, VR data, including the animal's (virtual) speed, position and heading, is recorded by the software (e.g., at a sampling rate of 60 Hz or greater).

In some implementations, speakers (e.g., 7 SS-B1000 speakers) are placed outside the screen in a hexagonal+ center speaker distribution, all in an acoustically shielded, 3×3 m room. In some implementations, Higher Order Ambisonic sound is generated (e.g., using Blue Ripple's Rapture3D openAL libraries). In some implementations, an HD audio/video card (e.g., a Radeon 5670 card) is used to output audio channels over HDMI to an AV Receiver (e.g., a STRDH520 receiver) which is then sent to the speakers. This hardware, in conjunction with software, is capable of generating realistic 2-dimensional spatial auditory stimuli by reconstructing the sound field in the center of the speaker array. In addition, the use of the thin fabric screen ensures that there were no distortions in the acoustic stimuli.

In some implementations, a software-driven solenoid is placed outside the experimental room and that controls the delivery of liquid rewards (e.g., 10% sucrose) through a tube (e.g., a stainless steel tube) mounted in front of the rat. In some implementations, a capacitive touch circuit is connected to the delivery tube to detect when the rat contacted the reward tube, providing a temporally precise (e.g., ~16 ms) estimate of reward checking and reward consumption. In some implementations, the capacitive touch sensor read by the same microcontroller that also reads the laser sensors.

In some implementations, the VR software package is custom-built (e.g., in C++ using the Ogre 3D graphics engine and Open Audio Library). In some implementations, virtual worlds are constructed using xml files. In some implementations, world type, track boundaries, reward types, reward locations, teleportation, event triggers, and visual and auditory cues are all defined in the xml file, allowing easy creation and modification of environments. In some implementations, pre-distortion of the visual world is handled through custom mapping files which take into account the screen geometry, mirror curvature, and pixel location. In some implementations, spatial and non-spatial auditory stimuli are handled through OpenAL and are capable of driving any number of speakers in any arbitrary speaker configuration. In some implementations, the software connects (e.g., through USB) to the reward delivery system, motion sensors, and capacitive touch sensor. In some implementations, 3 axis rotational positions of the treadmill, virtual position, view angle, timestamps, and trigger events are saved. In some implementations, event triggers include reward dispensing, teleports, cue hiding/revealing, and other events defined in the xml file.

In some implementations, the virtual environment includes a 200 cm diameter platform 1 m above the floor and centered in a 3×3×3 m room. In some implementations, a polka dot pattern on the platform floor provides spatially non-selective texture and optic flow. In some implementations, a 30×30 cm white grid on the black floor provides parallax-based depth perception between the platform and the floor. In some implementations, distinct distal visual cues cover all 4 walls and provide the only spatially informative stimuli in the VR, as shown in FIG. 6(b). In some implementations, the rats forage on a platform (e.g., a 200 cm diameter platform) to find a predetermined but unmarked spatial location to obtain liquid rewards.

In some implementations, upon reaching the hidden reward zone the rats are "teleported" to one of the four randomly selected start positions at the edge of the track and the new trial begins with the rats having to once again find the hidden reward zone. In some implementations, to determine multisensory navigation both distal auditory and distal visual stimuli are used. In some implementations, to determine multimodal navigation both spatial occupancy and reward checking rate as a function of space are measured. In some implementations, all experiments/trials are conducted in identical acoustically- and EMF-shielded rooms.

In some implementations, after habituation, animals are trained to run for randomly cued positions to obtain rewards, but with different visual stimuli than the ones used in multimodal navigation task. In some implementations, this is done to control for the amount of experience on the final version of the task. For example, a 10 cm wide and 100 cm long visual pillar indicates the cued reward locations in these cued tasks. In some implementations, the pillars are eliminated in the memory-based navigation task. In some implementations, entrance into the active reward location triggers a tone and the liquid reward delivery.

In some implementations, rats showing sufficient performance in the VR task are implanted with hyperdrives (e.g., 25-30 g custom-built hyperdrives) containing up to 22 independently adjustable tetrodes (e.g., 13 µm nichrome wires) positioned over both dorsal CA1 or the entorhinal cortex. In some implementations, surgery is performed under isoflurane anesthesia and heart rate, breathing rate, and body temperature are continuously monitored. In some implementations, analgesia is achieved by using Lidocaine (e.g., 0.5 mg/kg, sc) and Buprenorphine (e.g., 0.03 mg/kg, ip). In some implementations, multiple 2 mm-diameter craniotomies are drilled using custom software and a CNC device with a precision of 25 µm in all 3 dimensions. In some implementations, dura mater is removed and the hyperdrive lowered until the cannulae are about 100 µm above the surface of the neocortex. In some implementations, the implant is anchored to the skull with 7-9 skull screws and dental cement. In some implementations, the occipital skull screw is used as ground for recording. In some implementations, rats are administered 40 mg sulfamethoxazole and 8 mg trimethoprim in drinking water and ~10 mg/kg carprofen (e.g., Rimadyl bacon-flavored pellets) one day prior to surgery and for at least 10 days during recovery.

In some implementations, the tetrodes are lowered gradually after surgery into the hippocampus or the entorhinal cortex and allowed to stabilize over the region of interest. In some implementations, positioning of the electrodes in CA1 is confirmed through the presence of sharpwave ripples during recordings, and through histology after experiments. In some implementations, signals from each tetrode are acquired by one of four 27-channel headstages, digitized (e.g., at 40 kHz), bandpass-filtered (e.g., between 0.1 Hz and 9 kHz), and recorded continuously. In some implementations, each recording session includes hour-long baselines pre- and post-task to ensure stability of units and to measure HEC activity during sleep. In some implementations, during these baseline/sleep sessions, rats are allowed to rest in a box outside the task apparatus.

In some implementations, all analyses are performed using custom code (e.g., written in MATLAB). In some implementations, circular statistics are computed (e.g., using the CircStat toolbox). In some implementations, significance tests between two distributions of linear variables are performed using the nonparametric Wilcoxon rank-sum test, and tests between circular variables are performed using the Kuiper test. In some implementations, tests for populations significantly different from zero are performed using the nonparametric Wilcoxon signed-rank test.

In some implementations, start and end times for all trials are determined by a minimal speed threshold (e.g., 5 cm/s), data during times while the rat was stationary is not included in the analysis, except for the calculation of goal-cell activity. In some implementations, a unit is considered track active if its mean firing rate on track is at least 0.5 Hz. In some implementations, spatial firing rates are computed using a 5 cm Gaussian smoothing kernel on occupancy and spike histograms with 5 cm wide bins. In some implementations, a place field is defined as a region where the firing rate exceeded 5 Hz for at least 5 cm. In some implementations, the boundaries of a place field are defined as the point where the firing rate first drops below 10% of the peak rate (within the place field) for at least 5 cm. In some implementations, a unit is defined to be significantly active in a trial if the number of spikes fired in that trial are not below the 5th percentile as calculated by equation 2:

$$\text{Poisson}(\Sigma_i \lambda_i^{T/t} O_i^t) \quad \text{Equation 2}$$

where $\lambda_i^{T/t}$ is the firing rate in the i-th bin, computed over all trials (T) except the one under consideration (t), and is the occupancy time in the i-th bin on the trial under consideration.

In some implementations, the information content of a single unit rate map (in bits) is measured as shown in Equation 3:

$$I = \sum_i^L P_i \frac{\lambda_i}{\bar{\lambda}} \log_2 \frac{\lambda_i}{\bar{\lambda}}, \text{ where } P_i = \frac{o_i}{\sum_j^L o_j}, \text{ and } \bar{\lambda} = \sum_i^L P_i \lambda_i. \quad \text{Equation 3}$$

In some implementations, the significance of spatial information for each unit is assessed using a trial shuffling procedure. In some implementations, spiking and occupancy information is circularly shuffled by a random amount for each of the trials, and the information content of the resulting rate map is computed. In some implementations, this procedure is repeatedly and independently applied to the two running directions, to generate a null distribution of 500 information content values for each direction. In some implementations, a unit is considered to have significant spatial information if the information content of its true rate map exceeds that of 95% of values in the null distribution for at least one of the two running directions. In some implementations, the sparsity of a single unit rate map is defined (with L the number of spatial bins) as shown in Equation 4:

$$S = \left(1 - \frac{1}{L} \frac{\left(\sum_i^J \lambda_i\right)^2}{\sum_i^L \lambda_i^2}\right) \left(\frac{L}{L-1}\right) \quad \text{Equation 4}$$

Thus defined, S ranges between zero (for a uniform rate map) and 1 (for a delta function rate map).

In some implementations, a multi taper power spectrum for each LFP is calculated during running behavior. In some implementations, to avoid potential contamination from noise, only LFPs exhibiting clear theta (e.g., defined as a theta (4-12 Hz) to delta (0.01-4 Hz) power ratio exceeding 1/3) are considered for analysis of either theta frequency or phase precession. In some implementations, each LFP is then filtered (e.g., 4-12 Hz, 4th order Butterworth) and theta frequency is computed using at least one of four methods: (1) cycle detection using Hilbert transformed phase jumps; (2) the derivative of Hilbert transform phase; (3) the short time Fourier transform; and (4) a method based on the Kalman filter. In some implementations, the quality of phase precession is measured using the circular linear correlation coefficient shown in Equation 5:

$$\rho_{ci} = \sqrt{\frac{r_{cx}^2 + r_{sx}^2 - 2 r_{cx} r_{sx} r_{cs}}{1 - r_{cs}^2}}, \, r_{cx} = corr(x, \cos \alpha), \quad \text{Equation 5}$$

-continued $$r_{sx} = corr(x, \sin \alpha), r_{cs} = corr(\sin \alpha, \cos \alpha)$$

In some implementations, spiking frequency of single units is calculated by detecting the peak in filtered spike train autocorrelations.

FPI is a general brain movement injury induced by fluid pulse that may include components of more severe damage (e.g., subdural hematoma-SDH, cortical contusion, diffuse axonal injury-DAI) in more severe cases or minimal cellular death but widespread neurometabolic dysfunction (concussion, blast, mild DAI). This model is associated with declarative/spatial memory impairments as well as loss of experience-dependent neuroplasticity. The underlying substrate for these memory impairments have been shown to be linked to impaired hippocampal glutamatergic function using molecular, electrophysiological, behavioral and imaging methods.

CCI is a focal TBI with diffuse characteristics induced by direct impact to the dura which best resembles more severe TBI with cortical contusion and intracranial hemorrhage. In this model there may or may not be secondary damage to the hippocampus but deficits in declarative memory have been reported even in the absence of overt hippocampal pathology.

CHI is a more recent model that induces memory impairments, axonal injury and may be repeatable to mimic multiple concussions or blast injuries sustained by human patients. It also induces widespread neurometabolic dysfunction in the absence of overt cell death, and the timing of repeat injury is related to the severity of the long-term deficits, resembling human experience with repeat CHI/concussion.

In some implementations, 2 age groups are included, PND35-46 which corresponds to late adolescence/late teens as well as PND90 which is a fully mature adult. Both ages are relevant to the main epidemiological peak in TBI risk in humans for both civilian and military personnel. However, there is evidence that the younger brain may have distinctions (e.g., loss of plasticity, less myelination, less cell death with mild TBI) from injuries in adults. Thus, some implementations include using 2 age groups to determine the magnitude and importance of these developmental characteristics. In some implementations, the animals are studied longitudinally at 3 times points (e.g., post-injury day-PID 4, 14 and 30).

The novel object recognition task is both a measure of working memory and declarative memory. Advantages include that the task is not rule based, has little stress, and relies on the animals' inherent exploratory tendencies. It also clearly shows deficits in all 3 experimental TBI models utilized herein. Given the relatively low intensity of novel object recognition testing, it is possible to incorporate this task longitudinally. In some implementations, spatial memory is the second behavioral paradigm to be measured. There are several specific methods to investigate this. The Morris Water Maze (MWM) has been most widely utilized in the field of trauma and by our group, and clearly shows TBI-induced impairments in both spatial learning and memory. Despite these advantages, because the MWM requires the animals to swim in a water filled tank, it creates some challenges for recording electrophysiological activity concurrently using tethered or head-stage mounted hardware. The Barnes Maze is a dry-land version able to test spatial learning and memory. It has been used by colleagues in the field to demonstrate electrophysiological correlates of spatial memory impairment after lateral FPI. In some implementations, this test is performed in separate groups at each of the above post-injury days (e.g., PID 4, 14, and 30).

In some implementations, conventional structural, diffusion tensor imaging (DTI) and resting state functional MRI (rs fMRI) are obtained on a subset of the experimental animals (e.g., using a 7T Bruker MRI scanner). For example, resting State (RS) FMRI-A 7 Tesla, Bruker Console, Oxford magnet with Bruker 'rat S116' gradients (400 mT/m), a birdcage transmit and receive-only surface coil are used to acquire data. In some implementations, rats are sedated with dexmedatomidine (bolus i.v. 0.05 mg/kg, then continuous subcutaneous infusion 0.1 mg/kg/hr), and controlled for temperature, ventilation rate and end tidal PCO2. In some implementations, single-shot, echo-planar, gradient echo data is acquired (128×64 matrix in a 30×30 mm field of view, 14×0.75 mm slices, repetition/echo time (TR/TE)=2000/30 ms) for a period of 20 mins (600 volumes). In some implementations, data is entered into a group-wise independent component analysis (e.g., using GIFT software constrained to 30 components). In some implementations, from the group averaged data, the major sensorimotor cortical (S1, S2, M1/M2, cingulate, parietal) sub-cortical (caudate putamen, thalamus) and hippocampal circuit components (dorsal and ventral hippocampus, prelimbic frontal cortices, cingulate cortex, retrosplenial cortex) is manually identified (via a co-registered 3-dimensional segmented atlas volume) and then data from each component is back-projected onto the original individual brain. In some implementations, Gaussian-smoothed using a full width half maximum kernel of 8 mm and the resulting residuals are entered into a regression analysis against the mean blood-oxygen-dependent time-course obtained from the seed region-of-interest (ROI) to calculate the voxel-wise Pearson correlation coefficient.

In some implementations, network analysis of circuits (subdivisions of sensorimotor cortex, M1, M2 cortex, thalamus) is analyzed (e.g., using Conn Tool) using a rat segmented atlas. In some implementations, for DTI data acquisition, a 4-shot, echo planar, spin-echo sequence is used to acquire 5 b0 images and 30 diffusion-weighted images (b value=1000 s/mm$^2$) with gradients evenly spaced to optimally sample the primary diffusion vector. For example, Δ=20 ms d=3 ms; TR/TE=6250/32 ms; 2 averages, 25×0.75 mm slices, 128×128 matrix in a 35×35 mm field-of-view.

In some implementations, at the conclusion of the longitudinal animal studies, half of the rats are transcardially perfused with 4% paraformaldehyde and brains frozen for subsequent histological and immunohistochemical analyses. In some implementations, frozen sections are cut at 40 microns and thaw mounted for cresyl violet or hematoxylin-eosin staining. From these sections gross morphology is ascertained as well as confirmation of electrode placement locations.

In some implementations, the other half of the rats undergo fresh brain region harvesting, with immediate dissection of brains into prefrontal, frontal, parietal and occipital cortex, hippocampus and cerebellar samples. In some implementations, these are homogenized and frozen for subsequent molecular analysis using immunoblotting. In some implementations, currently measured molecules include NMDA receptor subunits (NR1, NR2A, NR2B), AMPA receptor subunits (GluR1, GluR2), signal transduction molecules (CaMKII, µCaMKII, CREB, µCREB) and Neurotrophins (BDNF)

Regarding non-human primates, in some implementations, behavioral tasks have been designed to test three forms of memory. In some implementations, these tasks are based on tasks used on psychophysical subjects or patients, but have been modified to better suit the behavior of non-human primates. In some implementations, all non-human primates are housed in vivarium. In some implementations, for training, all animals have scleral search coils and head holder devices implanted under aseptic conditions. In some implementations, animals on study are water scheduled—receiving most, if not all, of their water intake in the lab. In some implementations, animals are brought to the lab in a primate chair. In some implementations, the behavioral tasks are controlled via a computer (e.g., running REX software on QNX) and the stimulus images are created in VEX. In some implementations, eye positions are monitored by Riverbend or DNI coil systems and are recorded at 1 kHz throughout all tasks. In some implementations, all animals are trained to perform standard fixation and saccade tasks.

Task 1—Visual Preferential Looking Task.

Humans and non-human primates tend to prefer to look at novel items more than repeated items. A task takes advantage of this bias by presenting a sequence of stimuli and measuring the time the animals spend examining each stimulus. It requires very little training and has successfully been used to examine responses in monkey hippocampus and is known to be impaired after lesions of the hippocampus in both monkeys and humans. In some implementations, the animals begin a trial by fixating a central cross. In some implementations, after 500-750 ms, an image is placed in the center of the screen. In some implementations, it remains until the animal stops looking at the image or after 5 s. In some implementations, blocks of 6, 8 or 10 trials are used, during which no rewards are given. In some implementations, between blocks, the animals perform a number of simple visually guided saccades, which are rewarded. In some implementations, most of the images are novel, but between 1 and 3 images within a block can be a repetition of an image seen earlier in the block. In this task, gaze tends to stay on the novel images significantly longer than on the repeated images. In some implementations, the metric for improved performance is a significant reduction in looking time at repeated images tested with stimulation and without stimulation. This may be easiest to quantify for repeated images that are presented far apart within the block.

Task 2—Scene Recollection Task.

In some implementations, a task is based off the visual preferential looking task used to test patients. The task tests whether the animal can recall which of two test images come from a scene that it has examined within the block. The animal begins a trial by fixating a square point in the middle of the screen. In some implementations, after 500-750 ms, the fixation point disappears and a scene is presented on the screen. In some implementations, the scene is a natural image or an artificial image constructed by the virtual reality software. In some implementations, the animal is given a short time (e.g., 3-5 s) to freely scan the scene, after which the scene is removed. In some implementations, this is repeated two more times with 500 ms inter-stimulus intervals, after which the fixation point reappears. In some implementations, 500 ms later two small images are presented just to the left and right fixation; one of the images is a section of one of the three scenes the animal just saw, the other is a section of another scene (which the animal may or may not have seen previously). In some implementations, a yellow square is placed just lateral to each image. In some implementations, to get the reward, the animal must make a saccade to the yellow square beside the image that came from one of the scenes it just saw. In some implementations, the animal is allowed to freely scan the screen, but once the eyes go to one of the yellow targets or leaves the screen, the trial ends. If gaze goes to the correct yellow square the animal is rewarded. In some implementations, performance in this task is measured as the percentage of correct choices. In some implementations, the metric for improved performance is a significant increase in percent correct with stimulation. By using distracters (the incorrect target stimulus) that the animal has seen before, but not within the current trial, the effect of stimulation on memory interference can be examined.

Task 3—Associative Memory Task.

In some implementations, a task is based off the faceplace associative task used to test patients. It tests whether the animal can recall which of two objects (including faces) were seen associated with a specific scene. The task structure is similar to the scene recognition task; however an image of an object is also placed within each scene. In some implementations, the object has a square border which clearly defines it as not belonging to the scene. In some implementations, as in the scene recognition task, three scene/object stimuli are presented within 9-15 s. In some implementations, after the third scene/object pair, the fixation point reappears. In some implementations, after 500 ms, a smaller version of one of the three scenes is place in the upper half of the screen and two objects are presented to the left and right, just beneath the fixation point. One of the objects was the object associated with the scene, the other could have been presented within the trial or could be novel, but was not associated with the scene. In some implementations, two yellow squares are placed to the side of each object and the animal is rewarded for looking at the yellow square next to the associated object. In some implementations, the metric for improved performance is a significant increase in percent correct with stimulation. In some implementations, the impact of stimulation on performance is examined when distracters are novel, seen previously within the trial (but not associated with the test scene) or seen previously within another trial.

Task 4—Spatial Associative Memory Task

In some implementations, this task is similar to the associative memory task, but examines the animal's ability to recall where the object was within the scene. In some implementations, the structure is almost identical to the associative memory task, however during the testing phase, after the third scene/object pairing, the full scene is presented and two copies of the associated object are presented: one in the location where it was presented during the examination period and one in an equal, but opposite location across the vertical and/or horizontal meridian. In some implementations, as in the previous tasks, two large yellow squares are placed lateral to the two object locations and the animal is rewarded for making an eye movement to the yellow square beside the correctly placed object. In some implementations, the metric for improved performance is a significant increase in percent correct with stimulation.

In some implementations, initial testing of electrodes is performed using standard recording techniques. In some implementations, pre-surgery anatomical MRIs are taken to precisely identify the location of the hippocampus and entorhinal cortex. In some implementations, in a second surgical procedure, a recording chamber is placed in such a position to allow access to both structures with a single electrode; and a 19 mm diameter craniotomy is made in the center of the chamber. In some implementations, the recording electrodes and recording hardware are identical to those that are used in the patients, thereby allowing testing of the entire system. In some implementations, all animals with implants are monitored daily and the margins around the implants and the exposed dura are cleaned or maintained at least 3 times a week. In some implementations, the inside of the recording chamber is cleaned using a standard chamber-cleaning protocol.

In some implementations, data management, sharing and delivery and statistical support services are provided by SIStat, the biostatistics and data management core in UCLA's Semel Institute for Neuroscience and Human Behavior, and are used by all projects and cores. In some implementations, the data management, sharing and delivery and statistical support services include one or more of: (1) developing a centralized research database and dissemination system; (2) providing data security and quality assurance; (3) coordination of study data from different projects, platforms and repositories; and (4) provision of statistical consulting and analytical services.

In some implementations, all data is coordinated, collated, tracked and made accessible (e.g., through a centralized program database), with different levels and schedule of access for various types of users (e.g., program investigators, DARPA staff, and public access). In some implementations, a demonstration website displaying many of the features currently available to Center researchers is generated and can be accessed. In some implementations, all requests for data sets are made through a online query system and must be approved (e.g., by a PI and Publication Committee). In some implementations, the query system includes a master registry table, which indicates which measures and protocols are available for which subjects. In some implementations, the table can be sorted and searched by key characteristics (e.g., demographic features, diagnosis, associated imaging, protocols, intervention). In some implementations, standard datasets are generated automatically and posted for download by the requestor; more specialized requests are prepared, checked and distributed (e.g., by SIStat staff). A centralized system permits ready on-line reporting to all investigators, program sites, performer groups, and government agencies; enhances project management and quality assurance; gives researchers easy access to data and other project resources in real time; and facilitates cross-project analyses and collaborations. In some implementations, data can be entered into the system from any internet portal without special software requirements. In some implementations, built-in tools enable direct export of data files in all standard formats. In some implementations, additional analytical, management and training tools are developed to meet specialized needs. In some implementations, because in the setting of a dynamic data system, it can be difficult to replicate previous results with data that is added, edited, or corrected; snapshots of all the data sets distributed for analyses and corresponding queries are permanently preserved. In some implementations, all systems and tools are located on secure servers; are protected by encryption (e.g., 128 bit SSL); and secure socket layer technology is used for sensitive web transactions and feature a hierarchical system of password protected logins, allowing differential access to respective users. In some implementations, patient data is accessible only in a coded format based on study IDs to protect their identities.

In some implementations, for data collected with the NeuroPace RNS device, a secure HIPAA-compliant infrastructure is used for sharing the patient data. In some implementations, data is collected by commercial and IDE RNS® Systems, and shared when each patient is being studied. In some implementations, identifiable patient data is shared in a secure HIPAA-compliant manner.

Some implementations include development of a customized online trial management, data collection and communication system. In some implementations, the system incorporates the subject registry, administrative tools (for recruitment, scheduling and tracking of subjects), the annotated and searchable master data dictionary, and a centralized database, which allows for both direct entry of data from paper forms or interviews as well as electronic upload and merging of specialized data from other sources. In some implementations, electronic case report forms, protocol deviation forms and tracking of adverse events and medications or treatments are included. In some implementations, the systems has built in quality assurance processes including double entry to verify data correctness; automatic computation of derived variables; and validity testing such as logic and outlier detection to maximize data quality.

In some implementations, information about therapy delivery, including device serial and model numbers, and the date and location of events is tracked and made available for each subject. In some implementations, the availability and accessibility of all experimental data on a subject-by-subject (rodents, non-human primates, and humans) basis is catalogued, including one or more of: task performance and associated annotations, neurocognitive and psychiatric scales, brain mapping studies (with appropriate annotation and timing), invasive electrophysiological and neurochemical studies, and processed data (with annotation) at all time points for each subject. In some implementations, the data dictionary includes definitions; valid values; purpose and method of collection; and potential analytical pitfalls for all measures to ensure consumers have sufficient information to use the data appropriately. In some implementations, copies of study forms, instruments and protocols along with data processing algorithms and software (source code and executables) is made available. In some implementations, in addition to the trial management and data collection platforms, the system includes an online communication and dissemination platform featuring both an open website, where external researchers and the general public can learn about the investigators and projects, view publications and access shared reports and resources, and a private site where project investigators and members can post and interactively work on analyses, papers and presentations.

In some implementations, core reports (e.g., recruitment targets, tracking of incomplete or missing data and/or visits, adverse event and protocol deviation summaries for the DSMB and sponsoring agency, key descriptive statistics) are automatically generated by the system, updated in real time and transferred on a monthly basis to all key monitoring boards. In some implementations, automatically generated monthly (or on-demand) reports including all pertinent subject data are generated and submitted to DARPA. In some implementations, this includes coded de-identified data on a subject-by-subject basis including demographic and diagnostic data, pertinent dates, site information, neurobehavioral, neurocognitive, and psychiatric scales (at identified time points before and after intervention), raw and processed imaging data, raw and analyzed electrophysiological signals, interventions (including device serial number and stimulation patterns), key annotations including task timing and time-stamped behaviors, and patient outcomes. In some implementations, data is submitted in a way such that it is appropriate for analyses and interpretation.

In some implementations, the reports also include data on testing, development, and validation of the neuromodulation device. In some implementations, such reports are made available to DARPA performer's group at least quarterly or on demand. In some implementations, data is made accessible to the public after publication or at the request and approval of DARPA. In some implementations, data access and reports will continue for the public indefinitely.

In some implementations, developed rodent data analysis routines and computational model simulations dare shared with participating PIs so that the protocols for effective stimulation for RAM can be developed and tested in TBI models and primates prior to use in humans. In some implementations, once these results are well tested or published they are made available to other scientists at large using similar mechanisms as those described above.

In some implementations, all animal experimental data is collected in the Neurotrauma lab. In some implementations, ultimately, all relevant results are submitted for peer-reviewed publication in the medical and engineering literature.

Unlike other cortical areas, the medial temporal lobe is a brain region, which is clearly related to declarative memory function. Direct manipulation of this circuitry, in particular of the hippocampal-entorhinal cortex network offers a unique opportunity to influence learning and memory performance. Interestingly electrical stimulation of the hippocampus proper has been found to interfere with retrieval of information.

However DBS of the entorhinal area has been recently shown to enhance spatial memory in humans when DBS is provided during the learning phase. It is likely that stimulation of the entorhinal area may enhance hippocampal dependent memory because of close proximity of electrodes to the perforant pathway. Some implementations include utilizing advanced technology such as high-resolution diffusion tensor imaging, which can elucidate the exact area of entorhinal DBS placement within humans to determine proximity to the perforant pathway.

DBS of various other regions outside the MTL (e.g., anterior nucleus of the thalamus, hypothalamus, and septal nucleus, or even the vagus nerve) that have efferent and afferent connections to the hippocampus has been shown to enhance memory. However, whether the nature of this memory enhancement from DBS of these areas is due to overall increases in attention, arousal, or perceptuomotor function, however, is still unclear. Although results show that entorhinal DBS-induced memory enhancement is not due to enhancement of perceptuo-motor functions, other stimulated regions (e.g., vagus nerve) may affect memory through these or other alternative cognitive functions.

Direct macro-electrode DBS of the hippocampus generally shows disruptions in memory. It is possible that the use of macroelectrodes and thus stimulation of a large population of hippocampal neurons especially when given above the threshold to elicit after-discharges may disrupt local neuronal circuitry necessary for successful learning. Some implementations include determining how large the population of stimulated hippocampal neurons are actually need to be in order to reach threshold for behavioral changes.

Alternatively, it may not be the actual number of neurons stimulated but the nature of the stimulation that could most strongly affect memory. Recent studies in rodents show that when hippocampal electrical stimulation matches hippocampal input activity with respect to both spatial and temporal firing patterns, memory enhancement can result. Furthermore, optogenetic reactivation of hippocampal neurons that are activated during learning leads to enhanced memory expression. Thus, direct stimulation of the hippocampus can lead to both disruption and enhancement of memory, depending on the precise effect stimulation has on underlying neuronal activity. The use of specific and physiologically meaningful hippocampal stimulation combined with entorhinal afferent stimulation is hypothesized to be more likely to enhance memory.

Modeling studies of HEC system in regard to memory formation have largely focused on the recurrent network in CA3, starting with early works of David Marr followed by the Hopfield attractor networks. However, in recent years it is becoming increasingly clear that the recurrent connections within CA3 are not very extensive. Further, these CA3 based theories do not take into account the contribution of other crucial parts of the HEC circuit to memory formation, especially the contribution of CA1. Further, these theories do not take into account the computational implications of cellular memory in the entorhinal cortex or the segregation of object and place representations between different sub-regions of the entorhinal cortex. Finally, these computational theories do not usually consider the crucial contribution of inhibition to learning. The present disclosure addresses these gaps in our knowledge by developing computational models that include specific contribution of all parts of the HEC system, the biophysical properties of these elements, and behavioral correlates of their activity patterns.

There are a few FDA-approved, commercially available, human implantable systems for neural stimulation and recording. For example, both Medtronic and Neuropace have indwelling neuromodulation systems. Both are Deep Brain Stimulation (DBS) systems, capable of stimulating and recording from multiple contacts to treat motor disorders and epilepsy. Over the last decade, applications of DBS therapy have expanded in clinical trials to treat other neuropsychiatric and neurologic disorders, such as depression and Parkinson's disease. Despite the decades-long use of DBS therapy and the increasing list of disorders to which it can be applied, the mechanism by which DBS effectively works is still largely unknown.

For sub-cortical stimulation and recording, silicon-based neural interfaces are often employed. Several notable silicon-based neural interfaces (e.g., Blackrock Microsystems, Neuronexus) have been used over the last two decades. Despite some medium-term success of various types of penetrating arrays, no method has been successful at demonstrating a long-term functional neural interface from these silicon neural interfaces. The electrode failure is often attributed to mechanical mismatch between the rigid device material and cortical tissue as well as the persistence of a foreign body in the neural tissue.

A comparison of the state-of-the-art in wireless data transmission shows that UWB enables highly efficient data transmission. For example, an IR-UWB transmitter using OOK/PPM modulation with an energy efficiency of 35 pJ/bit and a data rate of 46.1 Mbps requiring a total TX power of 1.6 mW has been demonstrated. A narrow-band architecture with FSK modulation has been used achieving a lower data rate of 1.5 Mbps with a higher energy efficiency of 2.47 nJ/bit, thus consuming a total power of 3.7 mW for an output power of −20 dBm. A PPM+BPSK modulation device has achieved an energy efficiency of 280 pJ/bit with an output power of −16 dBm and a data rate of 15.6 Mbps. The total power in this case is 4.36 mW. Previous work uses an IR-UWB transmitter with 8-Array PPM modulation to achieve a data rate of 12 Mb/s with an energy efficiency of 45 pJ/bit. The output power of the transmitter is −26 dBm with a low power consumption of 0.54 mW. Thus, IR-UWB modulation helped in achieving high data rates at a low power in this work, while the multi-array PPM helped in reducing the peak to average power ratio.

The approaches disclosed herein move beyond earlier attempts of stimulation artifact cancellation by adaptive filters in the following ways. First, the mapping from the stimulation signal to the contamination signal is not necessarily linear. Some implementations include formulating modeling structures that incorporate both linear and nonlinear elements in order to enhance the ability of the model to capture nonlinear effects. Second, when neural recordings are collected from multiple locations simultaneously, the contaminants in all these readings are correlated with each other since they are generated by the same stimulation signal. In this case, the data from the various recordings need to be processed jointly because their correlation can be exploited to enhance accuracy beyond normal LMS adaptation. Some implementations include pursuing a multi-channel adaptive strategy to take advantage of this additional level of information in the data. Third, the stimulation signal tends to have well defined periodic shape and periodicity, such as rectangular pulses. This prior information can be exploited to drive the learning process and to enhance its convergence rate and cancelation ability. Fourth the size of the contamination signals is much larger than the desired neural signal, often 20× larger. This suggests the possibility of applying successive interference cancelation techniques to drive the adaptation process. If, on a first pass over the data, one views the neural signals as noise, then adaptive techniques can be used to estimate the unknown mappings, which in turn can be used to clean the data.

Medtronic's Activa-PC+S is a highly configurable system capable of simultaneously recording and stimulating from deep structures in the brain on two channels. The Medtronic system represents a major step forward in neural therapeutics; however, there remain numerous impediments to translating such a system into a highly scaled closed-loop therapeutic device for multi-region neural recording and neuromodulation. The Medtronic system contains high-power electronics with a large battery housed in the chest cavity necessitating long wires that run from the chest to the top of the cranium and tunnel through the skull that create an infection risk. Scaled up to stimulate and record in 8 regions the electronics could not be sustained for a long period of time by a battery.

Neuropace's RNS system is designed specifically for the treatment of epilepsy. Neuropace has recently obtained FDA approval for the system, which supports four ECoG recording channels and one stimulation channel. The system is powered from a compact battery that is housed within the cranium and requires an invasive surgery to implant. The system can perform seizure detection and is configurable; however, the device is designed for therapeutic purposes, with minimal readout functionality. The device suffers from the same scaling limitations as the Medtronic device.

The Blackrock Array is an array of 100 penetrating silicon microelectrodes designed to record from neurons in the intracortical region. These arrays have good acute performance, however, after months of implantation, the number of electrodes which can record neuronal activity significantly decreases.

Existing closed-loop neuromodulation systems exhibit limited saturation-free input range (up to ~5 mV interferers) and cannot achieve artifact-free recording and stimulation concurrently. They are limited by either the input range or short recording dead-time in the presence of stimulation artifacts.

All existing neural-signal amplifiers use one amplifier per channel to meet the input-noise specification, despite the fact that intrinsic amplifier bandwidth is much wider than the signal bandwidth.

The devices disclosed herein have several advantages over current technologies:

For chronically implantable neural interfaces, some implementations include employing high channel count polymer-based arrays microfabricated for long-term stability. These polymers have much lower elastic modulus (~3 GPa) compared to state-of-the-art silicon devices (~200 GPa) or microwire devices (~100 GPa) and much lower foreign body response. A polyimide-based retinal prosthesis with over 240 electrodes has a projected lifespan of 15+ years.

Some implementations include using high-density miniaturized packages that provide for compact electronic systems that can be embedded using less invasive surgical techniques.

Some implementations include achieving 200 mVpp artifact-free input range (a 20× better than existing technology) by employing signal processing in (unbounded) phase domain. This is accomplished without compromising power consumption (less than 1 µW/channel for LFPs).

Some implementations include using adaptive filter to remove stimulation artifact from affected recording channels.

Some implementations include use of a revolutionary frequency-division multiplexing approach, combined with impedance-based filtering, which allows for sharing of the power-hungry input amplifier across several channels and effectively reduces power without compromising noise. Some implementations include achieving record-low 0.8 µA/channel single-unit recording, thereby balancing power with LFP front-end system.

A combination of above techniques, together with secure wireless data and power transfer, allows for production of a record-small (less than 1 cm$^3$) 64-channel battery-free implantable neural recording and stimulation device. The device improves state-of-the-art technology by ~10× in electrode array density, ~100× in device volume/channel, and sets new frontiers for neuroscience and clinical applications.

In rodents, there is substantial ongoing work investigating plasticity after experimental TBI, although much has focused on recovery from focal traumatic lesions to the motor cortex. Many experimental studies investigating post-traumatic memory impairments utilize models well known to cause substantial hippocampal structural damage and/or widespread neuronal loss. Previous studies have focused on experimental TBI models that demonstrate hippocampal memory impairment and loss of experience-dependent neuroplasticity even in the absence of a gross histological lesion in the hippocampus or even substantial cell loss in the hippocampus. These models then focus on post-traumatic neuronal dysfunction rather than neuronal loss. This is an important distinction for devising stimulation-based methods for memory restoration—brain structures that are completely destroyed may not be amenable to proper stimulation or function. A molecular to behavioral mechanistic linkage has been demonstrated that creates a strong foundation for interventions to facilitate memory recovery. From changes in glutamatergic receptor subunits and signal transduction molecules, correlative impairments of ex vivo electrophysiology, functional hippocampal imaging and hippocampal-based memory impairments have been shown. These processes coincide with a time window of impaired experience-dependent neuroplasticity.

Simply waiting for transient molecular disturbances results in some return in memory functions, however, this approach results in incomplete recovery, as memory acquisition appears to respond more robustly but spatial memory retention does not. Furthermore, preliminary data indicates that pharmacological activation of these impaired glutamatergic mechanisms results in complete restoration of memory impairments and experience-dependent neuroplasticity. Feasibility of stimulation of the medial septal nuclei after experimental TBI has been demonstrated to restore patterned hippocampal activity (theta rhythms) and spatial memory in the Barnes maze.

The disclosed systems have some distinct advantages. First, the recordings of patterned hippocampal activity such as post-TBI theta rhythms are conducted using a novel wireless system. Animal behaviors are more natural when untethered, and, in particular, this allows the monitoring of experience-dependent plasticity in an enriched environment. Furthermore, the elaborate monitoring and virtual reality system (EP+NR) allows for more sophisticated examination of electrical activity underlying the memory process when tethered recordings are used.

For non-human primate studies, a majority of current work on understanding memory processing in the temporal lobe has focused on understanding the role of neural oscillations and single unit recordings while primates examine objects. In addition, Rolls has continued to refine his models of processing within the temporal lobe. Of more relevance is recent work by Hampson et al., who examined the effects of stimulation in CA1 while animals perform a delayed match-to-sample task. They found that stimulation during the sample phase improved performance, particularly on difficult trials. The disclosed implementations differ from Hampson et al. both in terms of the site of stimulation and in terms of the behavioral tasks. For example, the disclosed tasks involve more than just short-term memory; the animals have to remember as many as three components (scene, object/face and location) for multiple stimuli presented in temporal sequence.

In some implementations, within a monitoring unit, simultaneous wide bandwidth electrophysiological (1-3 kHz; sampling 10 kHz per channel) and video recording are carried out using a portable 256-channel Nihon Kohden monitoring system. In some implementations, a 196-channel Neuralynx Atlas amplification and recording system is rolled into the patient's room and rapidly connected to external leads from intracranial clinical electrodes and microelectrodes electrophysiological to record wide bandwidth (1-6 kHz; sampling 30 kHz per channel) depth EEG, local field potentials, and single neuron activity.

Some implementations include operating a Siemens 3 Tesla Tim Trio (3T) MRI scanner, equipped with 32 receiver channels, including software and sequences for acquiring anatomical, functional (BOLD and arterial spin labeling), diffusion-weighted, and spectroscopic images of the brain. In some implementations, the 3T MRI unit is equipped with multiple a Siemens headphone/speaker system, a Resonance Technology Corporation (RTC) Visuastim digital system, and an LCD projection system based on an Acer data projector controlled via fiberoptic cabling, and a dedicated Mac computer set up to run E-Prime and Psychtoolbox. In some implementations, the response recording system includes a Current Design 4-button response pad and a 32 channel electronic interface and power supply unit connected to the response recording computers via a fiber optic bundle. In some implementations, an MRI simulator that gives subjects an experience similar to live scanning is used, which allows characterization of subject performance without booking and charging for scan time. Some implementations include utilizing an EEG system based on the EEG MRI compatible designs, which allows for concurrent recording of EEG and fMRI signals, enabling joint studies associating the two physiological measures. Some implementations include utilizing analysis software including the source space calculation tool, Geosource. Some implementations include utilizing software access points for real-time recording and analysis, to develop real-time joint EEG and fMRI analyses. Some implementations include utilizing a shared cluster. For example a shared cluster with 1,100+64-bit nodes and 11,100 cores, with a IGB Ethernet network and 10, 20, 40 Gb InfiniBand interconnect, including a scheduler, gcc and compilers for C, C++, Fortran 77, 90, and 95 on the current shared cluster architecture. In some implementations, the current peak performance of the cluster is in order of 110 trillion double-precision floating operations per second (TFLOPS) with CPUs, plus another 200 TFLOPS with GPUs.

Some implementations include utilizing semiconductor processing equipment required for the fabrication and assembly of neural interfaces. This includes one or more of the following equipment: deep reactive ion etcher for dielectric materials, reactive ion etcher for polymers, sputtering and e-beam evaporation deposition systems, atomic layer deposition, automatic thin-film spinners, photolithographic contact aligner, automatic wire bonder, flip chip bonder, parylene vapor deposition system, screen printer, tensile testers, environmental chamber, high temperature vacuum oven, optical profilometers, interferometer, FTIR spectrometer, ellipsometer, and optical inspection microscopes. Some implementations include utilizing customized electrochemical systems for the activation and characterization of the neural interface tissue. This includes one or more of the following equipment: Alpha Omega Systems AlphaLab SnR stimulation and recording system, Gamry electrochemical system, PAR electrochemical system, Hirox microscope, Inverted microscopes, and electrochemical test stations.

Some implementations include utilizing high-speed instrumentation for the testing of electronic circuits. The instrumentation includes one or more of: low-noise RF generators, spectrum analyzers, high-speed oscilloscopes, logic analyzers, FPGA prototyping boards, and a high-speed probe station.

Some implementations include utilizing cutting-edge electronic measurement capability up to 220 GHz. This includes measurement instruments in time and frequency domain and for wireless testing including one or more of: real-time oscilloscopes, Agilent DCA 86100D 70 GHz sampling oscilloscope, signal generators up to 65 GHz, a four-port VNA setup up to 110 GHz (ZVA 110E from R&S) with extensions up to 220 GHz, pulse generators, spectrum analyzers, and other electronic test facilities such as a 12K series Cascade Microtech probe station.

Some implementations include utilizing sound, light, EMF and RF, double-wall shielded electrophysiology rooms. In some implementations, these rooms have virtual reality mazes and/or real world mazes. Some implementations include utilizing 128-channel digital Neuralynx data acquisition systems for electrophysiological recordings in these mazes in these rooms.

Some implementations include utilizing an animal MRI such as a Bruker Biospin 7.0 Tesla magnetic resonance imaging/spectroscopy instrument having a clear bore diameter of 30 cm.

Figure 12A:
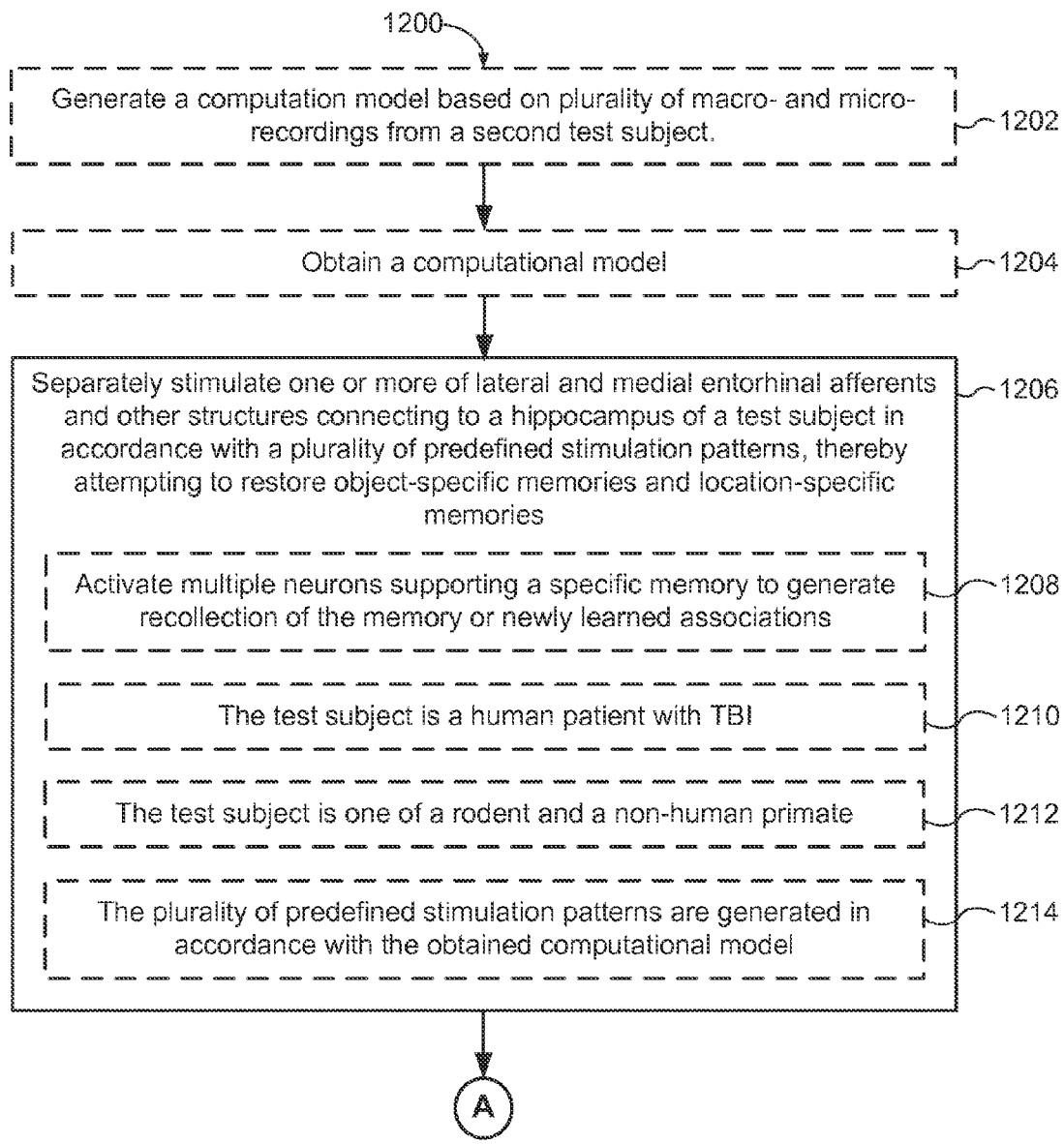
FIGS. 12A-12B illustrate a flowchart representation of a method of developing and refining a computation model for restoring memories, in accordance with some implementations.
Figure 12B:
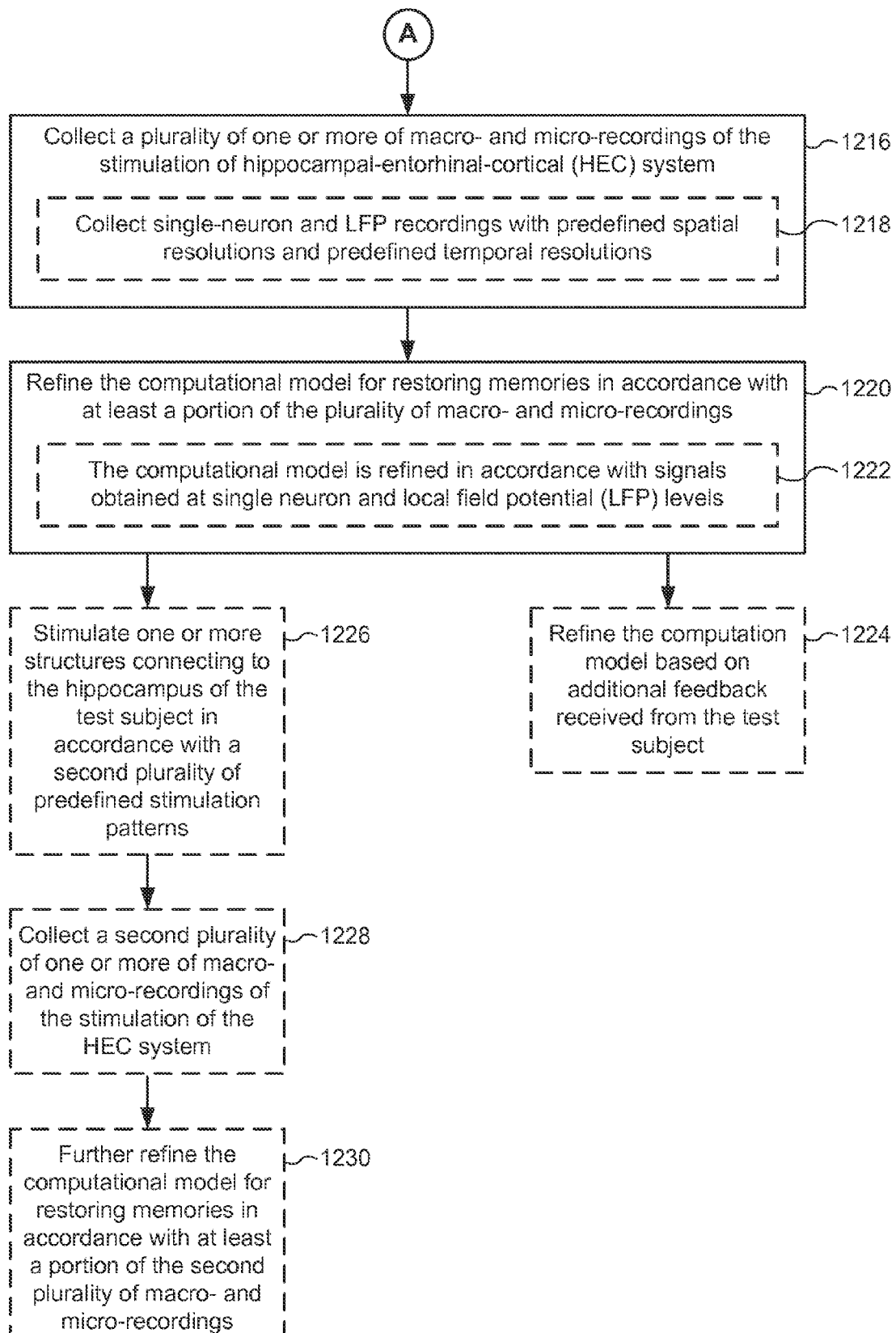
Figure 13A:
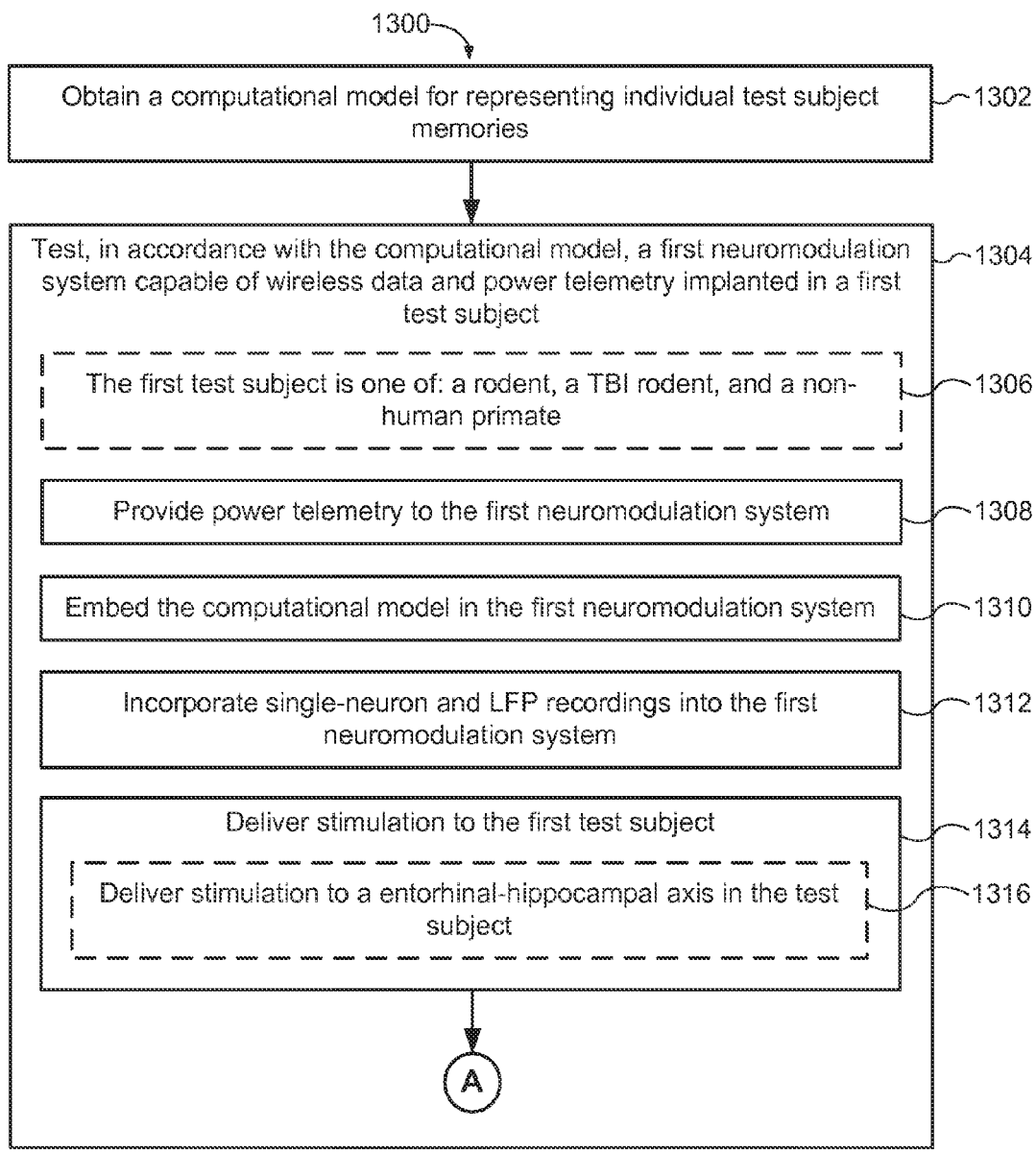
FIGS. 13A-13B illustrate a flowchart representation of a method for restoring memories, in accordance with some implementations.
Figure 13B:
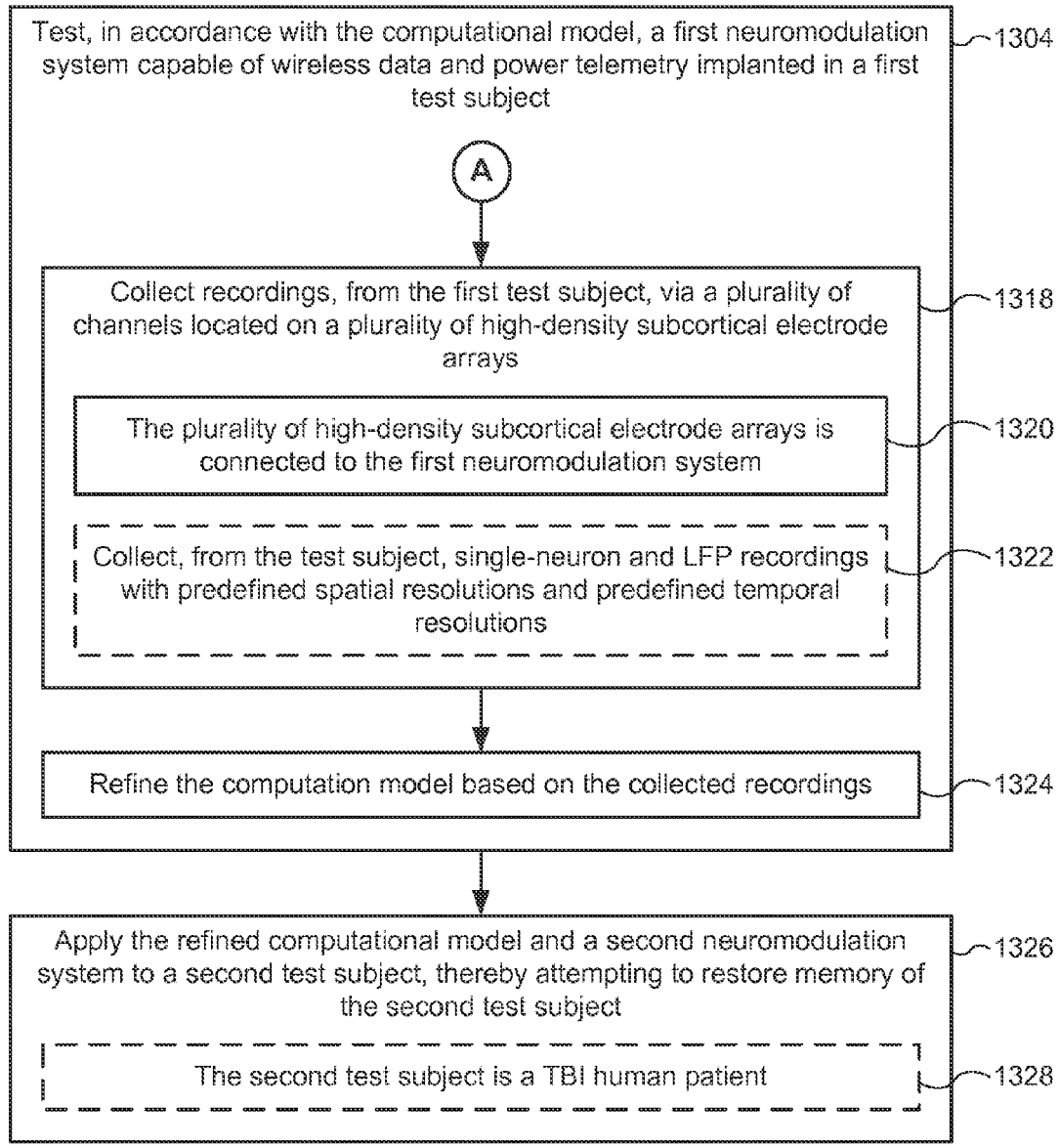

Attention is now directed to the flowcharts. FIGS. 12A-12B illustrate a flowchart representation of a method of developing and refining a computation model for restoring memories, in accordance with some implementations. FIGS. 13A-13B illustrate a flowchart representation of a method for restoring memories, in accordance with some implementations.

FIGS. 12A-12B illustrate a flowchart diagram of a method 1200 for developing and refining a computational model for restoring memories in accordance with some implementations. In some implementations, the method 1200 is performed by a computing system with one or more processors, memory, and a display. For example, in some implementations, the method 1200 is performed by computing system 100 (FIG. 1), neural modulation system 700 (FIG. 7), or a component thereof (e.g., device 102A, FIG. 1). In some implementations, the method 1200 is performed by an electronic device such as the implantable electronics package 200 (FIG. 2). In some implementations, the method 1200 is governed by instructions that are stored in a non-transitory computer readable storage medium and the instructions are executed by one or more processors of an electronic device (e.g., device 102A, FIG. 1). Optional operations are indicated by dashed lines (e.g., boxes with dashed-line borders).

In some implementations, the system generates (1202) a computation model based on plurality of macro- and micro-recordings from a second test subject. In some implementations, the system generates the computation model based on recording from a second test subject prior to stimulating a first test subject. In some implementations, the system generates the computational model based on recordings from a plurality of test subjects.

In some implementations, the system obtains (1204) a computational model. In some implementations, the computational model is obtained from a second system external to the system. In some implementations, the computational model is retrieved from memory within the system (e.g., memory within memory restoration system 106, FIG. 1).

The system separately stimulates (1206) lateral and medial entorhinal afferents and other structures connecting to a hippocampus of a test subject in accordance with a plurality of predefined stimulation patterns, thereby attempting to restore object-specific memories and location-specific memories. In some implementations, system separately stimulates via an implantable electronics package, such as implantable electronics package 200 (FIG. 2). For example, the system stimulates the lateral and medial entorhinal afferents to the hippocampus via a sub-cortical electrode array such as sub-cortical electrode array 302 (FIG. 3A). In some implementations, the stimulations are generated at a stimulation module, such as stimulation module 118 and/or stimulation module 150 (FIG. 1).

In some implementations, the system activates (1208) multiple neurons supporting a specific memory to generate recollection of the memory or newly learned associations. For example, the system actives the multiple neurons via a sub-cortical electrode array such as sub-cortical electrode array 302, FIG. 3A.

In some implementations, the test subject is (1210) a human patient with TBI.

In some implementations, the test subject is (1212) one of a rodent and a non-human primate.

In some implementations, the plurality of predefined stimulation patterns are generated (1214) in accordance with the obtained computational model. For example, a request to stimulate a particular memory is input into the computational model and, in response, the computation model outputs the plurality of predefined stimulation patterns.

The system collects (1216) a plurality of macro- and micro-recordings of the stimulation of hippocampal-entorhinal-cortical system. For example, the system collects the recordings via a feedback module such as feedback collection module 110 (FIG. 1). In some implementations, the system collects the recordings via a collection module such as collection module 170 (FIG. 1).

In some implementations, the system collects (1218) single-neuron and LFP recordings with predefined spatial resolutions and predefined temporal resolutions.

The system refines (1220) a computational model for restoring individual memories in accordance with at least a portion of the plurality of macro- and micro-recordings. For example, the system refines computational model 114 (FIG. 1) using analysis module 180 (FIG. 1).

In some implementations, the computational model is refined (1222) in accordance with signals obtained at single neuron and local field potential levels.

In some implementations, the system refines (1224) the computation model based on additional feedback received from the test subject. For example, the system refines the model based on verbal feedback from the test subject. In some implementations the additional feedback includes verbal feedback, visual feedback, health indicators for the test subject, feedback regarding other portions of the test subject's brain or body, and the like.

In some implementations, the system stimulates (1226) one or more structures connecting to the hippocampus of the test subject in accordance with a second plurality of predefined stimulation patterns.

In some implementations, the system collects (1228) a second plurality of one or more of macro- and micro-recordings of the stimulation of the HEC system.

In some implementations, the system further refines (1230) the computational model for restoring memories in accordance with at least a portion of the second plurality of macro- and micro-recordings.

FIGS. 13A-13B illustrate a flowchart diagram of a method 1300 for restoring memories in accordance with some implementations. In some implementations, the method 1300 is performed by a computing system with one or more processors, memory, and a display. For example, in some implementations, the method 1300 is performed by computing system 100 (FIG. 1), neural modulation system 700 (FIG. 7), or a component thereof (e.g., device 102A, FIG. 1). In some implementations, the method 1300 is governed by instructions that are stored in a non-transitory computer readable storage medium and the instructions are executed by one or more processors of the system. Optional operations are indicated by dashed lines (e.g., boxes with dashed-line borders).

The system obtains (1302) a computational model for representing individual test subject memories. In some implementations, the computation model (e.g., computation model 114) is stored at a memory restoration system such as memory restoration system 106. In some implementations, the computation model is stored within an implantable electronics package such as implantable electronics package 200 (FIG. 2). In some implementations, the computation model is generated by the system (e.g., based on preliminary data and/or data from previous test subjects/trials).

The system tests (1304), in accordance with the computational model, a first neuromodulation system capable of wireless data and power telemetry implanted in a first test subject. For example, FIG. 6 shows a virtual reality apparatus and environment 600 for testing a computation model with rats.

In some implementations, the first test subject is (1306) one of: a rodent, a TBI rodent, and a non-human primate. For example, the first test subject is a rat in the virtual rodent arena as shown in FIG. 7.

The testing includes the system providing (1308) power telemetry to the first neuromodulation system. In some implementations, the power telemetry is provided wirelessly via RF coils as illustrated by power and control circuitry 500 (FIG. 5).

The testing includes the system embedding (1310) the computational model in the first neuromodulation system. In some implementations, the computation model is embedded within an implantable electronics package such as implantable electronics package 200 (FIG. 2).

The testing includes the system incorporating (1312) single-neuron and LFP recordings into the first neuromodulation system.

The testing includes the system delivering (1314) stimulation to the first test subject. In some implementations, system delivers stimulation via an implantable electronics package, such as implantable electronics package 200 (FIG. 2). For example, the system delivers stimulation via a sub-cortical electrode array such as sub-cortical electrode array 302 (FIG. 3A). In some implementations, the stimulations are generated at a stimulation module, such as stimulation module 118 and/or stimulation module 150 (FIG. 1).

In some implementations, the system delivers (1316) stimulation to a entorhinal-hippocampal axis in the test subject. For example, the system delivers the stimulation via a sub-cortical electrode array implanted in the entorhinal-hippocampal axis in the test subject, such as sub-cortical probe 210 (FIG. 2).

The testing includes the system collecting (1318) recordings, from the first test subject, via a plurality of channels located on a plurality of high-density sub-cortical electrode arrays. For example, the system collects the recordings via a feedback module such as feedback collection module 110 (FIG. 1). In some implementations, the system collects the recordings via a collection module such as collection module 170 (FIG. 1). In some implementations, the recordings are collected through the sub-cortical electrode arrays.

The plurality of high-density sub-cortical electrode arrays is (1320) connected to the first neuromodulation system. In some implementations, the plurality of high-density sub-cortical electrode arrays is a component of the first neuromodulation system. In some implementations, the plurality of high-density sub-cortical electrode arrays are connected to the first neuromodulation system as shown in FIG. 2 with reference to probes 208 and 210 and electronics module 206. In some implementations, the plurality of high-density sub-cortical electrode arrays are coupled to the first neuromodulation system.

In some implementations, the system collects (1322), from the test subject, single-neuron and LFP recordings with predefined spatial resolutions and predefined temporal resolutions.

The testing includes the system refining (1324) the computation model based on the collected recordings.

The system applies (1326) the refined computational model and a second neuromodulation system to a second test subject, thereby attempting to restore memory of the second test subject.

In some implementations, the second test subject is (1328) a TBI human patient.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first subject could be termed a second subject, and, similarly, a second subject could be termed a first subject, without changing the meaning of the description, so long as all occurrences of the "first subject" are renamed consistently and all occurrences of the "second subject" are renamed consistently. The first subject and the second subject are both subjects, but they are not the same subject.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A neuromodulation system for enhancing a patient's memory, comprising:
    a plurality of high-density sub-cortical electrode arrays implantable in at least one of a hippocampus and an entorhinal region of the patient;
    a skull-mounted implantable electronics package coupled to the plurality of high-density sub-cortical electrode arrays, the electronics package including one or more processors and memory storing one or more programs for execution by the one or more processors, wherein the one or more programs comprise instructions for:
        delivering stimulation to the patient in which the electronics package has been implanted, including stimulating, via at least a subset of the plurality of electrode arrays, at least one of the hippocampus and the entorhinal regions of the patient;
        concurrently collecting single-neuron and local field potential (LFP) recordings, from the patient via a plurality of channels located on the plurality of high-density sub-cortical electrode arrays; and
        transmitting recordings data from the single-neuron and LFP recordings to an external electronic system;
    the external electronic system wearable by the patient, and configured for:
        embedding a cognitive computational model for memory enhancement;
        updating the cognitive computational model based on the transmitted recordings; and
        providing power and data telemetry to the implantable package, including providing stimulation instructions in accordance with the cognitive computational model.

2. The system of claim 1, wherein the power and data telemetry are provided to the implantable package using an radio frequency (RF) coil system.

3. The system of claim 1, wherein the plurality of channels includes 64 channels.

4. The system of claim 1, wherein the skull-mounted implantable electronics package further comprises:
    a hermetically packaged battery-less electronics module for recording and stimulation;
    one or more coaxial RF coils for power and data telemetry; and
    a sub-cortical probe implanted in the entorhinal cortex.

5. The system of claim 1, wherein the patient is a human patient with a traumatic brain injury (TBI).

6. The system of claim 1, wherein the external electronic system obtains the cognitive computational model from an external server via a communications module.

7. The system of claim 1, wherein the external electronic system is configured to generate a plurality of predefined stimulation patterns based on the cognitive computational model; and
 wherein the stimulation is delivered based on the plurality of predefined stimulation patterns.

8. The system of claim 1, wherein delivering stimulation includes activating multiple neurons supporting a specific memory to generate recollection of the memory or newly learned associations.

\* \* \* \* \*